(12) United States Patent
Nissenbaum et al.

(10) Patent No.: US 6,669,708 B1
(45) Date of Patent: Dec. 30, 2003

(54) DEVICES, SYSTEMS AND METHODS FOR CREATING SUTURELESS ON-DEMAND VASCULAR ANASTOMOSES AND HOLLOW ORGAN COMMUNICATION CHANNELS

(76) Inventors: Michael Nissenbaum, 15 Starbarn Ave., Frenchville, ME (US) 04745; Ducksoo Kim, 9 Cedarhill Rd., Dover, MA (US) 02030; Andy H. Levine, 16 Daniel St., Newton Centre, MA (US) 02459

( * ) Notice: Subject to any disclaimer, the term of this patent is extended or adjusted under 35 U.S.C. 154(b) by 320 days.

(21) Appl. No.: 09/713,589

(22) Filed: Nov. 15, 2000

Related U.S. Application Data

(60) Provisional application No. 60/169,874, filed on Dec. 9, 1999.

(51) Int. Cl.[7] ............................................... A61B 17/34
(52) U.S. Cl. .................. 606/153; 606/151; 604/164.04; 604/164.06; 604/167.06; 604/171
(58) Field of Search .................................. 606/153, 151, 606/167, 155, 185, 158, 108, 213, 91, 192, 194, 198; 604/164.01, 164.02, 164.04, 164.06, 164.09, 165.01, 171, 167.06, 164.1, 172, 174, 198, 175, 192, 264, 265, 506–511; 128/898

(56) References Cited

U.S. PATENT DOCUMENTS

| | | | | |
|---|---|---|---|---|
| 5,122,122 A | * | 6/1992 | Allgood | 604/174 |
| 5,350,393 A | * | 9/1994 | Yoon | 606/185 |
| 5,676,670 A | * | 10/1997 | Kim | 606/108 |
| 5,797,920 A | * | 8/1998 | Kim | 606/108 |
| 6,475,244 B2 | * | 11/2002 | Herveck et al. | 606/157 |

* cited by examiner

*Primary Examiner*—Gloria M. Hale
(74) *Attorney, Agent, or Firm*—David Prashker

(57) ABSTRACT

The present invention provides devices, systems, assemblies, and methods intended for the introduction and sutureless juncture of a prepared communication channel to the interior spatial volume of a blood vessel or a hollow organ within a living subject. The introducer assembly and system is functional and suitable as a complete substitute and replacement for conventionally used apparatus and methods for performing vascular bypass graft surgery in order to overcome an obstruction in a major artery or vein in-vivo. The introducer assembly and system is also most appropriate for use in providing penetration and juncture of a tubular conduit for use as an access duct in order to drain materials from or introduce fluids into the interior spatial volume of a hollow organ in-vivo.

29 Claims, 35 Drawing Sheets

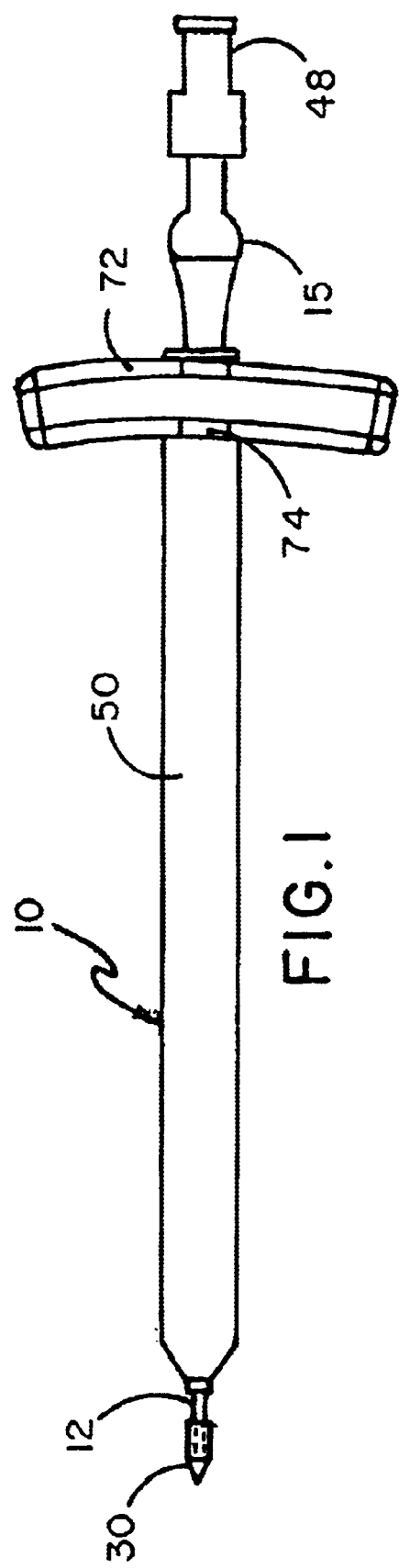

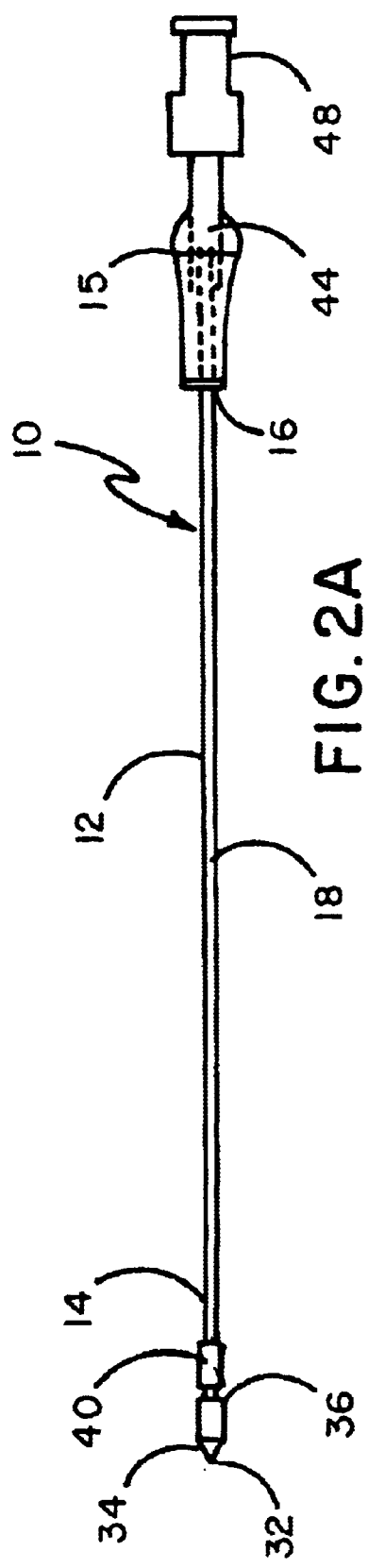
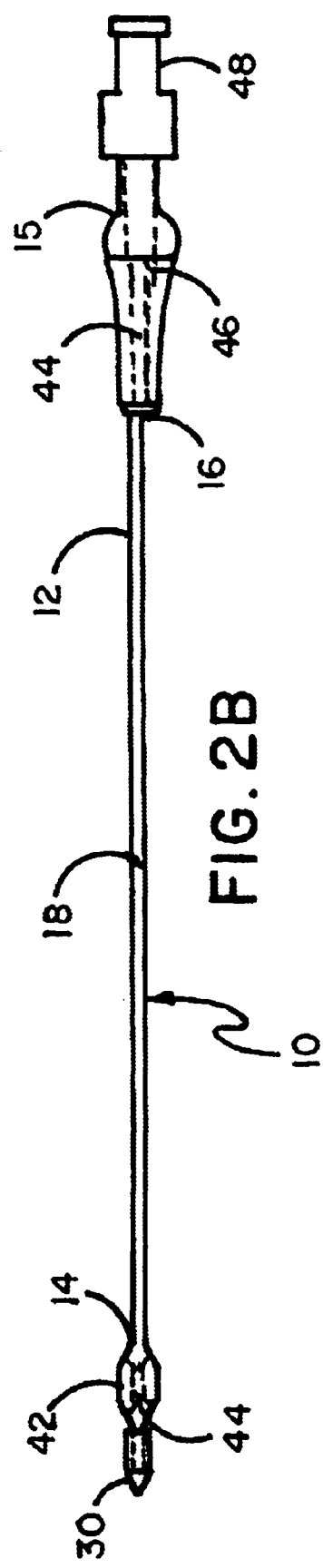

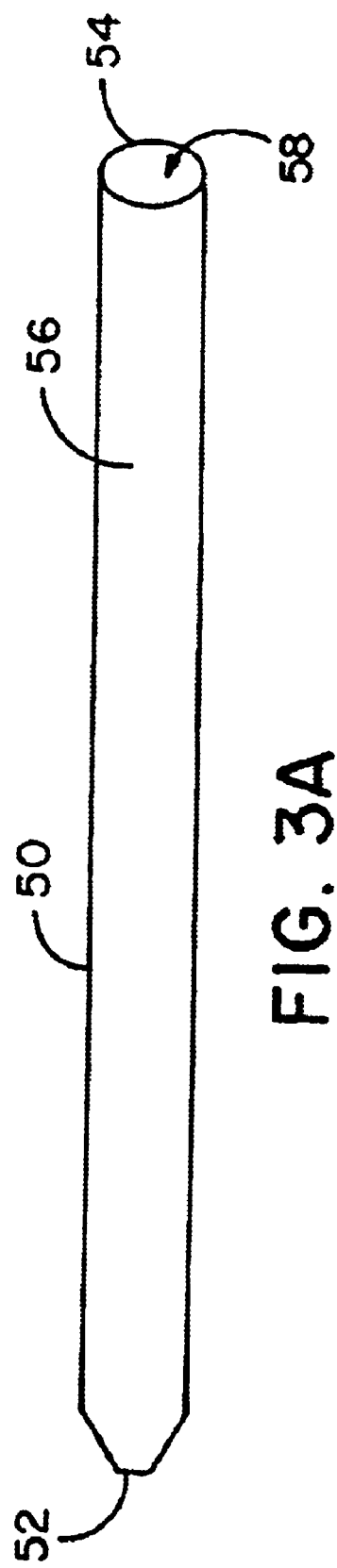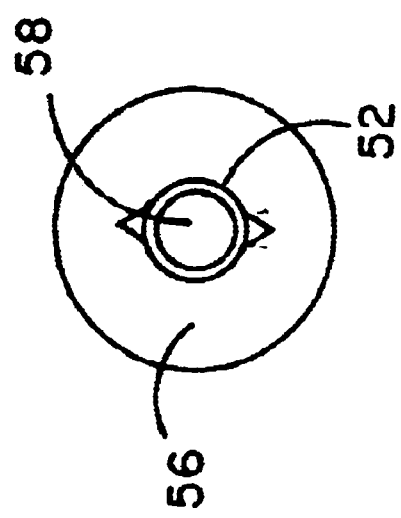
FIG. 3A
FIG. 3B

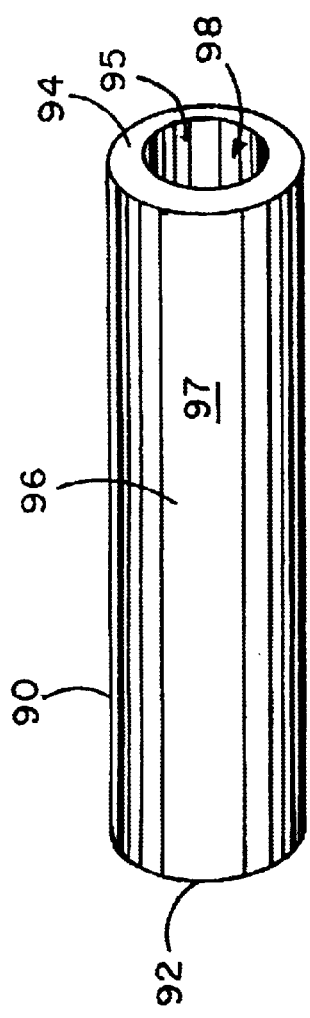
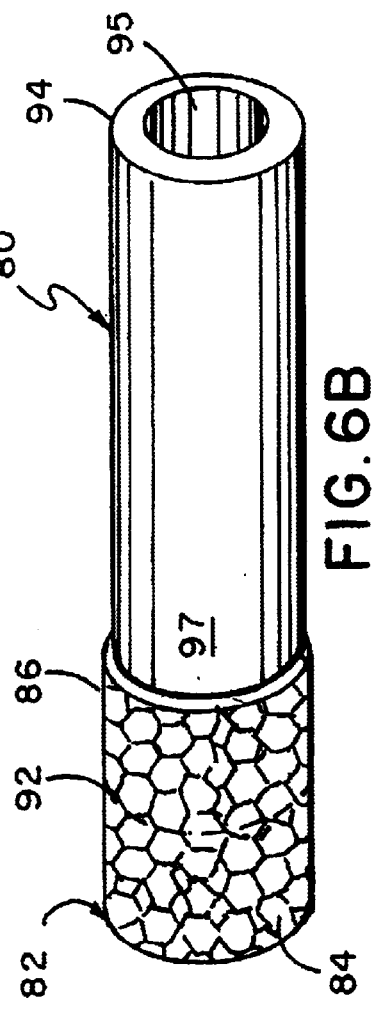
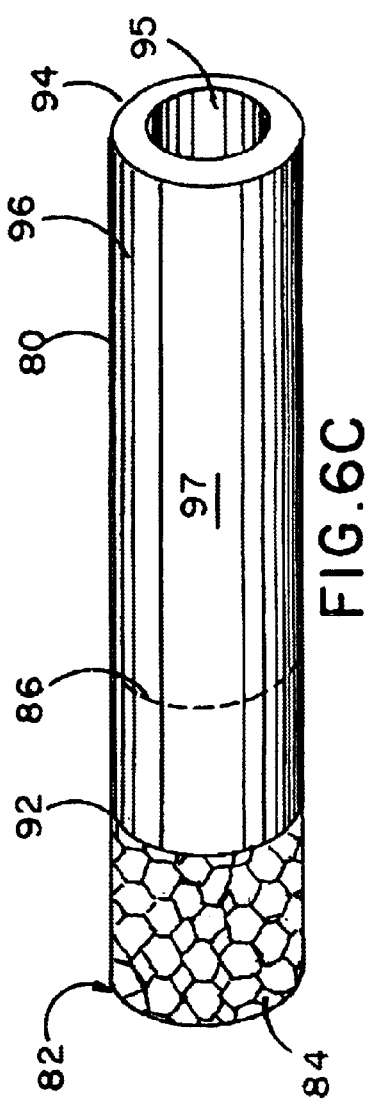
FIG.6A
FIG.6B
FIG.6C

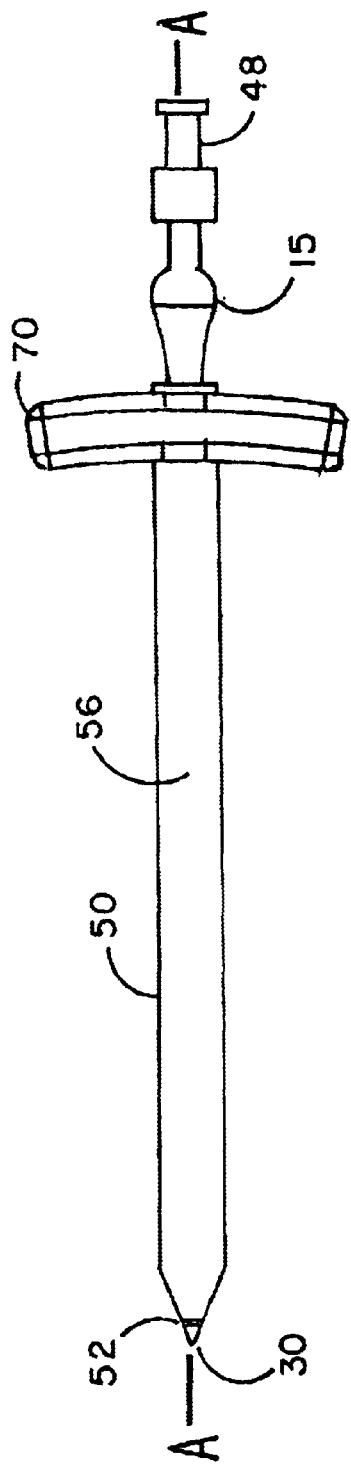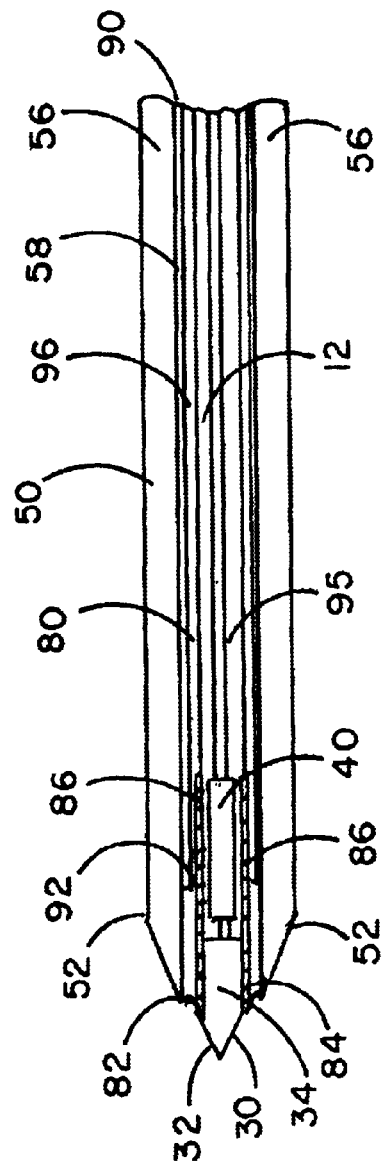

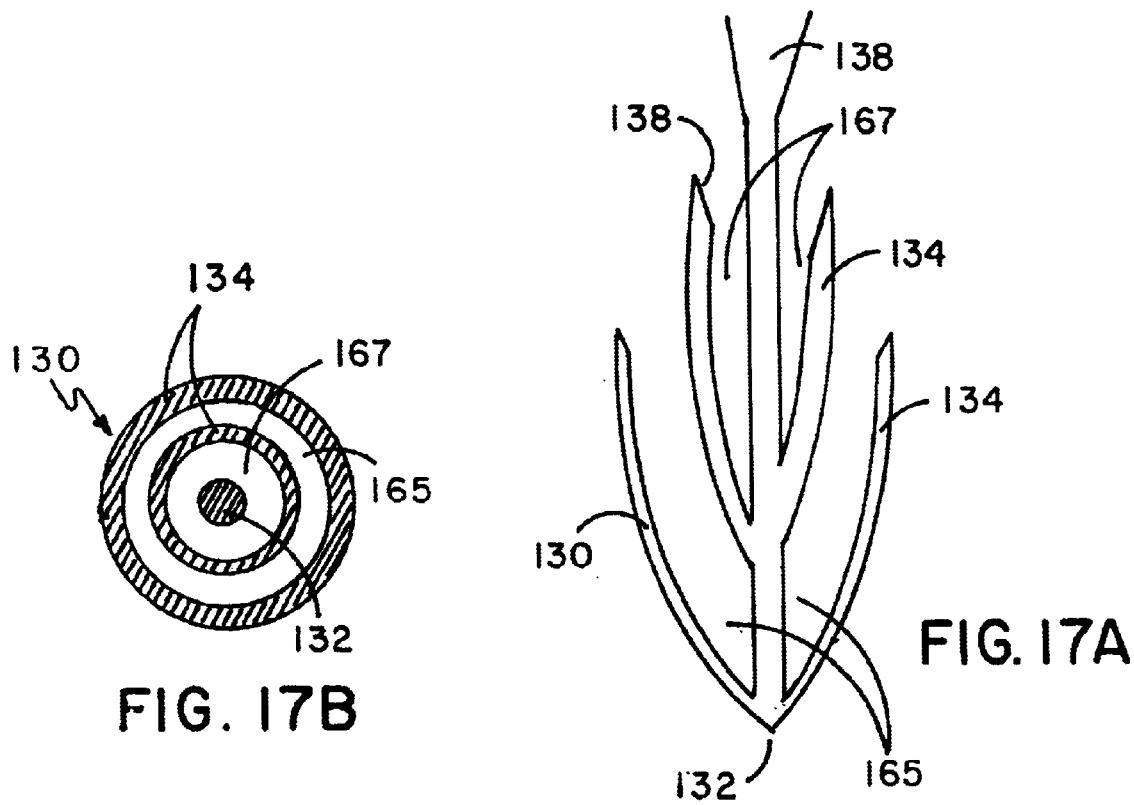
FIG. 17B
FIG. 17A
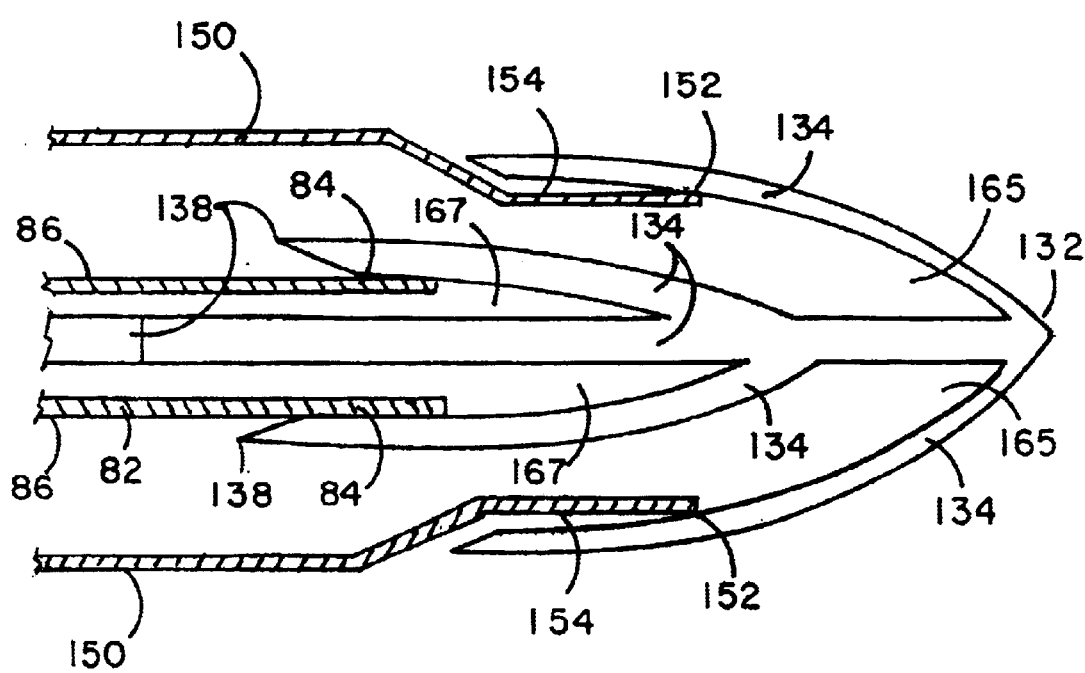
FIG. 19

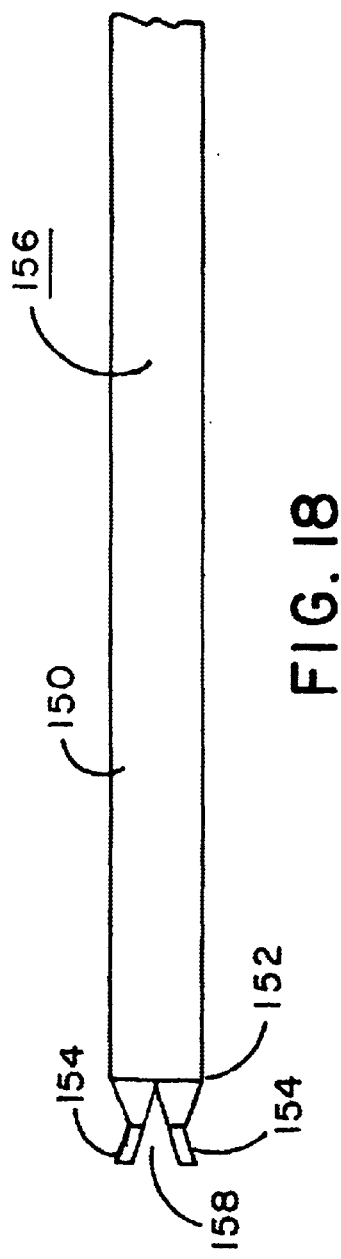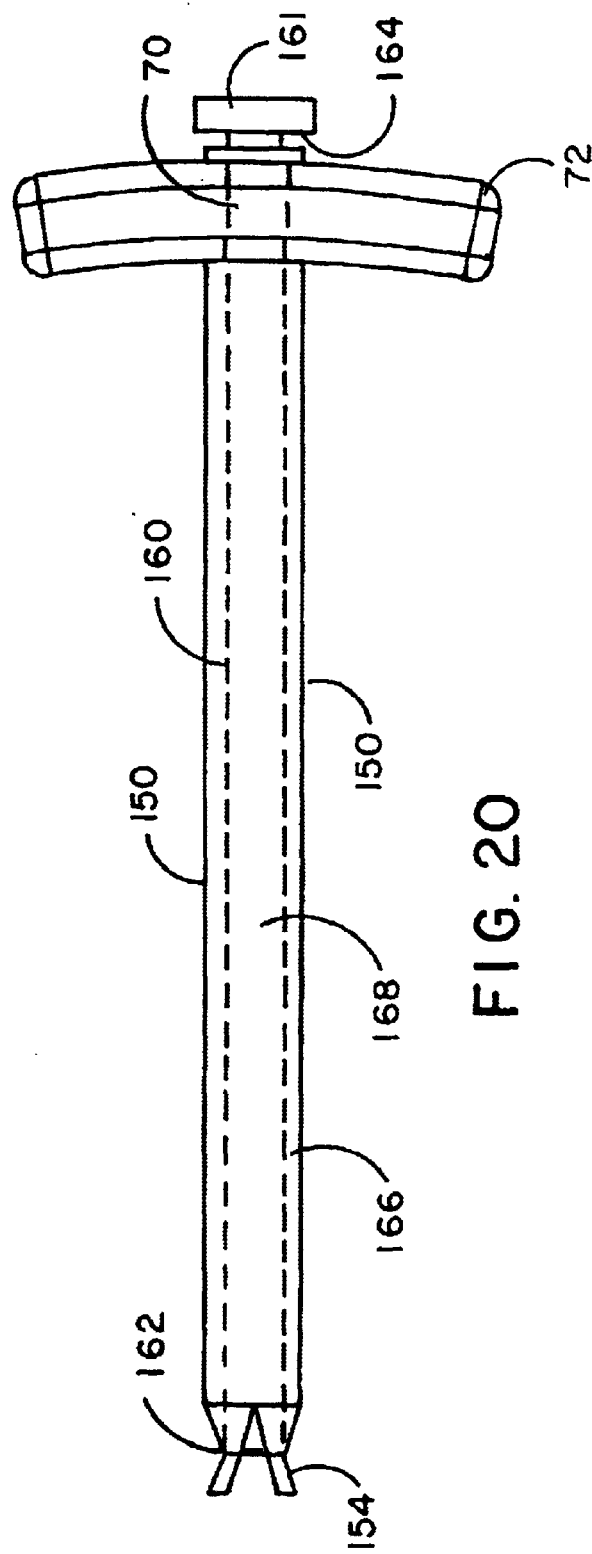

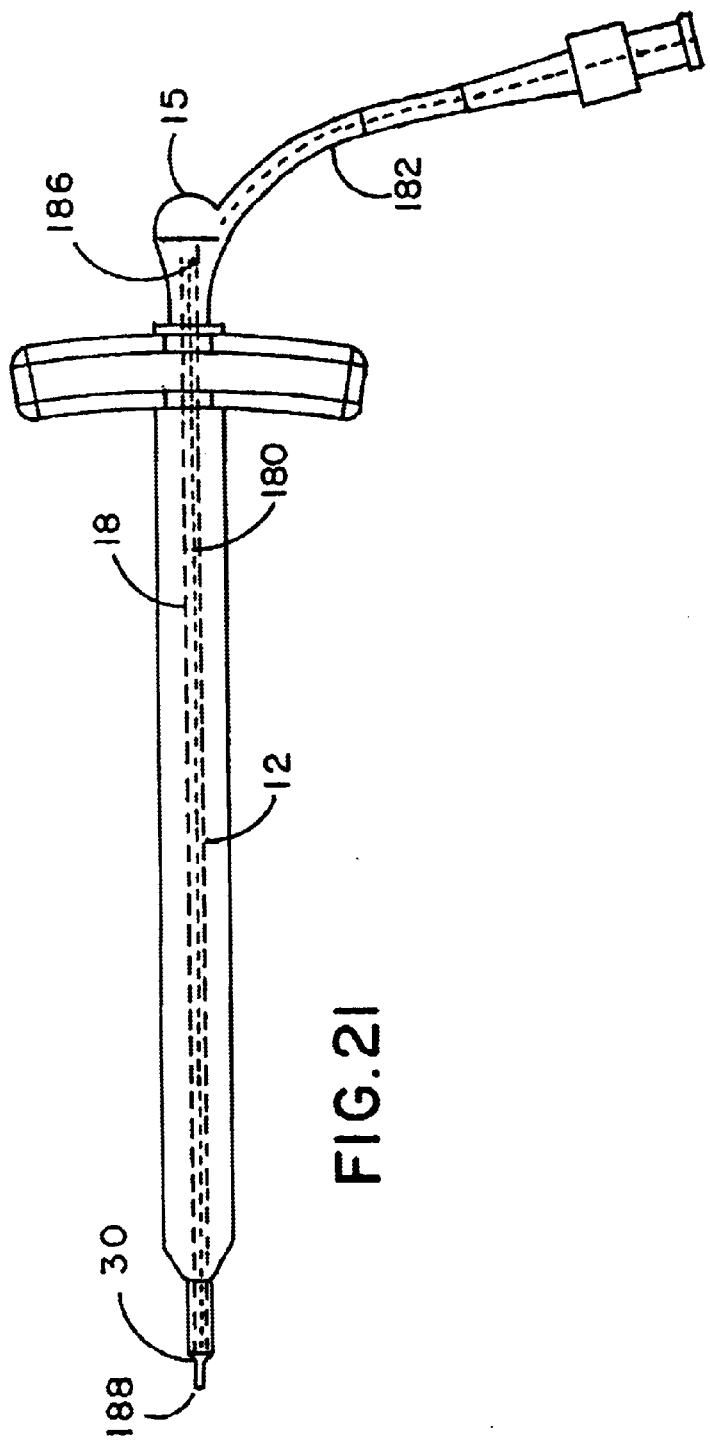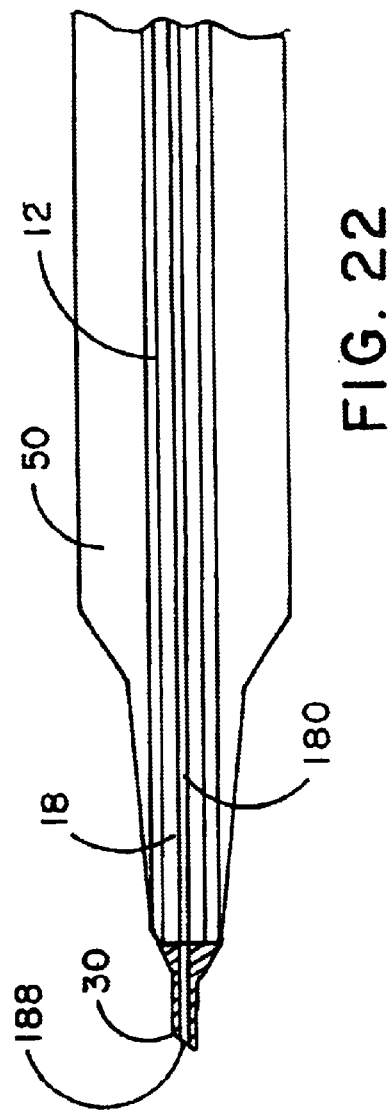

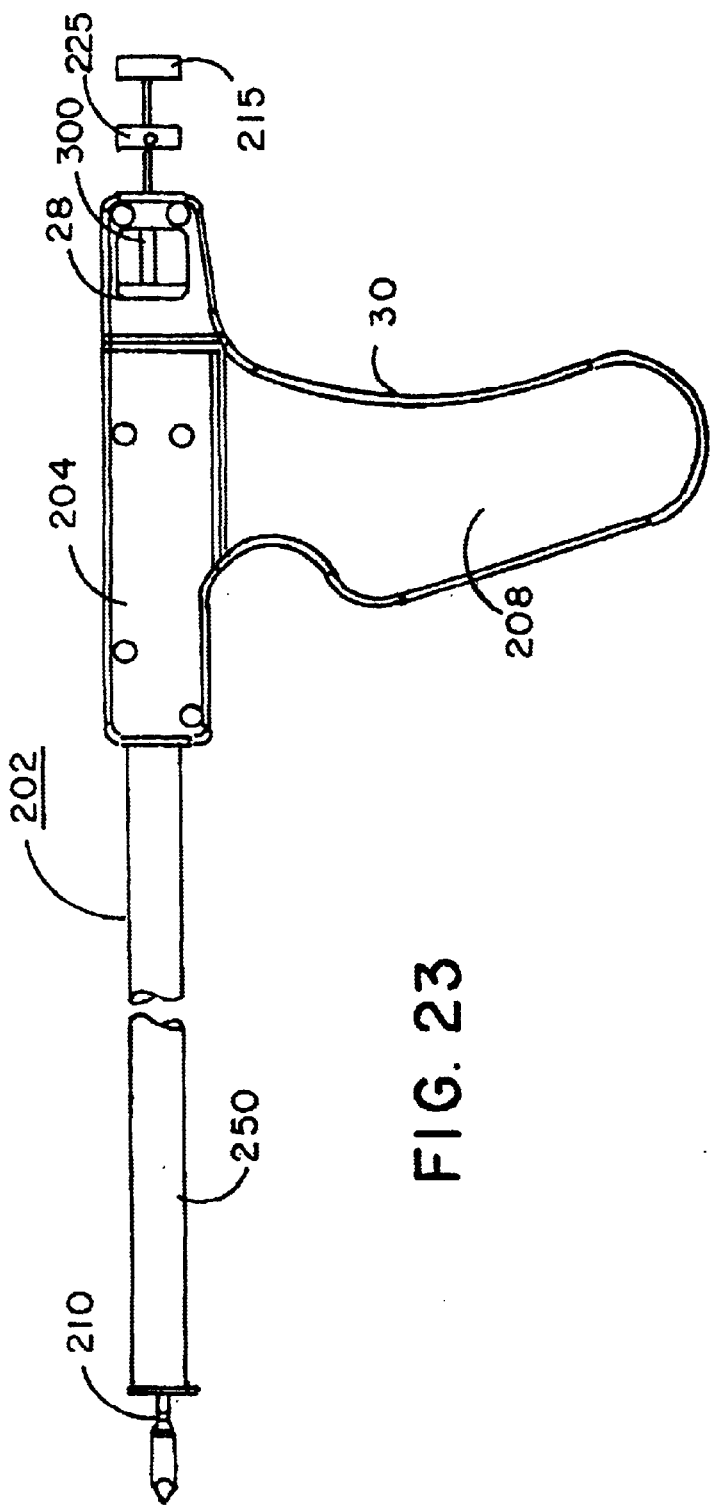
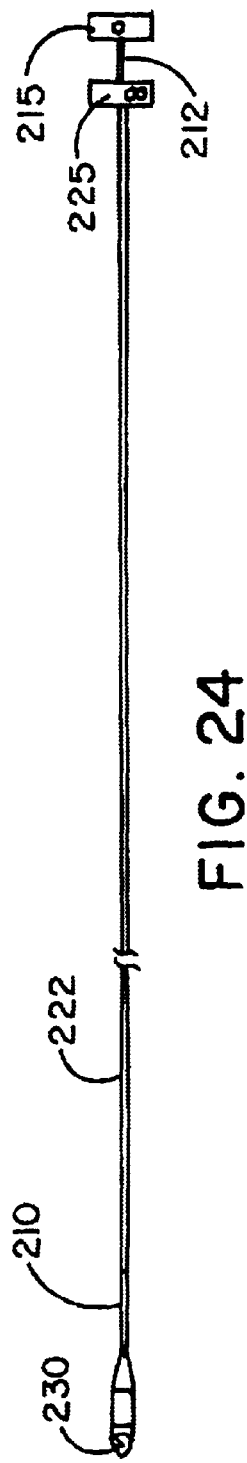
FIG. 23
FIG. 24

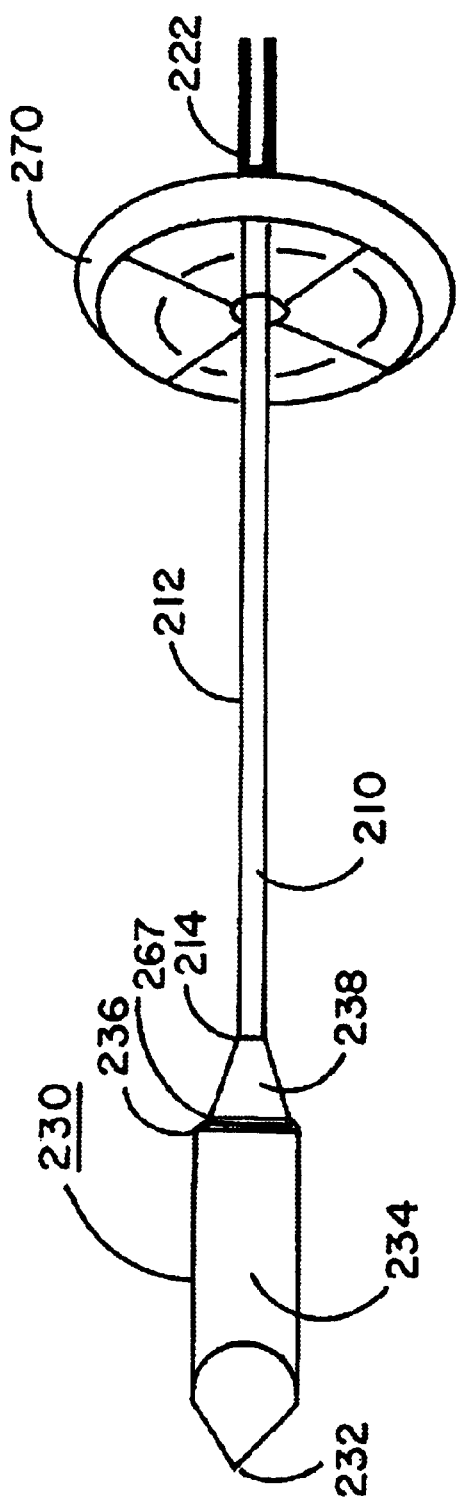
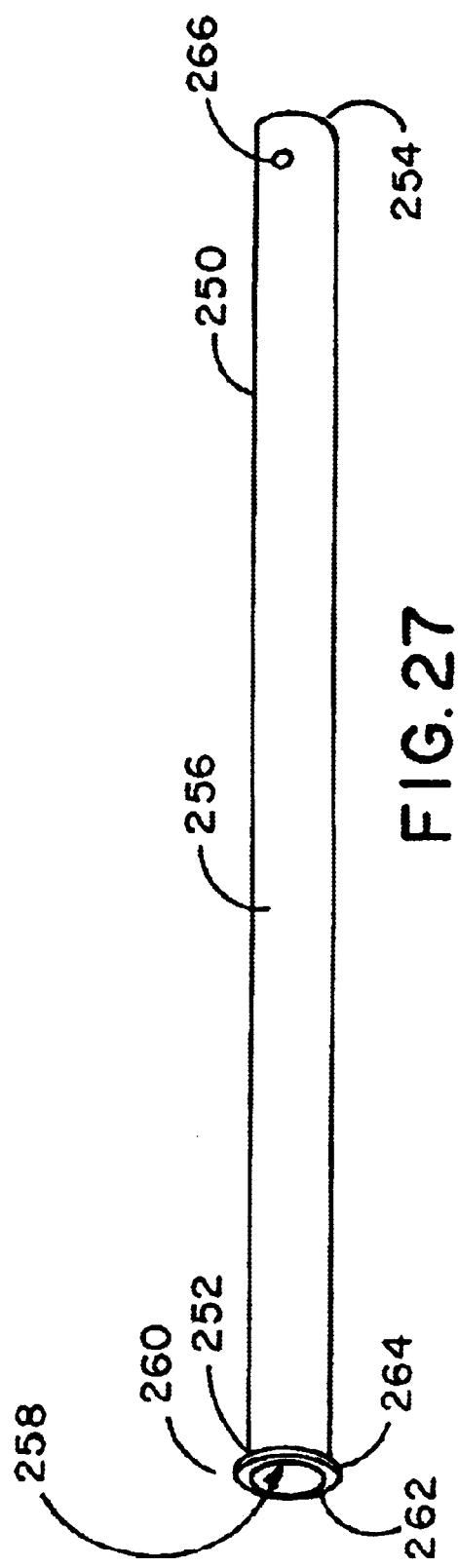

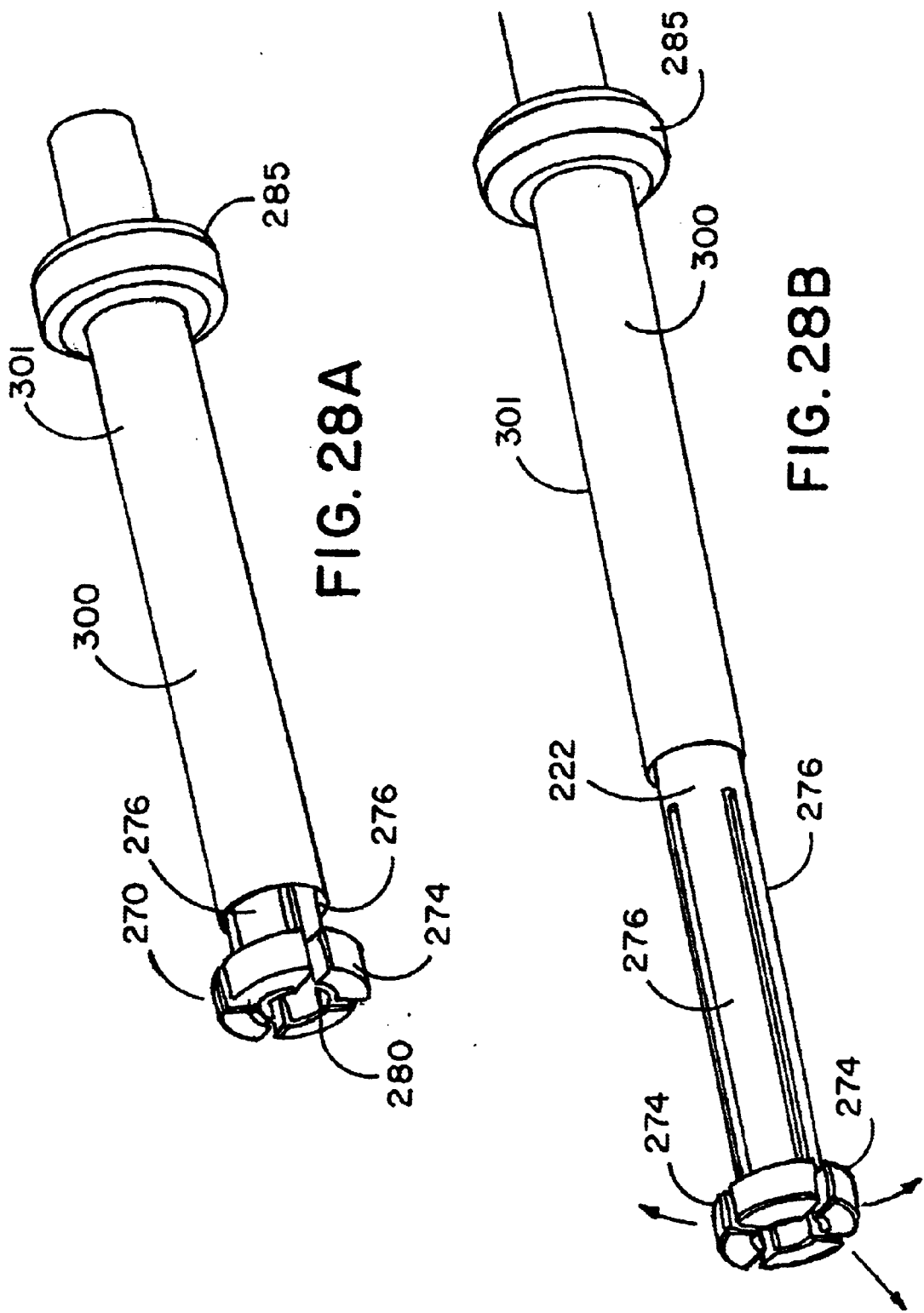

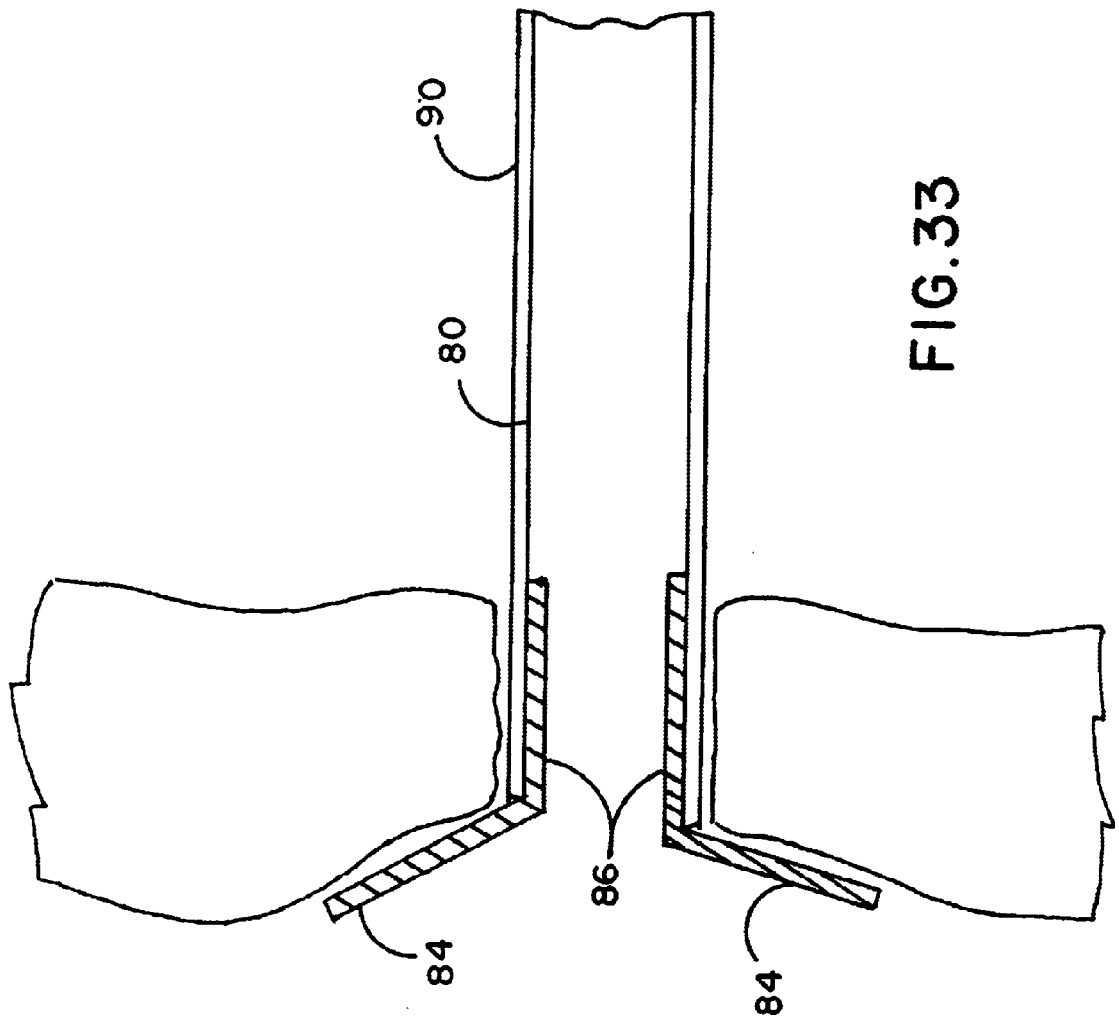

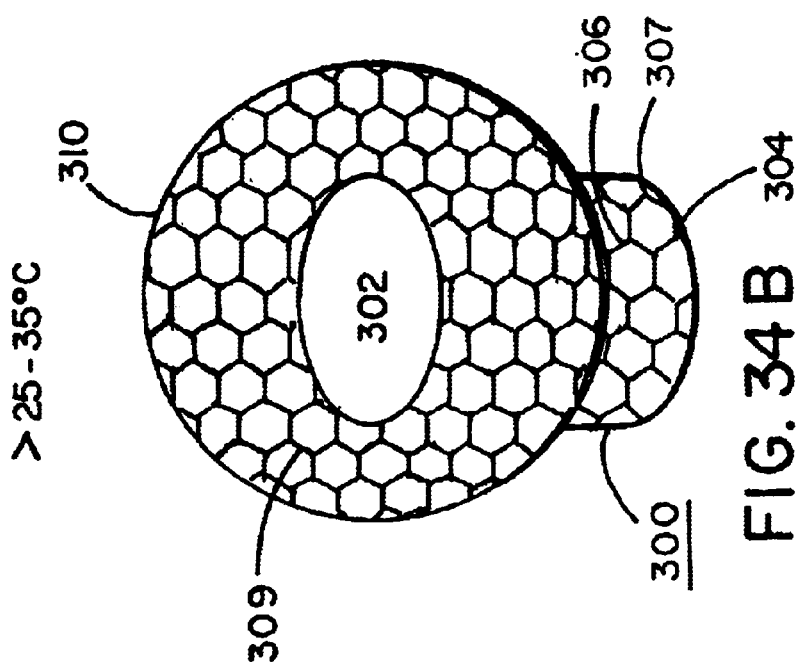
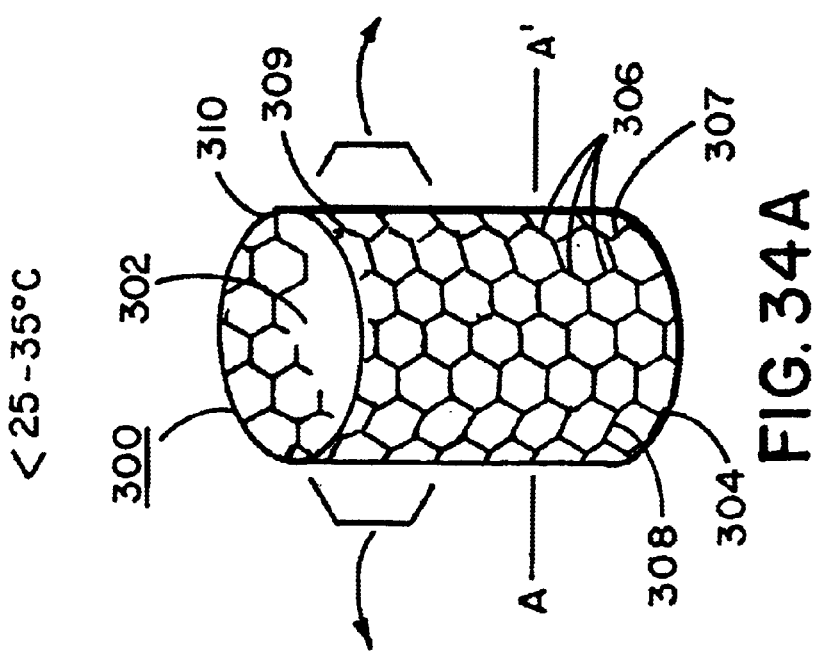
FIG. 34B
FIG. 34A

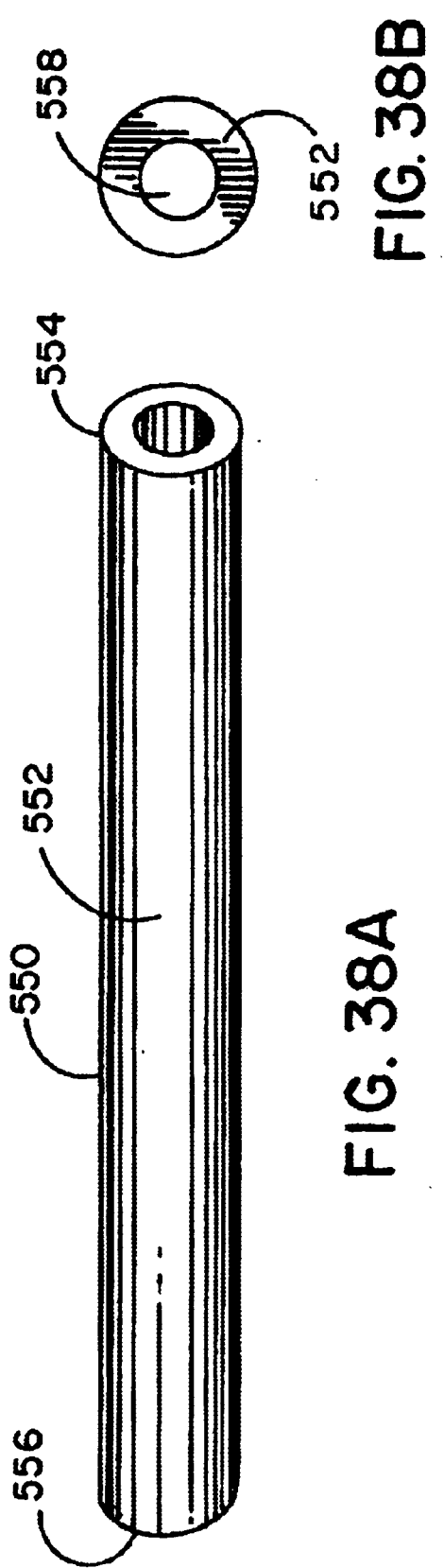

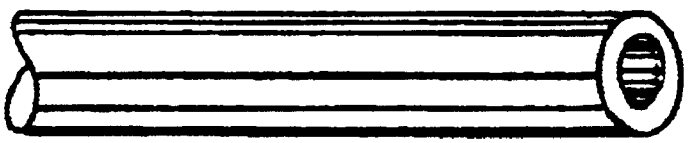 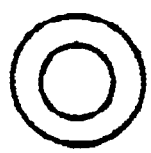
FIG. 40A          FIG. 40B
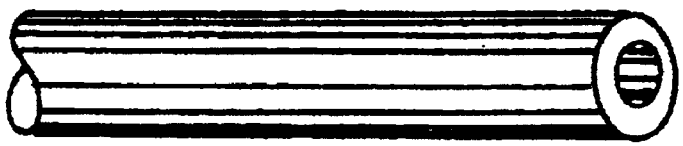 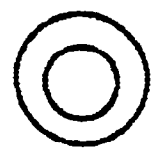
FIG. 41A          FIG. 41B
 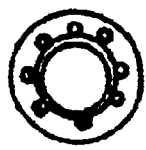
FIG. 42A          FIG. 42B
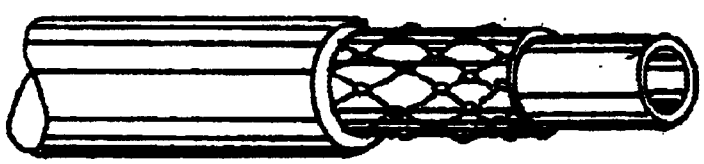 
FIG. 43A          FIG. 43B

DEVICES, SYSTEMS AND METHODS FOR CREATING SUTURELESS ON-DEMAND VASCULAR ANASTOMOSES AND HOLLOW ORGAN COMMUNICATION CHANNELS

PROVISIONAL PATENT APPLICATION

This invention was first filed as a Provisional Patent Application on Dec. 9, 1999 as U.S. application Ser. No. 60/169,874.

FIELD OF THE INVENTION

The present invention is concerned generally with minimally invasive methods for accessing the vascular system and hollow organs of the body; and is directed to an assembly and methodology for creating sutureless vascular anastomoses and hollow organ communication channels on-demand.

BACKGROUND OF THE INVENTION

Coronary artery disease is the single leading cause of human mortality and is annually responsible for over 900,000 deaths in the United States alone. Additionally, over 3 million Americans suffer chest pain (angina pectoris) because of it. Typically, the coronary artery becomes narrowed over time by the build up of fat, cholesterol and blood clots. This narrowing of the artery is called arteriosclerosis; and this condition slows the blood flow to the heart muscle (myocardium) and leads to angina pectoris due to a lack of nutrients and adequate oxygen supply. Sometimes it can also completely stop the blood flow to the heart causing permanent damage to the myocardium, the so-called "heart attack."

The conventional treatment procedures for coronary artery disease vary with the severity of the condition. If the coronary artery disease is mild, it is first treated with diet and exercise. If this first course of treatment is not effective, then the condition is treated with medications. However, even with medications, if chest pain persists (which is usually secondary to development of serious coronary artery disease), the condition is often treated with invasive procedures to improve blood flow to the heart. Currently, there are several types of invasive procedures: (1) Catheterization techniques by which cardiologists use balloon catheters, atherectomy devices or stents to reopen up the blockage of coronary arteries; or (2) Surgical bypass techniques by which surgeons surgically place a graft obtained from a section of artery or vein removed from other parts of the body to bypass the blockage.

Conventionally, before the invasive procedures are begun, coronary artery angiography is usually performed to evaluate the extent and severity of the coronary artery blockages. Cardiologists or radiologists thread a thin catheter through an artery in the leg or arm to engage the coronary arteries. X-ray dye (contrast medium) is then injected into the coronary artery through a portal in the catheter, which makes the coronary arteries visible under X-ray, so that the position and size of the blockages in the coronary arteries can be identified. Each year in U.S.A., more than one million individuals with angina pectoris or heart attack undergo coronary angiographies for evaluation of such coronary artery blockages. Once the blocked arteries are identified, the physician and surgeons then decide upon the best method to treat them.

In the surgical correction of vascular disease in the human body, it is frequently necessary to attach blood vessels to each other. A native blood vessel may be diseased with conditions that cause blockages, such as atherosclerosis. In this situation, it is frequently necessary to reroute the blood that would ordinarily traverse the diseased vessel via the creation of a vascular bypass. The conduit used to form this bypass around an obstructed segment may be another blood vessel native to the patient, such as a vein or artery harvested from elsewhere in the body; or may be a man-made conduit of either synthetic or biological material. Methods for attaching blood vessels to each other include: end to end attachments, where the result is a linear conduit for blood flow with the bypassing vessel and the vessel to which it is attached lying in parallel, in-line with each other; side to side attachments, where the result is a staggered, linear channel, where the bypassing vessel and the vessel to which it is attached are in parallel but offset by the width of one of the blood vessels; and end to side attachments, where the bypassing vessel meets the vessel which it is to supply with flow at some angle of less than 180 degrees, and typically approximately 90 degrees and often as a 'T' or 'L' or 'H' type of connection.

It is useful here to understand in depth what the traditional coronary arterial bypass entails and demands both for the patient and for the cardiac surgeon. In a standard coronary bypass operation, the surgeon must first make a foot-long incision in the chest and split the breast bone of the patient. The operation requires the use of a heart-lung machine that keeps the blood circulating while the heart is being stopped and the surgeon places and attaches the bypass grafts. To stop the heart, the coronary arteries also have to be perfused with a cold potassium solution (cardioplegia). In addition, the body temperature of the patient is lowered by cooling the blood as it circulates through the heart-lung machine in order to preserve the heart and other vital organs. Then, as the heart is stopped and a heart-lung machine pumps oxygenated blood through the patient's body, the surgeon makes a tiny opening into the front wall of the target coronary artery with a very fine knife (arteriotomy); takes a previously excised saphenous vein (a vein from a leg) or an internal mammary artery (an artery from the chest); and sews the previously excised blood vessel to the coronary artery. Synthetic substitutes for a naturally occurring blood vessel are available and often used.

To create the anastomosis at the aorta, the ascending thoracic aorta is first partially clamped using a curved vascular clamp to occlude the proper segment of the ascending aorta; and a hole is then created through the front wall of the aorta to anchor the vein graft (or synthetic substitute) with sutures. The graft bypasses the blockage in the coronary artery and restores adequate blood flow to the heart. After completion of the grafting, the patient is taken off of the heart-lung machine and the patient's heart starts beating again. Most of the patients can leave the hospital in about 6 days after the surgical procedure.

It will be noted that coronary artery bypass surgery is considered a definitive method for treating coronary arterial disease because all kinds of obstructions cannot be treated by angioplasty; and because a recurrence of blockages in the coronary arteries even after angioplasty is not unusual. Also coronary artery bypass surgery usually provides for a longer patency of the grafts and the bypassed coronary arteries in comparison with the results of an angioplasty procedure. However, traditional coronary artery bypass surgery is a far more complicated procedure, having need of a heart-lung machine and a stoppage of the heart. Also, it is a more invasive procedure and is more expensive to perform. Therefore, cardiac surgeons have recently developed an alternative to the standard bypass surgery, namely "minimally invasive bypass operation" (MIBO) in order to reduce the risks and the cost associated with the surgery. Also, the MIBO is performed without use of a heart-lung machine or the stopping of the heart. Some of the current methods for creating these connections include handsewn surgical anastomoses, where a surgeon places a series of surgical knots around the circumference of the vascular connection, forming a liquid-tight connection; as well as a variety of vascular staple type devices, where mechanical apparatii are used to effect the connection, generally using a two or more part apparatus comprising the staple introducer and an 'anvil' type of part against which the staples are curved back, bent, or otherwise fixed into position around the circumference of the vascular connection.

Another approach has been the introducer catheter based methods and apparatii for the creation of an end-to-side vascular connection (anastomosis) using an implanted device comprising a deformable flange or retained portion and deformable flange, to which a biological or synthetic conduit has been pre-attached ex-vivo; and a variety of configurations for introducer mechanisms and systems for, inserting this implantable device into the side of the blood vessel. For the purposes of this description, the blood vessel is generally defined as the blood vessel which is punctured and which receives the collar or deformable flange portion of the implantable device into its internal lumen. The receiving blood vessel may be either the source or the recipient of blood flow, depending on the required and existing direction of blood flow. Merely illustrative and representative of these introducer catheter based vascular bypass graft systems and techniques are U.S. Pat. Nos. 6,007,544; 5,797,920, and 5,676,670 all of which describe a catheter apparatus and methods for creating a bypass on-demand between an unobstructed and obstructed blood vessel using a deformable cuff connector and graft segment in tandem; as well as U.S. Pat. Nos. 6,036,702; 6,013,190; 6,001,124; 5,972,017; 5,941,908; and 5,931,842 which illustrate a range and variety of T-shaped, L-shaped, H-shaped, and oblique-angle graft connectors available for medical use.

A key advantage of the methods and devices described in these issued U.S. Patents is the ability to create a vascular anastomosis while maintaining high blood pressures (systemic and greater) within the receiving blood vessels. These devices and systems therefore allow the creation of the proximal anastomosis in Coronary Artery Bypass Grafting procedures (CABG) to be performed without need to exclude blood from the aorta where the site of anastomosis is to be. This in turn obviates the need for use of the cardiopulmonary bypass machine, a device (which takes over the pumping of the blood through the body while the proximal aorta is made blood pressure free); and eliminates the Aortic Side Biting Clamp, a semicircular clamp which pinches off a portion of the aorta, creating a blood pressure free pocket to which the handsewn graft attachment was previously made. Use of both the machine and the side biting clamp result in trauma to the aorta; and such trauma causes, among other things, the release of embolic debris from the aortic wall (a cause of stroke, cognitive deterioration, and other morbidities), and/or damage to the lining of the aorta which can result in separation of the layers of the aorta, resulting in dissection, a potentially lethal complication. Frequently also, the time required for surgery is shortened because intricate in-vivo suturing techniques are not required to ensure acceptable patency rates and no leakage at the handsewn anastomoses of the new grafts.

There remains, however, a long-standing and continuing need for additional improvements in bypass technique and apparatus which would allow surgeons to perform more simple multiple bypass procedures in a minimally invasive way using tubular grafts as vascular shunts; and, in particular, a need remains for a catheterless method to place one or more vein grafts or other conduits proximally to the aorta and distally to the coronary artery without using a heart-lung machine, and without stopping the heart, and without using the side biting clamp.

In addition to the foregoing difficulties, there exists also a very different medical problem in the non-vascular realm, in particular with regard to obtaining in-vivo access to a hollow organ within the body of a living subject.

Access to the interior of a hollow organ is often needed for a number of reasons, depending on the organ system. These accesses may be required to supply food substances into the stomach or small bowel in patients who are unable to eat (gastrostomy and jejunostomy, respectively); and/or to eliminate wastes or the buildup of pressure in other organs whose outlets are blocked or dysfunctional, as may occur in the obstructed urinary system (nephrostomy or cystostomy), respiratory system (tracheostomy), or the pathologically dilated cecum (proximal large bowel and cecostomy). Occasionally, a hollow organ space or body cavity is filled with infected material, and it is clinically desirable to create a communication channel allowing the infected contents to be drained rather than surgically removing the infected organ. Such a situation may occur within the gallbladder, and the communication channel so created is then called a cholecystostomy. Occasionally, a communication channel is required between hollow body cavities, such as between a cyst originating in the pancreas, and the inside of the stomach. Periodically as well, a communication channel is required into a spatial area or zone within the body, such as the peritoneal cavity, in order to instill fluids for dialysis. Thus, a number of different devices and systems now exist for the on-demand creation of these types of communication channels between hollow organs; or between body cavities and the skin surface; or between two hollow organs within the body.

It will be noted that many hollow organ surgical procedures are now performed using trocars and cannulas. Originally these devices were used for making a puncture and leaving a tube to drain fluids. As technology and surgical techniques advanced, it became possible to insert surgical instruments through the cannulas to perform invasive procedures through openings less than half an inch in diameter, whereas in the past these procedures required incisions of many inches. By using a trocar and minimizing the incision, the stress and loss of blood suffered by patients was reduced. A range and variety of trocar assemblies are known. These are represented by U.S. Pat. Nos. 4,601,710; 5,545,150; 5,122,122; 5,112,321; and 6,063,099.

Today, surgical trocars are most commonly used in laparoscopic surgery. Prior to use of the trocar, the surgeon will usually introduce a Veress needle into the patient's abdominal cavity. The Veress needle has a stylet which permits the introduction of gas into the abdominal cavity. After the Veress needle is properly inserted, it is connected to a gas source and the abdominal cavity is insufflated to an approximate abdominal pressure of 15 mm Hg. By insufflating the abdominal cavity, pneumoperitoneum is created separating the wall of the body cavity from the internal organs.

A trocar is then typically used to puncture the body cavity. The piercing tip or obturator of the trocar is inserted through the cannula; and the cannula partially enters the body cavity through the incision made by the trocar. The obturator is then removed from the cannula. An elongated endoscope or camera may be then inserted through the cannula to view the body cavity; or surgical instruments may be inserted through the cannula to perform ligations or other procedures.

A great deal of force is often required to cause the obturator to pierce the wall of the body cavity. When the piercing tip breaks through the cavity wall, resistance to penetration ceases and the tip may reach internal organs or blood vessels, with resultant lacerations and potentially serious injury. For this reason, a variety of trocar designs have been developed with spring loaded shields surrounding the piercing tip of the obturator. Once the piercing tip of the obturator has completely pierced the body cavity wall, the resistance of the tissue to the spring loaded shield is reduced and the shield springs forward into the body cavity and covers the piercing tip. The shield thereby protects internal body organs and blood vessels from incidental contact with the piercing tip and resultant injury. Such trocars including various safety shield designs are illustrated by U.S. Pat. Nos. 4,535,773; 4,654,030; and 4,601,710; 5,104,382; 4,902,280; 5,030,206; 5,545,150; and 5,350,393.

Clearly both the realms of performing vascular bypass graft procedures and accessing the interior of a hollow organ can and would benefit from structural devices and improved surgical methods which offer simplified means for joining a prepared communication channel to a blood vessel or a hollow organ on-demand in a minimally invasive way. Moreover, were such simplified means developed such that the presently existing requirement and necessity of using a catheter or cannula is eliminated and avoided, such an improvement would be generally recognized in the medical arts as a major advance and unusual benefit to both the surgeon and his patient.

SUMMARY OF THE INVENTION

The present invention has multiple formats and applications. A first format is a catheterless, piercing introducer assembly suitable for the introduction and sutureless juncture of a prepared communication channel to the interior space of an anatomic body part within a living subject, said introducer assembly comprising:
  a perforator instrument comprised of
    (i) at least one elongated supporting shaft of predetermined overall dimensions and axial configuration,
    (ii) a controlling handle attached at one end to said supporting shaft; and
    (iii) a perforating headpiece integrally joined to the other end of said supporting shaft, said perforating headpiece comprising a perforating tip, a penetrating body, and a base aspect; and
  communication channel controlling means disposed adjacent to said perforating headpiece on said supporting shaft of said perforator instrument.

A second format is a catheterless, piercing introducer assembly suitable for the introduction and sutureless juncture of a prepared communication channel to the interior space of an anatomic body part within a living subject, said introducer assembly comprising:
  a perforator instrument comprised of
    (i) at least one elongated supporting shaft of predetermined overall dimensions and axial configuration.
    (ii) a controlling handle attached at one end to said supporting shaft; and
    (iii) a perforating headpiece integrally joined to the other end of said supporting shaft, said perforating headpiece comprising a perforating tip; a penetrating body, and a base aspect.
  communication channel controlling means disposed adjacent to said perforating headpiece on said supporting shaft of said perforator instrument;
  a volumetric sheath having two open ends and at least one sidewall of determinable dimensions, said sheath being
    (1) sized at one open end for on-demand placement adjacent to and aligned closure with said perforating headpiece of said perforator instrument,
    (2) substantially annular in configuration over its axial length, and
    (3) adapted for protective positioning around and volumetric spatial envelopment of at least a portion of said supporting shaft extending from said perforating headpiece of said perforator instrument, said sheath providing a protective covering for said enveloped spatial volume then surrounding said supporting shaft; and
  position holding means attachable to and detachable from said volumetric sheath and said supporting shaft of said perforator instrument for holding said volumetric sheath and the enveloped spatial volume at a set position around said supporting shaft of said perforator instrument.

A third format of the present invention is a catheterless, piercing introducer assembly suitable for the introduction and sutureless juncture of a prepared communication channel to the interior space of an anatomic body part within a living subject, said introducer assembly comprising:
  a perforator instrument comprised of
    (i) at least one elongated supporting shaft of predetermined overall dimensions and axial configuration
    (ii) a controlling handle attached at one end to said supporting shaft; and
    (iii) a perforating headpiece integrally joined to the other end of said supporting shaft, said perforating headpiece comprising a perforating tip, a penetrating body, and a base aspect;
  communication channel controlling means disposed adjacent to said perforating headpiece on said supporting shaft of said perforator instrument;
  a volumetric sheath having two open ends and at least one sidewall of determinable dimensions, said sheath being
    (1) sized at one open end for on-demand placement adjacent to and aligned closure with said perforating headpiece of said perforator instrument,
    (2) substantially annular in configuration over its axial length, and
    (3); adapted for protective positioning around and volumetric spatial envelopment of at least a portion of said supporting shaft extending from said perforating headpiece of said perforator instrument, said sheath providing a protective covering for said enveloped spatial volume then surrounding said supporting shaft;
  position holding means attachable to and detachable from said volumetric sheath and said supporting shaft of said perforator instrument for holding said volumetric sheath and the enveloped spatial volume at a set position around said supporting shaft of said perforator instrument; and
  prepared communication channel comprising
    a linking connector including at least
      a first portion of determined dimensions and configuration which is deformable on-demand, said first portion of said linking connector being suitable for passage through an aperture and deformation within the interior space of an anatomic body part whereby said deformation serves to secure said communication channel to the interior of the anatomic body part and places said secured communication channel in fluid flow communication with the interior space of the anatomic body part, and a second portion of determined dimensions and configuration which is permanently joined to the sidewall of a tubular conduit such that said joining retains and secures the tubular conduit for fluid flow communication; and a tubular conduit of fixed dimensions and configuration having two open ends and at least one internal lumen, said tubular conduit being permanently joined at one open end to said linking connector.

BRIEF DESCRIPTION OF THE FIGURES

The present invention may be better appreciated and more easily understood when taken in conjunction with the accompanying drawing, in which:

FIG. 1 is a perspective illustration of a first preferred embodiment of the introducer assembly comprising the present invention;

FIGS. 2A and 2B are illustrations of the perforator instrument comprising a component part of the introducer assembly of FIG. 1;

FIGS. 3A and 3B are illustrations of the volumetric sheath comprising a component part of the introducer assembly of FIG. 1;

FIGS. 6A, 6B, and 6C are illustrations of a linking connector and tubular conduit which comprise a prepared communication channel to be used with the introducer assembly of FIG. 1;

FIGS. 8A and 8B are perspective and partial cross-sectional illustrations of the prepared communication channel of FIGS. 6B and 6C when positioned within and part of the complete introducer assembly of FIG. 1;

FIGS. 17A and 17B are cross-sectional and perspective illustrations of the perforating headpiece of FIG. 16;

FIG. 18 is an illustration of one alternative embodiment for the volumetric sheath of FIG. 3;

FIG. 19 is an illustration of the relationship between the prepared communication channel of FIG. 6C when used in the perforating headpiece of FIGS. 16 and 17 and the volumetric sheath of FIG. 18;

FIG. 20 is an illustration of a second alternative embodiment for the volumetric sheath of FIG. 3;

FIG. 21 is an illustration of one alternative embodiment of the introducer assembly of FIG. 1;

FIG. 22 is a detail partial cross-sectional illustration of the alternative introducer assembly of FIG. 21;

FIG. 23 is a perspective illustration of a second preferred embodiment of the introducer assembly comprising the present invention;

FIG. 24 is an illustration of the perforator instrument comprising a component part of the introducer assembly of FIG. 23;

FIG. 26 is an illustration showing details of the perforating headpiece in the perforator instrument of FIG. 24;

FIG. 27 is an illustration of the volumetric sheath comprising a component part of the introducer assembly of FIG. 23;

FIGS. 28A and 28B are illustrations of the communication channel controlling means comprising part of the introducer assembly of FIG. 23;

FIG. 33 is an illustration of the secured communication channel after the introducer assembly of FIG. 23 has been removed;

FIGS. 34A and 34B are illustrations of a first linking connector;

FIGS. 38A and 38B are illustrations of an unbranched tubular conduit;

FIGS. 40A and 40B are illustrations of a first type of tubular conduit construction;

FIGS. 41A and 41B are illustrations of a second type of tubular conduit construction;

FIGS. 42A and 42B are illustrations of a third type of tubular conduit construction;

FIGS. 43A and 43B are illustrations of a fourth type of tubular conduit construction;

DETAILED DESCRIPTION OF THE INVENTION

Figure 4A:
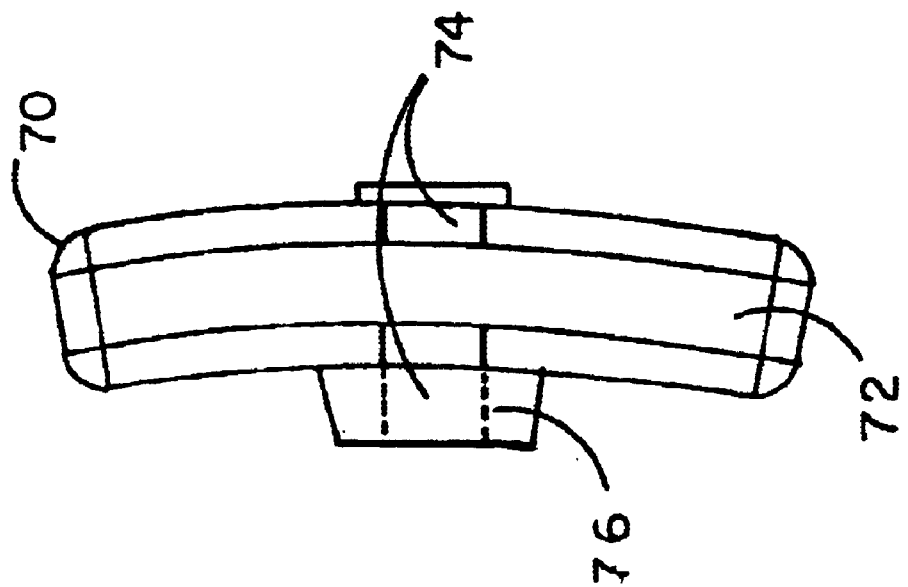
FIGS. 4A and 4B are illustrations of the position holding means comprising a component part of the introducer assembly of FIG. 1.

The present invention is an introducer assembly and surgical technique for creating a single channel bypass or multiple channel bypasses on-demand between blood vessels such as the aorta and an obstructed coronary artery in-vivo; and for creating an access channel or duct to the interior space of a hollow organ in-vivo. The present invention can utilize a synthetic tubular conduit as a communication channel; or a previously excised vascular segment as a grafted tubular conduit; or any other biological conduit created via hormonally or genetically modified cellular means. In addition, the invention employs a catheterless introducer assembly and system in combination with the prepared communication channel to create single or multiple conduit shunts or grafts in-vivo. The grafted tubular conduit will then be used either to deliver blood from a primary blood vessel, around the obstruction, into a secondary artery or vein in order to increase and/or maintain proper blood circulation in the living body; or provide an access duct or portal into a hollow organ in the body of a living subject. A number of substantial advantages and major benefits are therefore provided by the present invention, some of which include the following:

1. The present invention provides the means for surgeons to perform single or multiple channel grafts in a minimally invasive manner. The methodology permits the surgeon to utilize either synthetic tubular conduits as communication channels or previously excised veins or arteries or other biological conduit as bypass grafts; and allows the surgeon to place each of the tubular conduits from a primary unobstructed artery (such as the aorta) to a secondary obstructed artery (such as the obstructed coronary artery) without using a heart-lung machine and without need for stopping the heart during the surgery.

2. The present methodology also avoids the prior need to exclude blood from the section of the primary vessel to which the graft is being attached. In the case of CABG surgery, for example, there would be no further need for an aortic side biting clamp—a device with rough semi-circular jaws that isolates a centrally located zone of the aorta from the blood and blood pressure then present in the rest of the aorta.

3. The present invention simplifies the complexity of conventional vascular bypass or hollow organ surgery and makes the surgery less invasive. Moreover, the introducer assembly and technique provides the ability to create multiple communication channels using a sutureless and catheterless procedure which not only shortens the conventional operation time for surgery but also makes the surgery safer and more cost effective.

4. The present invention is suitable for creating a single conduit graft or multiple conduit grafts in any medical situation, condition, or pathology in which there is a need for to direct blood flow to a specific blood vessel or vascular area or body region. The cause or source of the medical problem may be an obstruction in a blood vessel; or a narrowing or thickening of a blood vessel wall; or a diminution or narrowing of a vascular section in a particular blood vessel. Each of these medical conditions has its particular cause, origin, or source; and each of these pathologies, though different in origin, causes a similar effect overall—a loss of blood flow and blood pressure within the blood vessel. Accordingly, the present invention is deemed useful and desirable to overcome any of these particular medical conditions and instances where there is a demonstrated need for increased blood pressure and blood volume flow within a particular blood vessel in the body, and where that blood may be supplied from a suitable adjacent vessel using the present system.

5. The present apparatus and methodology can be employed to create a bypass conduit between any two blood vessels. In many instances, the bypass conduit will be made between a primary unobstructed artery and a secondary obstructed artery, a typical example being a bypass between the ascending aorta and an obstructed coronary artery. However, a bypass shunt may also be created between any two veins (such as between the portal vein and the inferior vena cava); or between an artery and a vein (such as between the superior vena cava and a pulmonary artery) between the different chambers of the heart, or between the heart chambers and blood vessels. Equally important, although the primary focus of the present invention is the thoracic cavity and the recognized need for bypass conduits among the blood vessels found therein, the present apparatus and methodology may be employed anywhere in the human body where there is a need for increased vascularization or revascularization of the local region. The sole limitation, therefore, is a means of access for the catheter apparatus, the introducer system, and the methodology to be performed by the skilled surgeon, or interventional radiologist, or other medical specialist.

6. The introducer assembly and method of use provides on-demand duct access to the interior of a hollow organ in a variety of applications. These grafted ducts provide access to supply food substances into the stomach or small bowel in patients who are unable to eat (gastrostomy and jejunostomy, respectively); and/or as a channel to eliminate wastes or the buildup of pressure in other organs whose outlets are blocked or dysfunctional, as may occur in the obstructed urinary system, respiratory system, or the pathologically dilated. Also, when a hollow organ or cavity is filled with infected material, the introducer system creates a communication channel for egress, thereby allowing the infected contents to be drained rather than surgically removing the infected organ or cavity. Such a situation typically occurs within the gallbladder and the communication channel so created is then called a cholecystostomy. In addition, the system will provide a communication channel between hollow body cavities, such as between a cyst originating in the pancreas, and the inside of the stomach or between ventricles of brain and peritoneum or vascular system; and when a communication channel is required to be placed into a spatial area or zone within the body, such as the peritoneal cavity, in order to instill fluids for dialysis.

In order to better appreciate and more clearly understand the introducer assembly and the system of intended usage, the invention as a whole will be described as first and second preferred embodiments which describe both the requisite and optional component parts and subassemblies in detail; and also present a series of alternative embodiments and features which can be optionally employed at will in addition to or in place of pertinent parts in either of the preferred embodiments described herein.

I. A First Preferred Embodiment

A first preferred format and embodiment of the introducer assembly is exemplified and illustrated by FIGS. 1–14 respectively. As shown therein, FIGS. 1–8 identify the preferred introducer assembly in its minimal and optional component parts; while FIGS. 9–14 respectively illustrate the intended method of usage and system which uses the introducer assembly to achieve a sutureless juncture of a prepared communication channel to a blood vessel or to the interior of a hollow organ.

The introducer assembly as a whole is illustrated by FIGS. 1 and 2. As seen therein, the optimized introducer assembly is comprised of a perforator instrument 10; and the communication channel controlling means 40 which appears as an inflatable and deflatable on-demand balloon appliance in this preferred embodiment; a volumetric sheath 50; and sheath position holding means which appear in this preferred embodiment as the grasping member 70. The introducer assembly exemplified by FIG. 1 is in completely assembled form; comprises each of the requisite and optional component parts and sub-assemblies in its appropriate placement and position; and shows the entire optimized apparatus in a state ready for immediate usage. Details of the individual component parts of the introducer assembly are shown by FIGS. 2–8 respectively.

FIG. 2 shows the minimal introducer assembly in detail which comprises only the perforator instrument 10 and the balloon appliance 40 which serves as one specific means for controlling and deploying a prepared communication channel. As illustrated by FIGS. 2A and 2B, the perforator instrument 10 of the minimalist introducer assembly is comprised of at least one elongated supporting shaft 12 of predetermined overall dimensions and axial length having two ends 14, 16; and has a internal lumen 18. Knob handle 15 is attached at the end 16 of the supporting shaft 12; and a perforating headpiece 30 is joined to the supporting shaft at the other shaft end 14. The perforating headpiece 30 is integrally joined to the end 14 of the supporting shaft 12 and itself comprises a perforating tip 32, a penetrating body 34, and a base aspect 36.

The perforator instrument 10 is thus itself an assembly of parts which provides a knob handle for the surgeon and a cutting headpiece suitable for penetrating the sidewall tissue of a blood vessel or hollow organ and forming an aperture in-situ.

Disposed adjacent to the perforating headpiece 30 on the supporting shaft 12 of the perforator instrument 10 is an inflatable and deflatable on-demand balloon appliance 40. In this minimalist format and first preferred embodiment, the balloon appliance 40 structurally serves as communication channel controlling means for the deployment of the introducer assembly as a whole; and provides the primary apparatus for controlling the positioning of a previously prepared communication channel which, after proper placement within the assembly, will serve either as a vascular bypass graft or an access duct in-vivo.

The balloon appliance 40—the communication channel controlling means in this embodiment—is comprised of an expandable and deflatable balloon 42 whose interior volumetric space can be increased and decreased on demand repeatedly without difficulty; an inflation line 44 joined to the interior space of the balloon 42; and a luer lock fitting 48 joined to the inflation line 44 but positioned adjacent to the knob handle 15. The luer lock fitting 48 provides the direct communication means for introducing a inflation fluid from an external source (not shown) into the inflation line 44 through which the inflation fluid will be carried and transported into the interior volumetric space of the balloon 42. By adding fluid through or allowing fluid to flow out of the luer lock fitting 48, the degree of inflation or deflation for the balloon appliance 40 can be controlled and maintained at will.

The volumetric sheath 50, an optional but highly desirable structure of the introducer assembly, is illustrated by FIGS. 3A and 3B respectively. The optional volumetric sheath 50 has two open ends 52, 54 and at least one sidewall 56 of predetermined dimensions. The volumetric sheath 50 is sized at the open end 52 for on-demand placement adjacent to and aligned closure with the perforating headpiece 30 of the perforator instrument 10. In addition, the optional volumetric sheath 50 is substantially annular in configuration over its axial length but is desirably constricted at the open end 52 to conform to the particular dimensions of the perforating headpiece 30. The essential purpose and function of the volumetric sheath 50 is protection such that its internal spatial volume 58 over its axial length becomes available and adapted for protective positioning around and volumetric spatial envelopment of at least a portion of the supporting shaft 12 which extends from the perforating headpiece 30 of the perforator instrument 10.

As shown in FIG. 1 previously, the optional volumetric sheath 50 when properly positioned provides a protective covering and envelope for the spatial volume and ambient environment then surrounding the supporting shaft 12; and any contents (including a prepared communication channel which is then positioned within the internal spatial volume 58 of the volumetric sheath 50) will become protectively surrounded and enveloped by the sheath sidewall 56 over the entirety of the axial length for the configured volumetric sheath 50. For the introducer assembly as a whole, particularly as depicted by FIG. 1, the volumetric sheath 50 provides the protective envelopment of an ambient environment spatial volume and all its interior contents which then surround the supporting shaft 12 and the introducer assembly as an integrated unit.

Figure 4B:
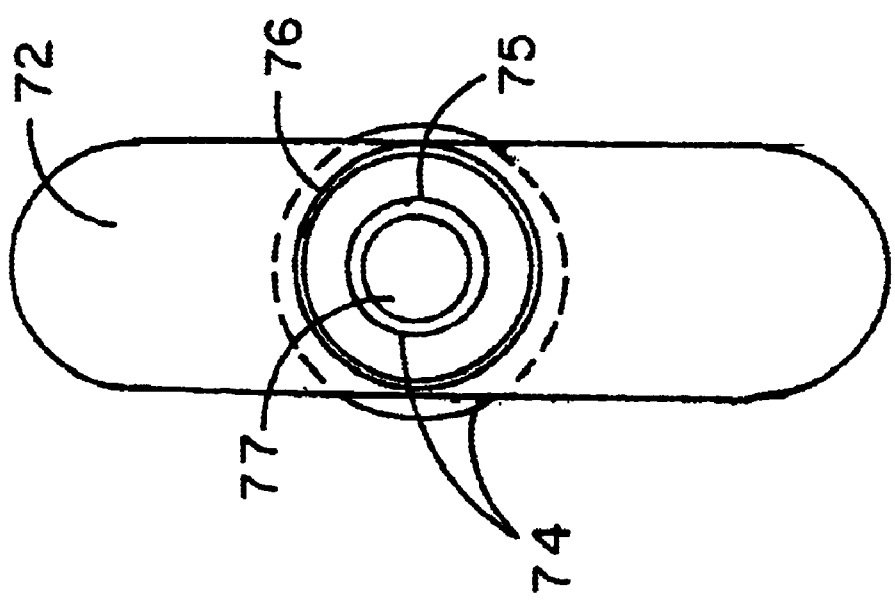
Figure 5:
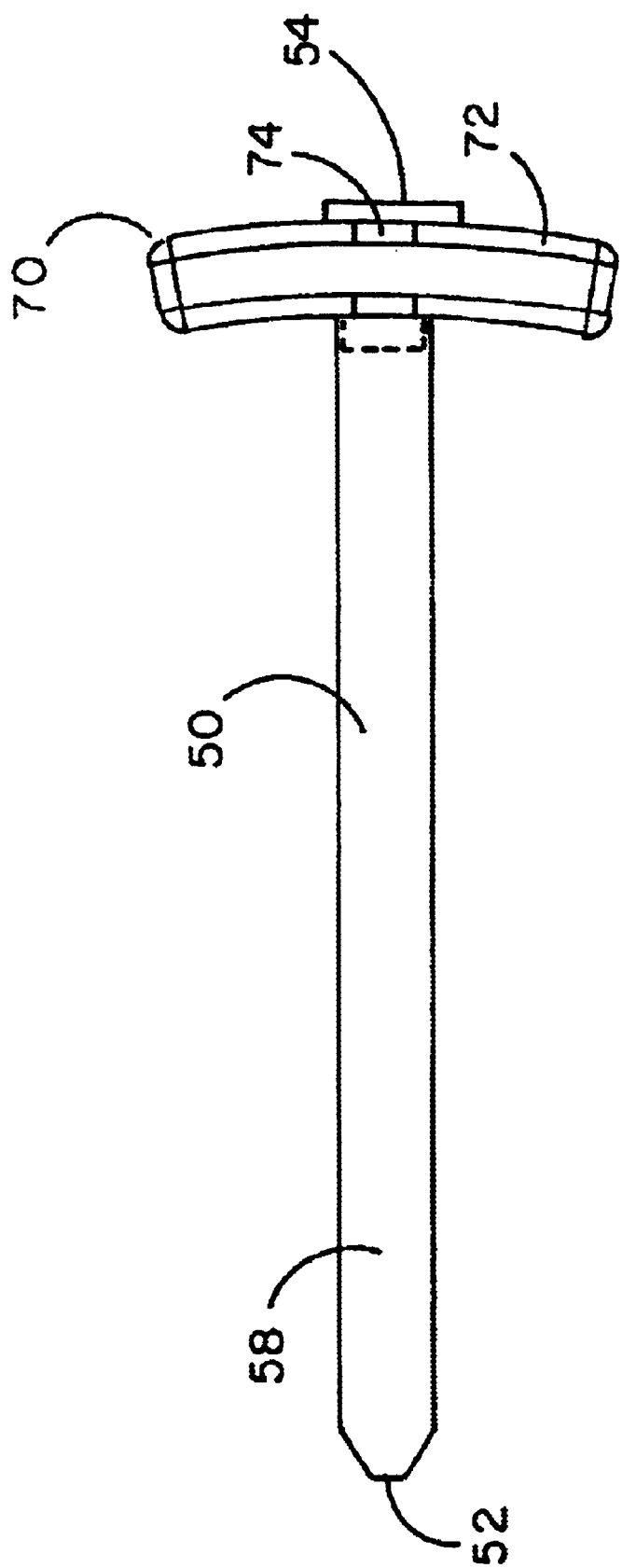
FIG. 5 is an illustration of the inter-relationship between the volumetric sheath of FIGS. 3A and 3B and the position holding means of FIGS. 4A and 4B.

The optional position holding means 70 and its intended function within the preferred introducer assembly is illustrated by FIGS. 4 and 5 respectively. FIGS. 4A and 4B each illustrate the grasping member 70 which is the specific embodiment of the optional position holding means in this assembly; while FIG. 5 shows the interrelationship between the grasping member 70 and the volumetric sheath 50 as intended by the assembly of parts.

As shown by FIGS. 4A and 4B, the grasping member 70 comprises a grip 72; a shaft mounting 74 configured for disposition around the support shaft 12 of the perforator instrument 10; and a sheath positional end fitting 76 which is annular or circular in overall configuration and dimensioned to fit snugly in a friction holding position with the open end 54 of the volumetric sheath 50. It will be noted and appreciated also that the shaft mounting 74 is itself substantially circular in configuration and is comprised of a flange 75 and a encircled aperture 77 through which the supporting shaft 12 will pass axially.

When properly aligned with the optional volumetric sheath 50, the overall result is illustrated by FIG. 5. Clearly, the open ends 52, 54 of the volumetric sheath 50 are in alignment with the grasping member 70; and the entire internal spatial volume 58 of the volumetric sheath 50 is encompassed by the attachment of the position holding grasping member 70 at the end 54. The grasping member thus provides position holding means and maintenance for the volumetric sheath within the introducer assembly over most of its axial length.

The arrangement of each of the requisite and optional component parts illustrated by FIGS. 2–5 is thus shown properly aligned and assembled as a preferred structural apparatus by FIG. 1. As the grasping member 70 is advanced forward or pulled rearward over the supporting shaft 12 of the perforating instrument 10, the volumetric sheath 50 will concomitantly be advanced forward or pulled rearward as a consequence. Thus, at any moment or instance of use, the volumetric sheath 50 as a whole and its internal spatial volume 58 as well as any contents to be found within the internal spatial volume itself can be advanced to and beyond the perforating headpiece 30 or pulled rearward to reveal the component parts of the perforator instrument. In this manner the perforating headpiece 30 can be alternatively and repeatedly exposed or hidden within the internal spatial volume 58 of the volumetric sheath 50.

The purpose and function of the introducer assembly is to provide for a catheterless and sutureless juncture of a prepared communication channel to the interior of a blood vessel or a hollow organ in-vivo. For descriptive purposes, the prepared communication channel is briefly illustrated by FIGS. 6A, 6B, and 6C which show the proper parts of a prepared communicating channel to be used within the introducer assembly. The essential parts are briefly illustrated by FIG. 6; but a far more detailed description of the major forms and alternative embodiments of communicating channels as a manufactured article are subsequently disclosed herein as well as illustrated by FIGS. 34–47 inclusive.

As shown by FIG. 6, a prepared communication channel 80 is comprised of a linking connector 82 and a tubular conduit 90. The tubular conduit 90 is any tube or hollow channel having two open discrete ends 92, 94; at least one tubular sidewall 96; and an internal lumen 98 of fixed spatial volume. The tubular conduit 90 accordingly also has an internal sidewall surface 95 which is co-extensive with the internal lumen 98; and an external sidewall surface 97 of predetermined dimensions and overall configuration. Further details regarding the tubular conduit 90 are described hereinafter.

The linking connector 82 is shown as an open wire meshwork construction in FIGS. 6B and 6C respectively. The linking connector includes at least a first cuff portion 84 of predetermined dimensions and configuration which is superelastic and/or thermo-elastic, thermo-plastic and deployable on-demand. The first cuff portion 84 is configured for passage through an aperture in the wall of a blood vessel or a hollow organ; is superelastic; and is deformable and deployable on-demand whereby the act of deformation in-situ within the interior volumetric space of a blood vessel or hollow organ serves to secure the joined tubular conduit interior of the blood vessel or hollow organ and places the secured tubular conduit in fluid flow communication with the interior volumetric space of the blood vessel or hollow organ proper. The linking connector also includes a second conduit retaining portion 86 of determined dimensions and configuration which is joined to the sidewall 96 of the tubular conduit 90 such that the joining retains and secures the tubular conduit 90 for fluid flow communication purposes.

The juncture of the linking connector 82 may be made either at the external sidewall surface 97 as shown in FIG. 6B or alternatively at the internal sidewall surface 95 as illustrated by FIG. 6C. In many instances the juncture of the second conduit retaining portion 86 is desirably done within the internal lumen 98 by direct joining to the internal sidewall surface 95. However, any format of juncture [using staples, sutures or any other permanent means for joining] is suitable for use within the introducer assembly. Accordingly, the prepared communication channel 80 as a prepared article of manufacture is shown equally by FIGS. 6B or 6C without distinction or meaningful difference.

For purposes of further description the communication channel 80 will be prepared in the manner illustrated by FIG. 6C where the linking connector 82 is joined along its retaining portion 86 to the internal sidewall surface 95 of the tubular conduit 90. The placement of the prepared communication channel as embodied by FIG. 6C is shown in FIG. 7.

Figure 7:
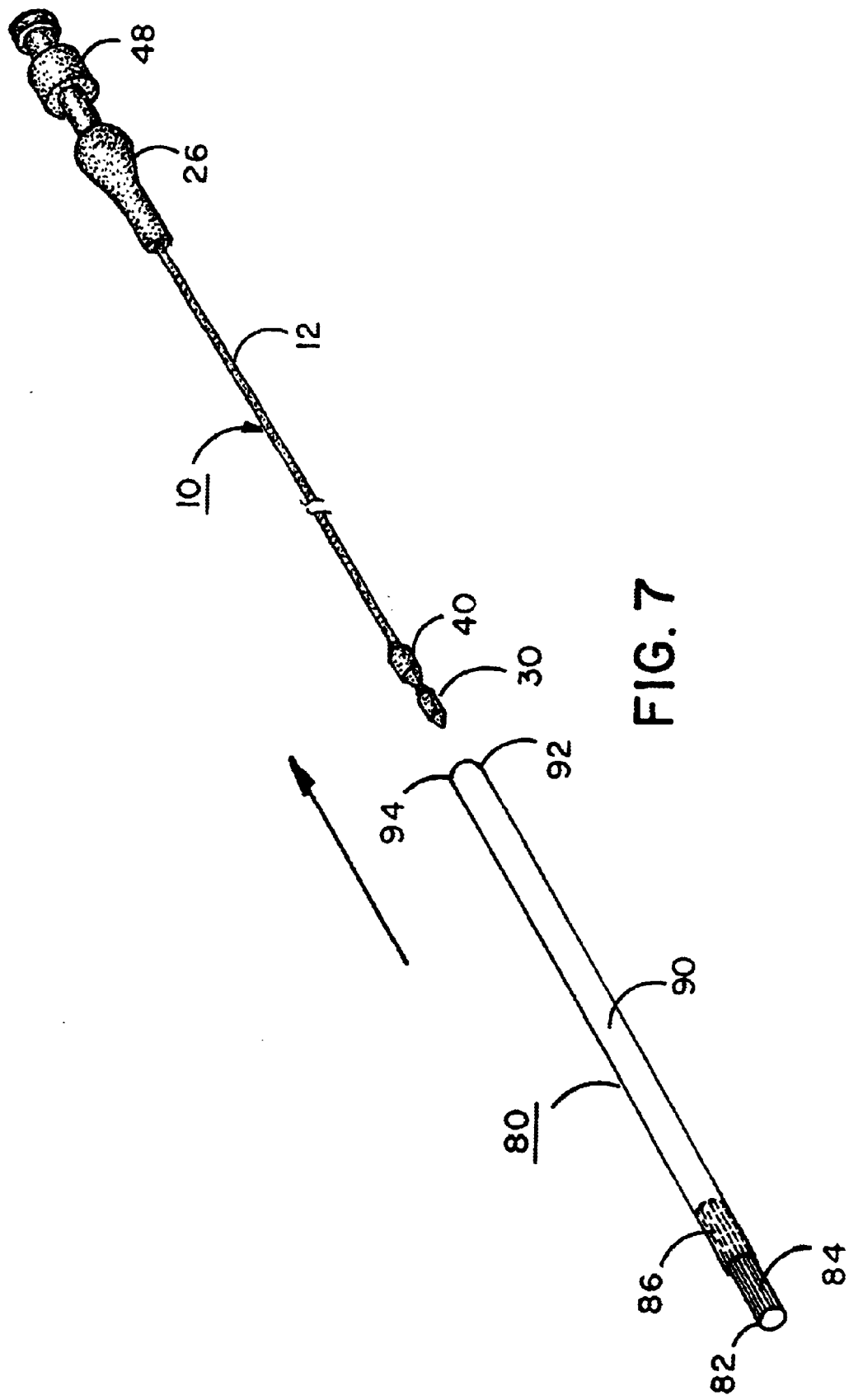
FIG. 7 is an illustration of the inter-relationship between the prepared communication channel of FIGS. 6B and 6C and the perforator instrument of FIGS. 2A and 2B.

As illustrated by FIG. 7, the prepared communication channel 80 is intended to be positioned over perforator instrument 10. This positioning is accomplished by inserting the perforating headpiece 30 and the supporting shaft 12 of the perforator instrument 10 into the internal lumen 98 of the tubular conduit 90 via the open end 94. The perforating headpiece 30 is then extended through the internal lumen 98 until it exits the communication channel 80 at the other tubular conduit end, thereby concomitantly also passing through the joined linking connector 82 in its entirety. Supporting shaft 12 will then hold and support the entirety of the prepared communication channel 80 in this position within the introducer assembly; and the volumetric sheath with grasping member 70 is subsequently placed around prepared communication channel 80. This results in the completely arranged introducer assembly illustrated by FIG. 8.

As seen therein, FIG. 8A shows a perspective view of the complete introducer assembly with the prepared communication channel 80 contained within the internal spatial volume 58 of the volumetric sheath 50. To illustrate better the aligned positioning within the introducer assembly, a cross sectional view along the axis AA' of FIG. 8A is provided and shown in detail via FIG. 8B. As seen therein, the prepared communication channel 80 is housed within the internal spatial volume 58 of the volumetric sheath 50; is completely enveloped by the volumetric sheath 50; and is protected by the covering of the volumetric sheath 50 while supported on the supporting shaft 12 of the perforator instrument 10. The first cuff portion 84 has been placed adjacent the penetrating body 34 of the perforating headpiece 30 while the second conduit retaining portion 86 joined to the internal sidewall surface 95 of the tubular conduit 90 appears positioned around the balloon appliance 40. As noted previously, the balloon appliance may be inflated and deflated at will; and by inflating the balloon appliance 40 in this setting, the inflated balloon will thus hold the entirety of the prepared communication channel 80 firmly and indefinitely and prevent the channel from moving linearly until such time that the balloon 40 is deflated again. Equally important, the entirety of the perforator instrument 10 including the perforating headpiece 30 may be advanced forward or pulled rearward at will at any time while positioned within the internal lumen 98 of the tubular conduit 90 and the joined linking connector 82. In this manner, the entire axial length of the perforator instrument may be advanced or withdrawn while the prepared communication channel 80 remains in a single position within the enveloped spatial volume 58 provided by the protective volumetric sheath 50. The complete introducer assembly illustrated by FIGS. 8A and 8B is shown in the intended application and usage for the introduction and sutureless juncture of a prepared communication channel by FIGS. 9–14 respectively. These FIGS. 9–14 inclusive illustrate that the anatomic body part penetrated is typically a blood vessel or a hollow organ 100. The targeteacody part 100 has at least two walls 102, 104 and an internal spatial organ volume 108. This is illustrated in its generic form within FIGS. 9–14.

Figure 9:
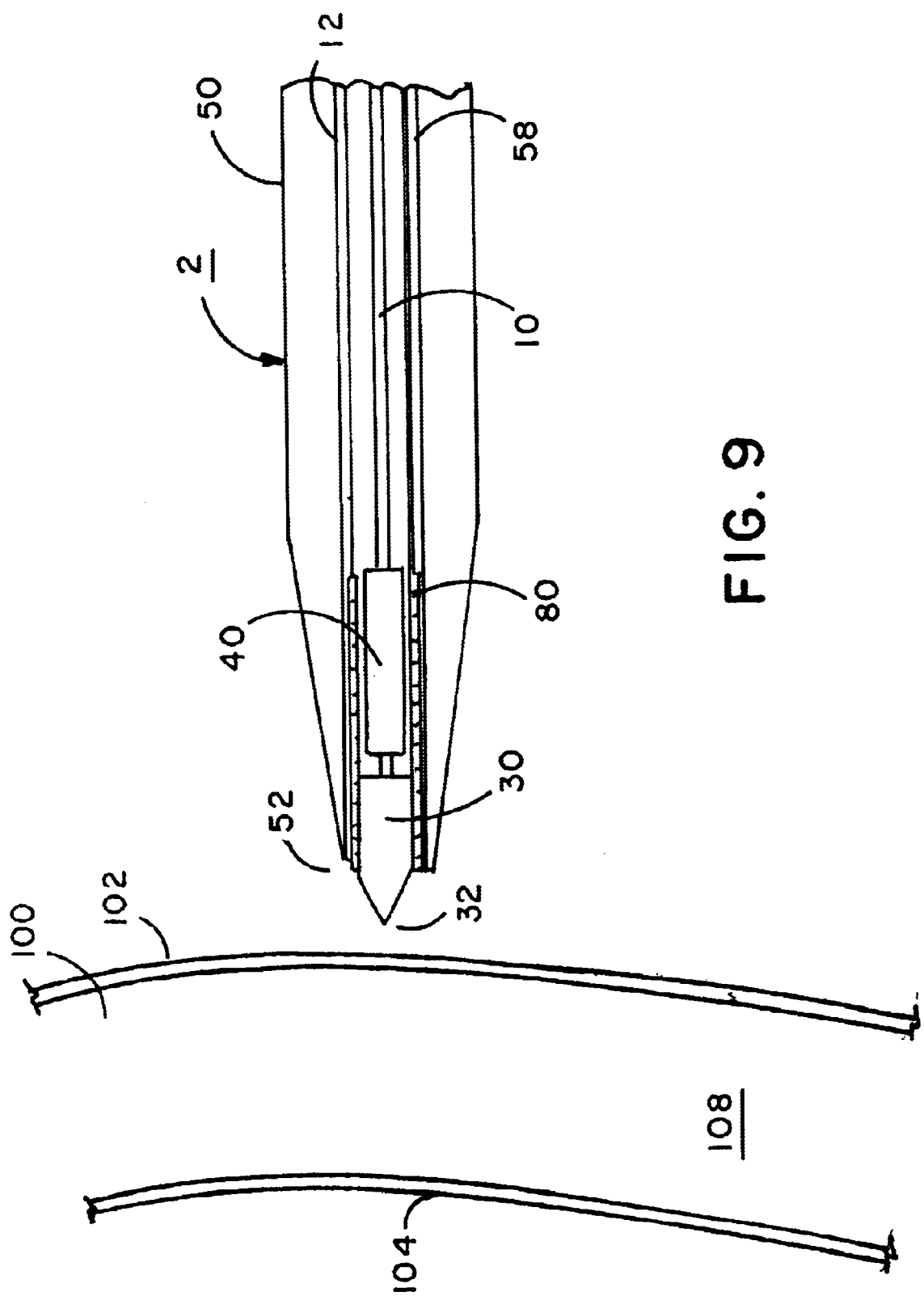
FIG. 9 is an illustration of the complete introducer assembly of FIGS. 8A and 8B when approaching a sidewall of a blood vessel or hollow organ in-vivo.
Figure 10:
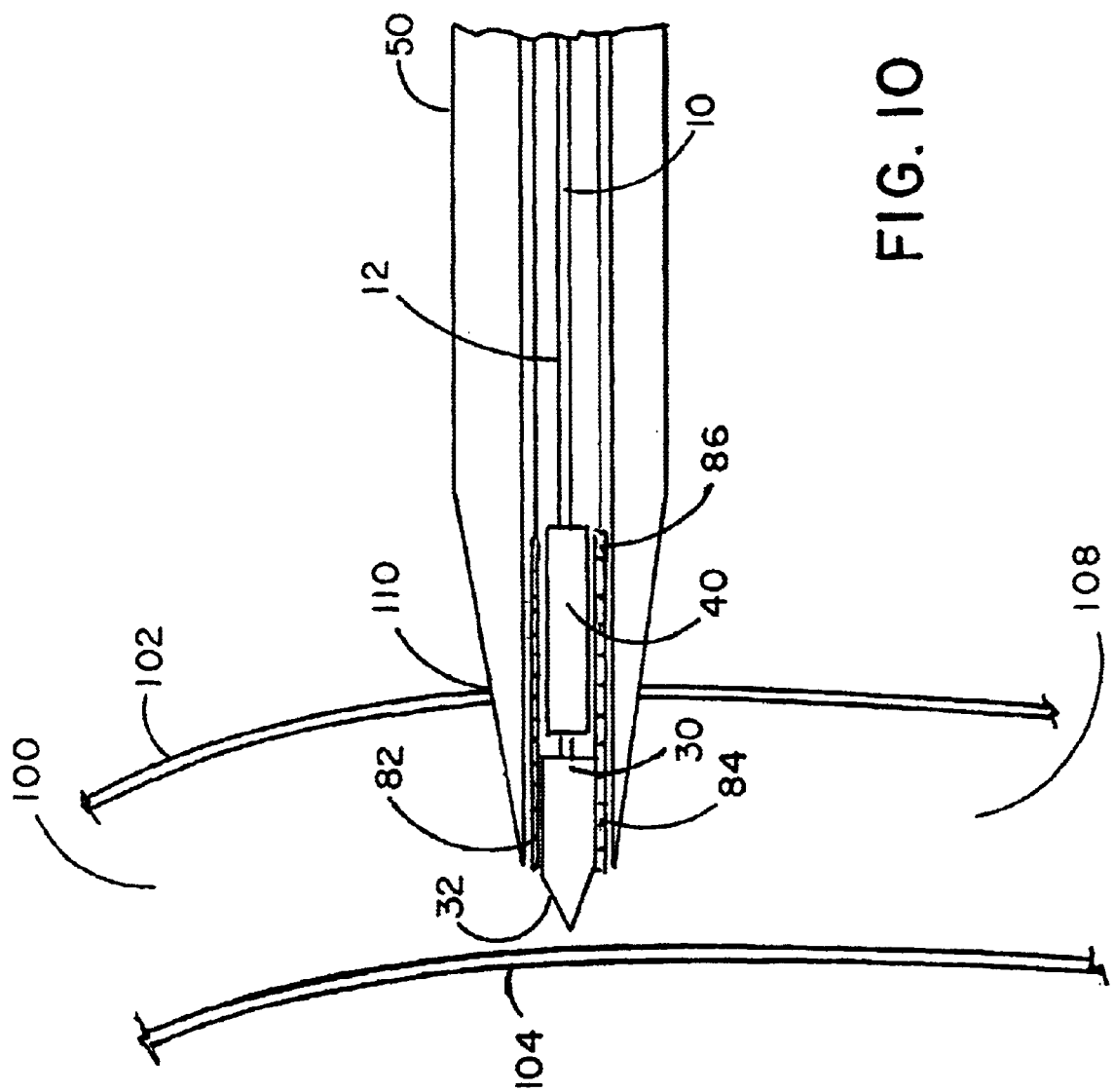
FIG. 10 is an illustration of the complete introducer assembly after piercing and penetrating through an aperture in the sidewall of a blood vessel or hollow organ.

FIG. 9 shows the complete introducer assembly as it approaches the front sidewall 102 of the blood vessel or hollow organ. It will be seen therein that the open end 52 of the volumetric sheath is placed adjacent to and in aligned closure with the perforating headpiece 30 of the perforator instrument. The prepared communication conduit 80 lies entirely within the internal spatial volume 58 of the volumetric sheath 50 as does the balloon appliance 40 and the supporting shaft 12 of the perforator instrument. Also, as shown by FIG. 10, the balloon appliance is in the deflated state thereby permitting the entirety of the perforator instrument 10 and the penetrating tip 32 in particular to pass out of the enveloped spatial volume provided by the volumetric sheath 50; then to cut into the sidewall 102; and thereby form an aperture 110. The introducer assembly as a whole is then advanced forward through the newly formed aperture 110.

FIG. 10 also shows the position of the prepared communication channel as an integrated unit through the aperture 110 in the front wall 102 of the blood vessel or hollow organ. As seen therein, the volumetric sheath 50 housing the linking connector 82 has been pushed forward such that the first cuff portion 84 lies positioned within the internal spatial volume of the blood vessel or hollow organ 100; and the perforating headpiece 30 and the deflated balloon appliance 40 have also been extended into the internal spatial volume 108 and thus support the prepared communication channel in this position.

Figure 11:
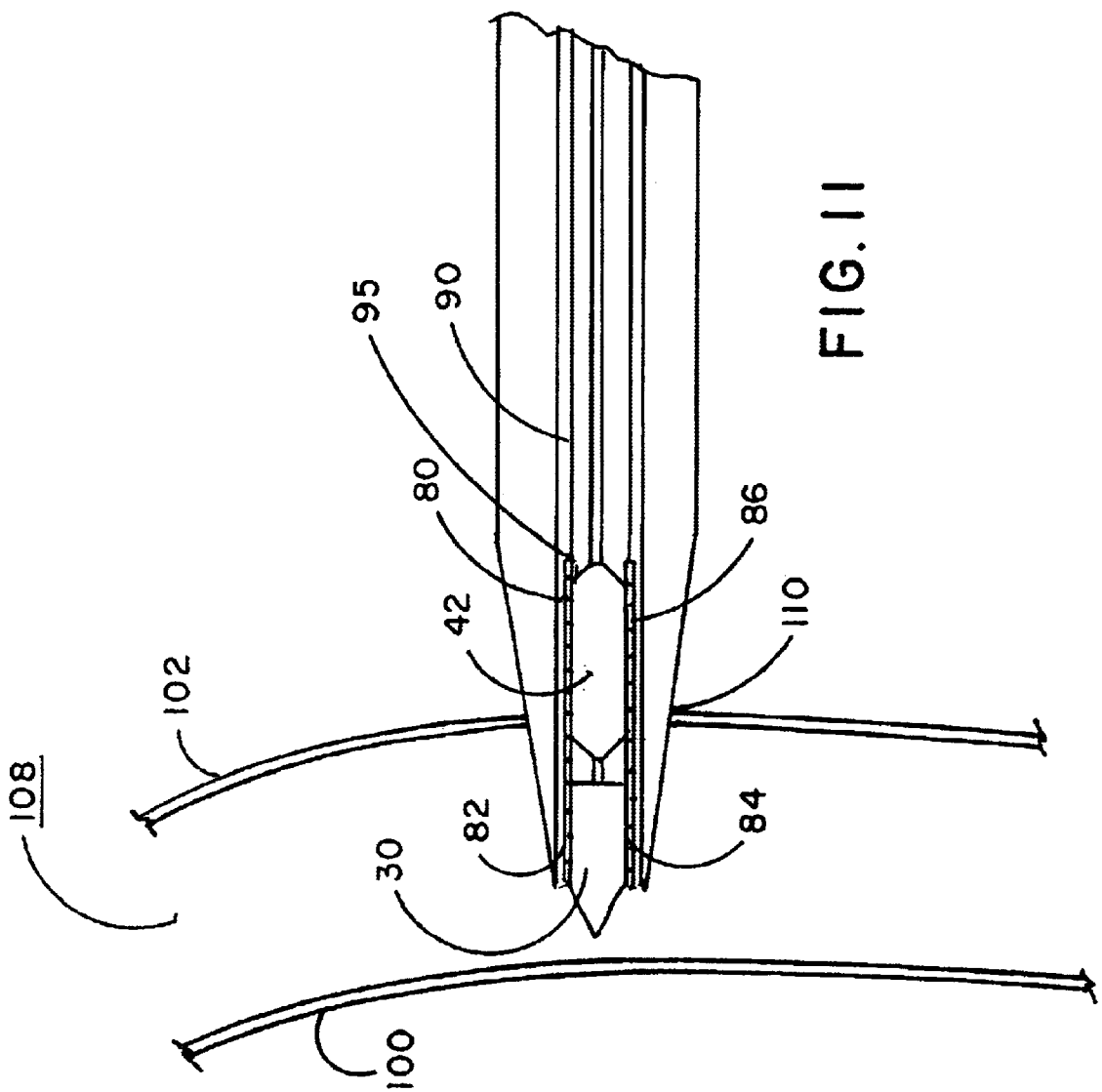
FIG. 11 is an illustration of the advancement forward of the prepared communication channel into the internal spatial volume of a blood vessel or hollow organ using the complete introducer assembly.

The balloon appliance then is preferably inflated by introducing fluid via the luer lock fitting (not shown) which is passed through the inflation line and inflates the balloon interior space 42 thereby holding the prepared communication channel 80 in place within the aperture 110 itself. This is illustrated by FIG. 11.

Figure 12:
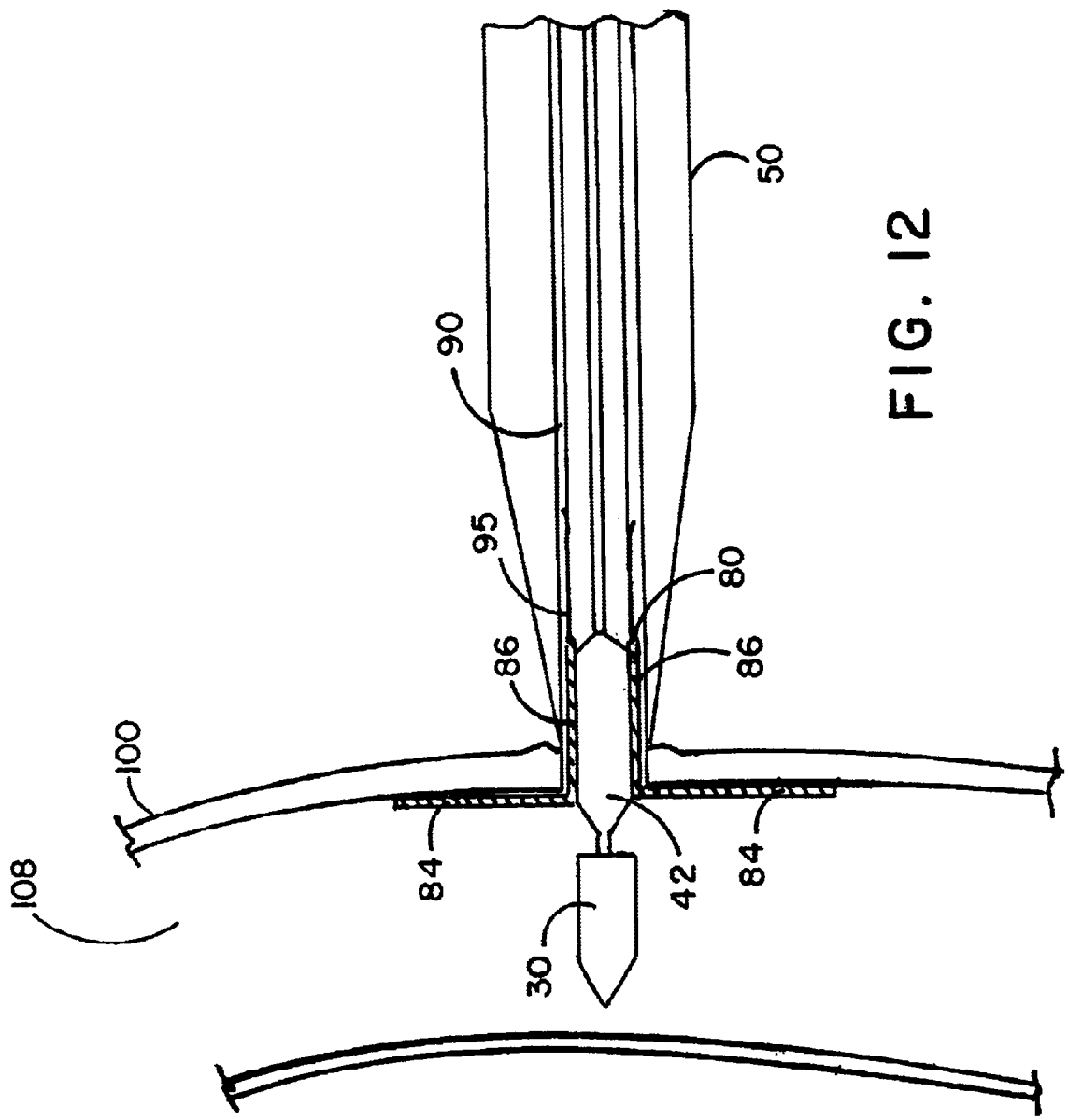
FIG. 12 is an illustration of the deployment in-situ and the sutureless securing of the prepared communication channel within the internal spatial volume of a blood vessel or hollow organ.

Accordingly, the linking connector 82 which has been permanently joined to the internal sidewall surface 95 of the tubular conduit 90, is then allowed to deform on-demand and deploy in-situ. This event is shown by FIG. 12. The individual acts of deformation and deployment of the first cuff portion 84 within the internal spatial volume 108 of the blood vessel or hollow organ 100 thus serve to secure the prepared communication channel 80 to the interior of the anatomic body part; and concurrently places the secured communication channel 80 in fluid flow communication with the internal spatial volume 108 of the blood vessel or hollow organ. Moreover, while the act of deployment within the internal spatial volume 108 occurs as illustrated by FIG. 12, the tubular conduit permanently joined to the second conduit retaining portion 86 remains in place and in a somewhat expanded state by superelasticity, thermoelasticity, and/or balloon inflation. This retained portion 86 permanently joined to the sidewall of the tubular conduit retains and secures the tubular conduit 90 for unobstructed fluid flow communication.

Figure 13:
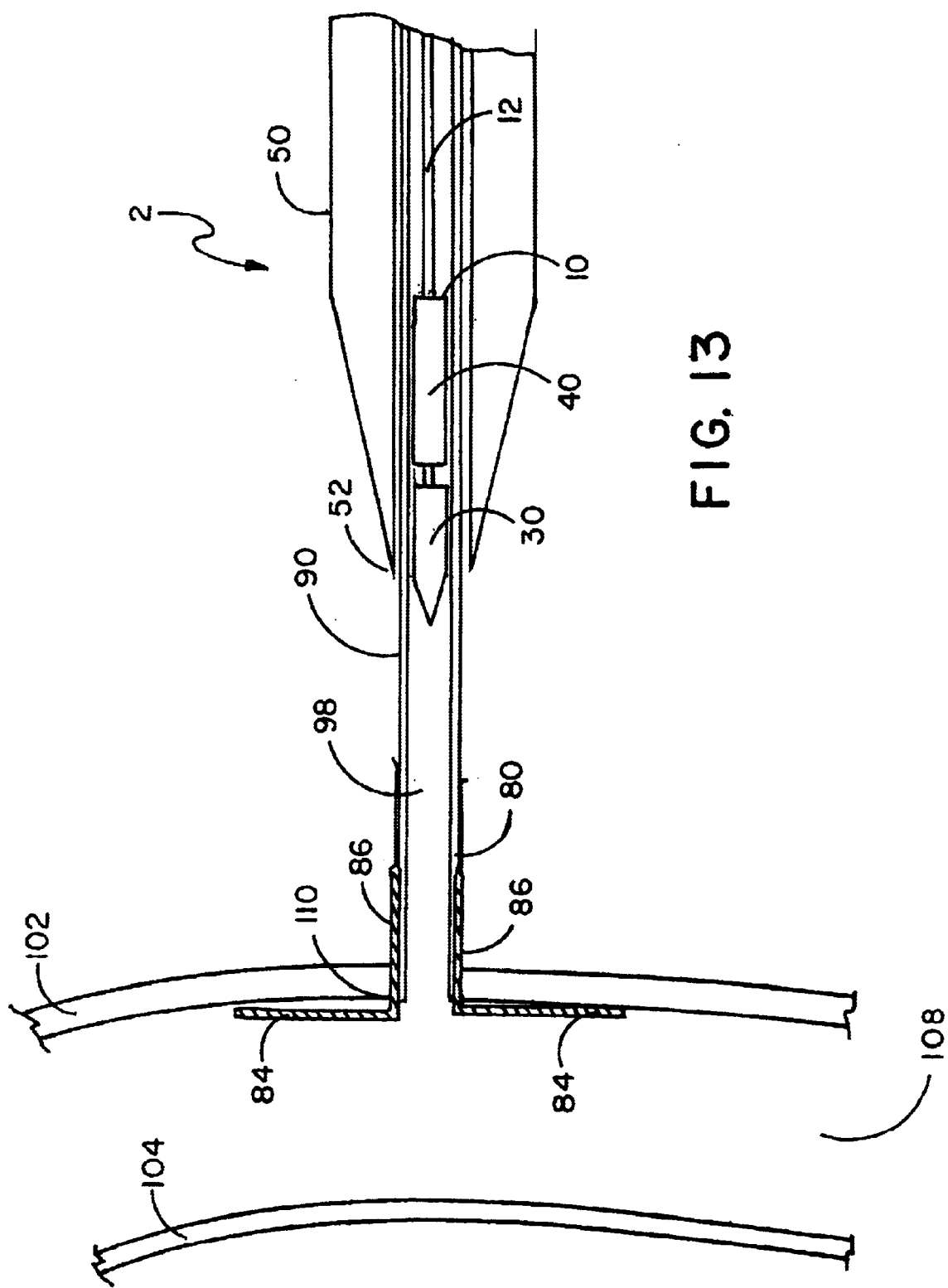
FIG. 13 is an illustration of the partial rearward withdrawal of the introducer assembly after the communication channel has been deployed and secured to a blood vessel or hollow organ.
Figure 14:
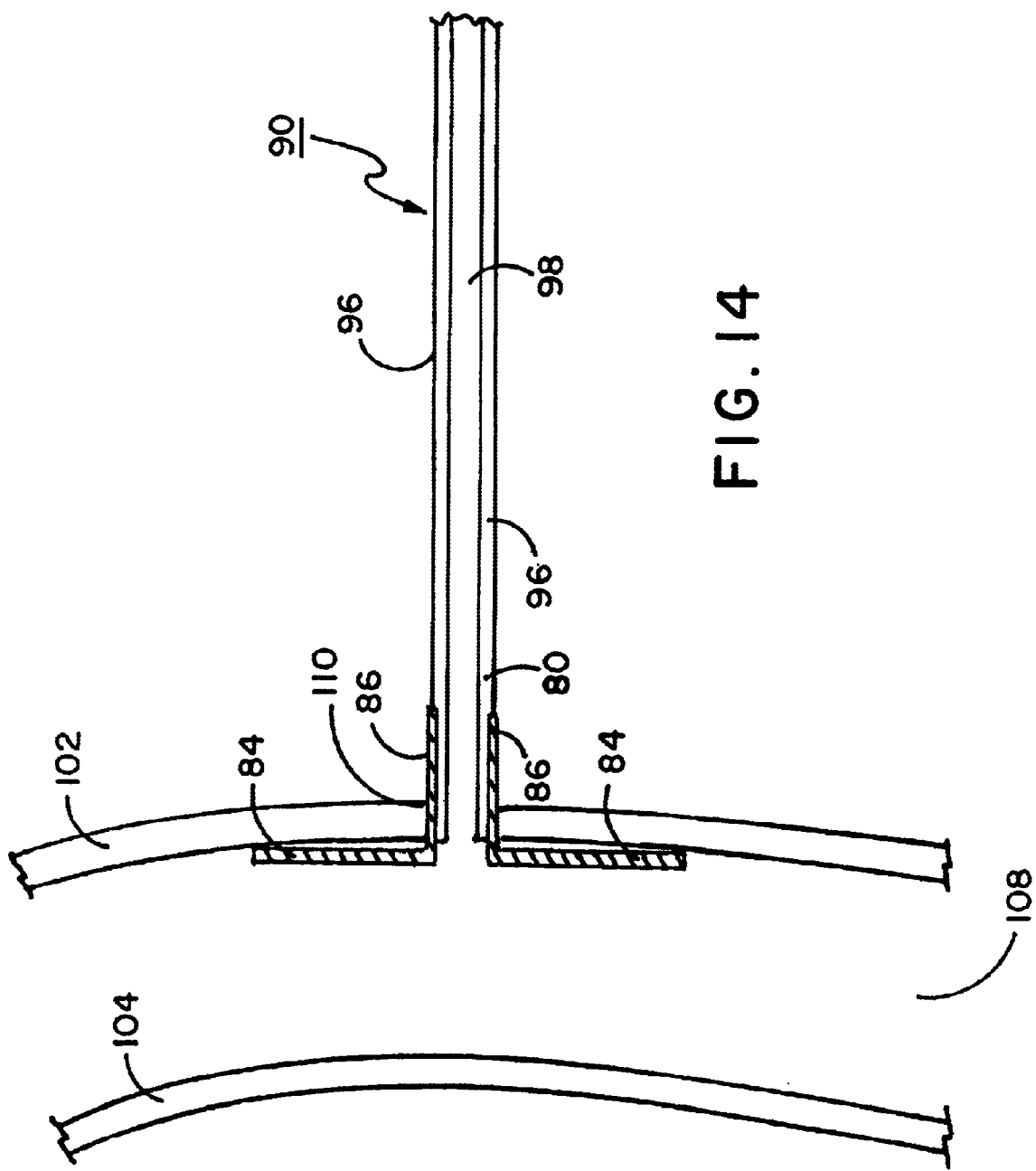
FIG. 14 is an illustration of the joined and secured communication channel after the introducer assembly has been removed.

The final stages of the method and system are illustrated by FIGS. 13 and 14 respectively. FIG. 13 shows the introducer assembly being withdrawn after deflation of the balloon from within the internal lumen 98 of the tubular conduit 90. FIG. 14 illustrates the final desired result and shows the sutureless juncture of the prepared communication channel 80 in position through the aperture 110 in the front wall 102 of the blood vessel or hollow organ 100. As seen therein, the prepared communication channel is joined to the, interior space of the blood vessel or hollow organ; is secured in a fluid-tight manner to the internal spatial volume 108 of the blood vessel or hollow organ interior; and is in fluid flow communication with the interior space of this anatomic body part. The linking connector 82 shows the first cuff portion 84 in the deformed state within the interior space of the blood vessel or hollow organ and shows that this in-situ deformation acts to secure the tubular conduit 90 to the interior spatial volume of the blood vessel or hollow organ and places the prepared communication channel in fluid flow communication for whatever purpose is desired by the surgeon for his patient.

II. Alternative Embodiments And Formats

The first preferred embodiment described previously herein is merely one structural assembly format whose component parts may be alternatively configured for a variety of purposes. To demonstrate the variety of alternative embodiments and structural formats, the following structural designs and constructions are provided. It will be expressly understood, however, that these described alternative embodiments and constructions are merely illustrative of the wide range and broad variety of alternatives which is well within the skill of the ordinary person skilled in this technical field; and that the described formats are merely representative examples of many other constructions which may be used equally well for a particular medical application or specific patient purpose.

Figure 15:
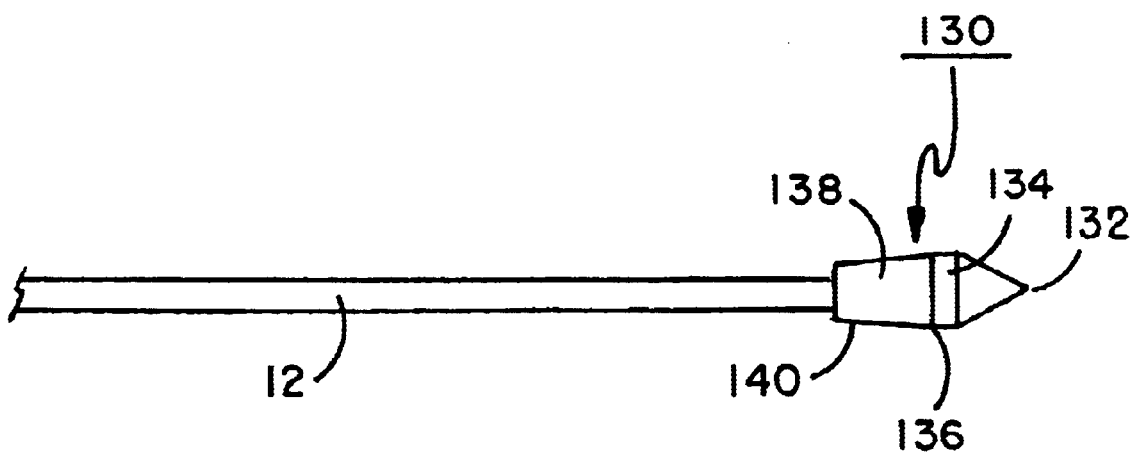
FIG. 15 is an illustration of one alternative embodiment for the perforating headpiece of the perforator instrument of FIG. 2.
Figure 16:
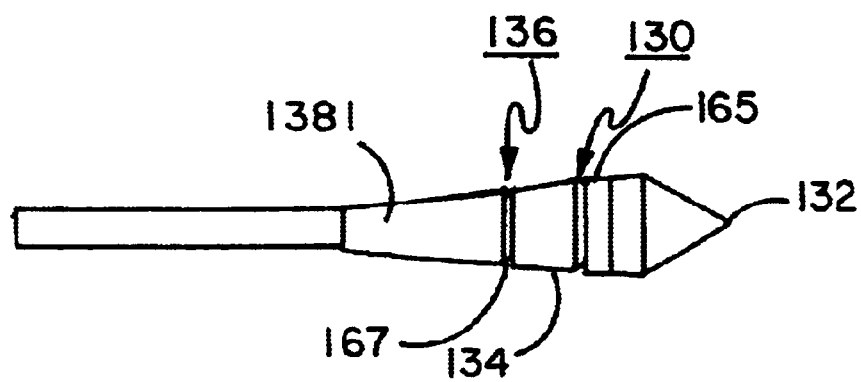
FIG. 16 is an illustration of a second alternative embodiment for the perforating headpiece of the perforator instrument of FIG. 2.

Alternative Embodiment 1:

A first alternative design and construction facilitates the passage and removal of the prepared communication channel over the axial length of the perforator instrument and concurrently allows for easy removal of the perforator instrument as well as the introducer assembly as a whole after the communication channel has been joined in-situ to the interior spatial volume of a blood vessel or hollow organ. For this purpose a first alternative construction for the perforating headpiece of the perforator instrument is provided as illustrated by FIG. 15. As seen therein, the perforating headpiece 130 now comprises a perforating cutting tip 132, a penetrating body 134 of diminished dimensions and size in comparison to that described previously herein; has a base aspect 136 which is now serving as a surface for a cone-shaped end element 138. As before, the perforating headpiece 130 is integrally joined to the supporting shaft 12 of the perforator instrument. In this construction, the point of juncture and integral union for the perforating headpiece 130 as a unit is at the cone-shaped end element 138.

The benefit and major advantage of this construction is that the cone-shaped base end element 138 is tapered along its sides 140; and that this tapered sidewall 140 for the cone-shaped end element 138 will not only permit easier passage and withdrawal through the linking connector; but also, if necessary, dilate the linking connector structure to permit an unobstructed withdrawal of the perforating headpiece 130 after the communication channel has been joined to the blood vessel or hollow organ interior space. If desired, the entire external surface of the perforating headpiece and the sides 140 of the cone-shaped base end element 138 in particular may be covered with a hydrophilic coating in order to provide a more slippery surface and ensure an easier passage.

Alternative Embodiment 2:

This second alternative embodiment and structural construction is illustrated by FIGS. 16–19 respectively. There are two essential parts to this second alternative embodiment. The first is revealed by FIGS. 16, 17A, and 17B respectively which reproduce in part the perforating headpiece 130 illustrated by FIG. 15 and described herein previously. In this alternative construction, the perforating headpiece 130 again includes a perforating tip 132, a penetrating body 134, a base aspect 136, and a cone-shaped end element 138; but also now comprises a plurality of recesses which individually appear as a groove 165 and a furrow 167 within the penetrating body portion 134 and the base aspect 136 respectively.

Particular details of this structural construction are shown by FIGS. 17A and 17B respectively. As seen therein the recessed groove 165 is circumferentially extensive and deep within the penetrating body 134. Similarly, the recessed furrow 167 circumferentially penetrates sharply through the base aspect 136 and the interior of the penetrating body 134. The cross sectional view illustrated by FIG. 17A shows the manner in which the recessed groove 165 and recessed furrow 167 exist in depth; in comparison, the cross-sectional view of the perforating headpiece 130 (looking forward from the supporting shaft towards the perforating tip 132) of FIG. 17B shows the concentric ring nature and annular alignment of the recessed groove 165 in comparison to the recessed furrow 167.

This second alternative embodiment of the perforating headpiece 130 having recessed groove 165 and recessed furrow 167 is intended to be employed with a modified construction for the volumetric sheath illustrated by FIG. 18. In this modified design structure and construction, the volumetric sheath 150 has a front open end 152 which is configured as multiple segmented tangs 154. The multiple segmented tangs 154 are preferably evenly spaced around the circumference of the open end 152 and are desirably biased such that the preferred positioning of the segmented tangs is in the open position as shown in FIG. 18; The multiple biased segmented tangs 154 when compressed annularly into the closed position will form a single circular and unified open end 152; and while in the closed position will provide a unitary opening 152 for the entirety of the volumetric sheath 150 despite being constructed as multiple segmented pieces. In this manner, the segmented tangs 154 will remain preferably in the open, biased position; but at will can be compressed to form a single circular or annular front end opening 152 and access to the interior spatial volume of the volumetric sheath 150.

The positioning of the multiple segmented tangs 154 in the closed position is intended for placement within the recessed groove 165 of the perforating headpiece 130 illustrated previously in FIGS. 16 and 17 respectively. The segmented tangs 154 will fit into and be held by the recessed groove 165; and form itself within the interior space of the groove as the unitary annular opening 152. This is shown by FIG. 19. In addition, the recessed furrow 167 will receive and hold the first cuff portion 84 of the linking connector 82 after it has been permanently joined to the tubular conduit as the prepared communication channel. The placement of the linking connector 82 at the first cuff portion 84 into the recessed furrow 167 is also illustrated in FIG. 19. This linking connector placement thus allows a further degree of certainty and safety for the prepared communication channel after it has been positioned around the supporting shaft of the perforator instrument and has been enveloped by the volumetric sheath 150.

Alternative Embodiment 3:

A third alternative construction provides a variant format for the volumetric sheath of the introducer assembly. This third alternative construction is illustrated by FIG. 20 and utilizes in part the volumetric sheath structure illustrated by FIG. 18 and described in detail previously herein. In this alternative embodiment, however, the variant structure includes inner sleeve 160 which is of predetermined dimensions and substantially cylindrical configuration. The inner sleeve 160 comprises a open front end 162, an open rear end 164, and a cylindrically-shaped grip 161 joined to the rear end 164. Not only does the inner sleeve 160 slide forward and rearward at will within the interior volume of the volumetric sheath 150; but as the inner sleeve 160 is slid forward towards the segmented tangs 154, the front end 162 engages the segmented tangs 154 of the volumetric sheath 150 and forces the tangs open as a consequence of the physical engagement. This allows quick and easy removal of the volumetric sheath 150 from the introducer assembly, especially after the segmented tangs 154 have been placed in the closed position forming a unitary annular front end.

One major benefit and advantage of this alternative construction using the inner sleeve 160 as illustrated within FIG. 20 is that this format allows the volumetric sheath 150, the outer sheath covering, to be made of a woven synthetic textile material which is prepared in advance and coated with a non-porous polymer coating. The polymer coating would preferably bias the woven textile material of the outer volumetric sheath in the closed position in which the multiple segmented tangs would reform as a single annular opening. Thus, as the inner sleeve is advanced within the outer volumetric sheath, it would effectively expand the polymer coated woven textile material and permit removal of the outer volumetric sheath in a far easier fashion.

Clearly this type of construction and format allows for a volumetric sheath which is composed or designed using a woven synthetic textile material; and thus allows a fabric type construction and a fabric arrangement for the outer sheath which acts as the protective barrier and covering around the perforating instrument. This type of woven textile construction and embodiment for the volumetric sheath, with or without the presence and use of an inner sleeve as shown within FIG. 20, is merely one variant of the many different constructions and materials which may be employed with the introducer assembly as a whole.

Alternative Embodiment 4:

A fourth alternative design and construction is illustrated by FIGS. 21 and 22 respectively. This format and structural design permits the surgeon to utilize the Seldinger technique, a favored procedure for this kind of surgery. In this technique, a guidewire is positioned in the targeted blood vessel or hollow organ wall; and it is this guidewire which is then utilized as the means for precise guidance and placement of the introducer assembly as a whole at that precise anatomic location. For this purpose the alternative construction of FIGS. 21 and 22 is added to the first preferred embodiment previously described herein.

As illustrated, the perforator instrument is comprised of the supporting shaft 12, the perforating headpiece 30 and the knob handle 15. However, within the internal lumen 18 of the support shaft 12, a second hollow lumen 180 exists which extends and passes through the axial length of the perforator instrument 10. This is shown by FIG. 21. The guidewire hollow lumen 180 extends through the perforating headpiece 30, through the supporting shaft 12 over its axial length, and exits adjacent to the handle 15 where it is joined to flexible tubing 182. The flexible tube 182 is joined to the hollow lumen 180 at the juncture point 186; and the flexible tube 182 provides an entry portal 184 through which the guidewire exits. A cross sectional view of this internal arrangement, the perforating headpiece end, is illustrated by FIG. 22.

The use of the Seldinger technique and the ability to pass a guidewire from the anatomic targeted site at the blood vessel wall or hollow organ wall directly through the perforating tip of the perforating headpiece and continuously through the entirety of the introducer assembly provides a major advantage and benefit for the assembly.

III. A Second Preferred Embodiment

A second preferred embodiment of the introducer assembly and system which is the present invention is illustrated by FIGS. 23 through 33 respectively. This second preferred embodiment conforms to and satisfies the minimal component part requirements of each and every introducer assembly as a whole; but this preferred embodiment is a far more elaborate and sophisticated engineering design and construction.

An overview of this second preferred embodiment is provided by FIG. 23 which shows the introducer assembly 202 as an arranged apparatus comprising a perforator instrument 210, volumetric sheath 250, and position holding means configured as a pistol-grip mounting 204.

Figure 25:
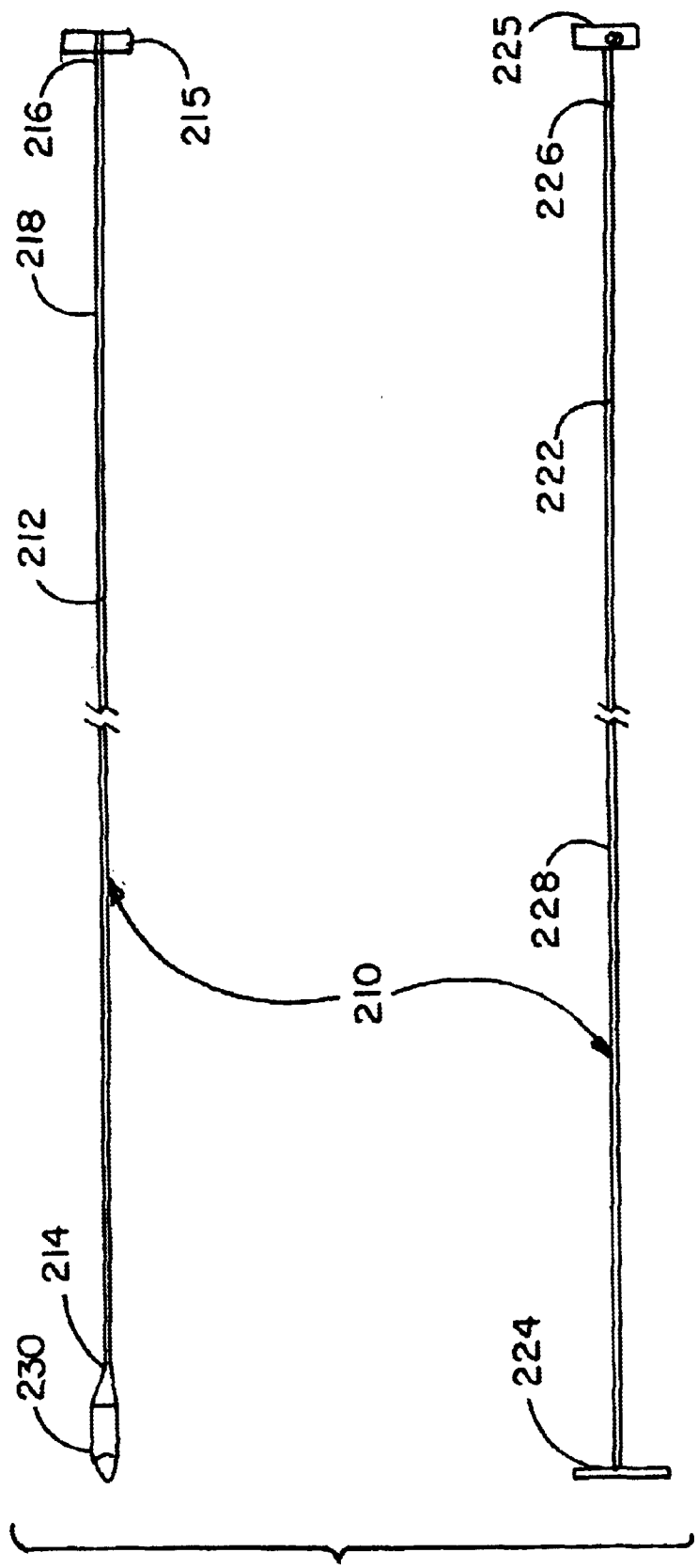
FIG. 25 is an illustration showing details of the coaxial supporting shafts in the perforator instrument of FIG. 24.

A detailed view of the perforator instrument 210 and the means for controlling the communication channel configured as a cuff stopper/holder subassembly 270 are shown by FIGS. 24, 25 and 26 respectively. As seen therein, the perforator instrument 210 is comprised of two coaxial support shafts 212 and 222. The longer and innermost support shaft 212 has two ends 214, 216 and an internal lumen 218. A knob handle 215 is joined to the support shaft 212 at the end 216. At the other shaft end 214 is attached to a perforating headpiece 230.

The second coaxial support shaft 222 is somewhat larger in overall diameter over its axial length than counterpart support shaft 212. This second support shaft 222 has two ends 224, 226; and a control knob 225 joined to the shaft 222 at the end 226. When coaxially joined together the support shaft 222 serves as the external or outermost shaft whereas the innermost support shaft 212 lies internally and coaxially within its diameter. This relationship is illustrated by FIGS. 26 and 24 respectively.

The perforating headpiece 230 is seen in detail within FIG. 26 and is comprised of a multi-faceted cutting tip 232, a penetrating body 234, a base aspect 236, a recessed furrow 267, and a cone-shaped base end element 238. The cone-shaped base end element is collapsible to accommodate the positioning of the cuff into the cone-shaped base element and expandable to accommodate the withdrawal of the headpiece through the deployed cuff. This perforating headpiece 230 is integrally joined to the supporting shaft 212 at the front shaft end 214.

One advantage of the perforating headpiece 230 is the multi-faceted cutting tip 232 which provides multiple faces and cutting edges 232. The number of multiple faces and edges is typically from 3–5 edges; and such a multi-faced and multi-edged bladed tip is deemed to be more effective as a cutting tool than a single bladed tip. In addition, it is recognized that single bladed or edged perforating tips often produce lacerations in the blood vessel or hollow organ wall which subsequently may fracture or fragment. For this reason it is believed that multi-faced and multi-edged cutting tips are preferred and would be ideal in most use applications.

The communication channel controlling means is specifically embodied as connector stopper/holder subassembly 270 and is best illustrated by FIGS. 26, 28A, and 28B. As seen therein, the collapsed position for the stopper/holder 270 is illustrated by FIG. 28A while the open or expanded position is illustrated by FIG. 28B. As seen therein, the stopper subassembly 270 comprises expandable and collapsible segments 274, each of which is mounted on a segment supporting strip 276. The stopper subassembly 270 is joined to coaxial supporting shaft via the support strips 276; and passes coaxially over the inner supporting shaft 212 over its axial length within the internal lumen 301 of the outer supporting shaft 300. When the outer supporting shaft 300 is withdrawn rearward, the stopper 270 expands into its open position as shown; and when outer supporting shaft 300 is advanced forward over the supporting strips 276, the stopper segments 274 are pulled together forcing the stopper subassembly into the collapsed state as shown by FIG. 28.

The purpose of the stopper/holder subassembly 270 is to provide a structural backstop for the linking connector (then already joined to the tubular conduit as the prepared communication channel); and to support the back of the linking connector during withdrawal of the perforating headpiece 230. The stopper/holder assembly 270 is expanded during placement of the linking connector; and the expanded stopper subassembly engages the end of the linking connector as a back stop. When properly, the linking connector (already joined to the tubular conduit) will thus rest against the front face 280 of the stopper subassembly; and the stopper subassembly thereby provides the means for controlling the prepared communication conduit while positioned within the introducer assembly. Once the prepared communication conduit is deployed into the interior space of a blood vessel or hollow organ target, the stopper/holder subassembly 270 is reduced into the collapsed state and allows the subassembly to be withdrawn rearward as part of the perforator instrument 210.

The volumetric sheath 250 of the second preferred embodiment is shown in detail by FIG. 27. As seen therein, the volumetric sheath 250 comprises two open ends 252, 254; a sidewall 256; and an internal spatial volume 258. In this embodiment for the volumetric sheath 250, a flange 260 is mounted on the exterior surface of the volumetric sheath at the open end 252. This end flange 260 has an extended annular rib 262 and a rib perimeter 264 of predetermined dimensions. At the other open end 254 is a sidewall alignment hole 266 which is utilized in the positioning of the volumetric sheath 250 within the introducer assembly by acting to stop the forward motion of the introducer assembly and to limit entry of the assembly to only that degree which is needed.

Finally, the position holding means which are attachable to and detachable from the volumetric sheath of FIG. 27, and used for holding the volumetric sheath 250 and its enveloped spatial volume at a set position around the two supporting shafts 300, 212, 222, is best seen in FIG. 23. As illustrated therein, the position holding means is embodied as a pistol-grip mounting 204 having a mounted body 206 and a finger grip 208. The volumetric sheath 250 is internalized at the end 254 and held in aligned position via the sidewall alignment hole 266; and the pistol-grip mounting holds the volumetric sheath via the alignment hole 266 in the complete introducer assembly.

One additional feature is provided as an extra point of manipulation and control for the introducer assembly as a whole. This is shown as the knob 285 and appears in FIGS. 23 and 28 to best advantage. The controller knob 285 is mounted on the exterior surface of the outermost support shaft 300. In aligned position, the control knob 285 is located within the pistol-grip mounting 204; allows for manipulation of the outer most supporting shaft 300; and is a controller for placing the stopper subassembly 270 from an open position into a collapsed position and subsequently back into an open position repeatedly on-demand. This is an optional feature but a preferred item in this embodiment because it provides precision control for the connector stopper subassembly without major change in position of either coaxial supporting shaft 212 and 222 respectively.

When a prepared communication channel 80 is positioned within this introducer assembly 250, the complete system methodology is ready to be used by the surgeon. A cross sectional detail of the complete introducer assembly is provided by FIG. 29. As seen therein, the communication channel 80 is positioned within the internal spatial volume 258 of the volumetric sheath 250. Placed within the internal lumen 98 of the tubular conduit 90 is the perforator instrument 210 including the perforating headpiece 230, the inner supporting shaft 222, the stopper subassembly 270 in the expanded state, and the outer supporting shaft 300. By use of the stopper subassembly 270 which is positioned against the second retained portion 86 of the linking connector 82, full manipulative control of the communication channel as a prepared article of manufacture is maintained throughout.

Figure 29:
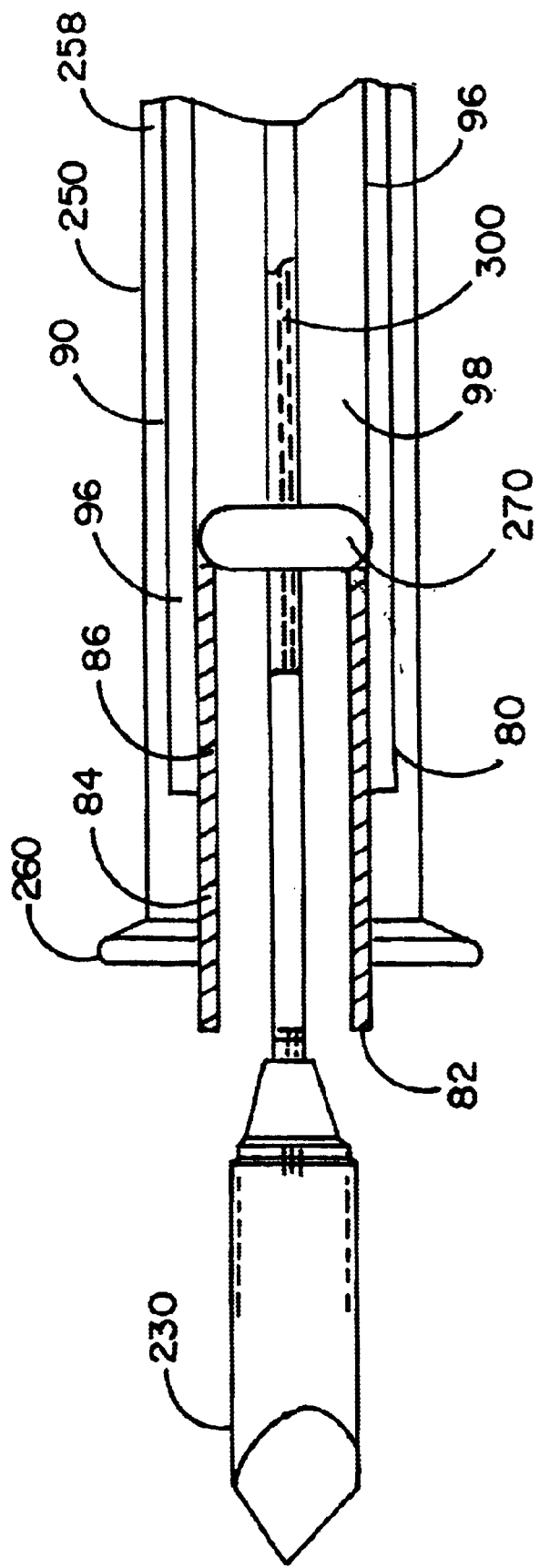
FIG. 29 is a partial cross-sectional illustration of the prepared communication channel of FIG. 6C positioned within the complete introducer assembly of FIG. 23.
Figure 30:
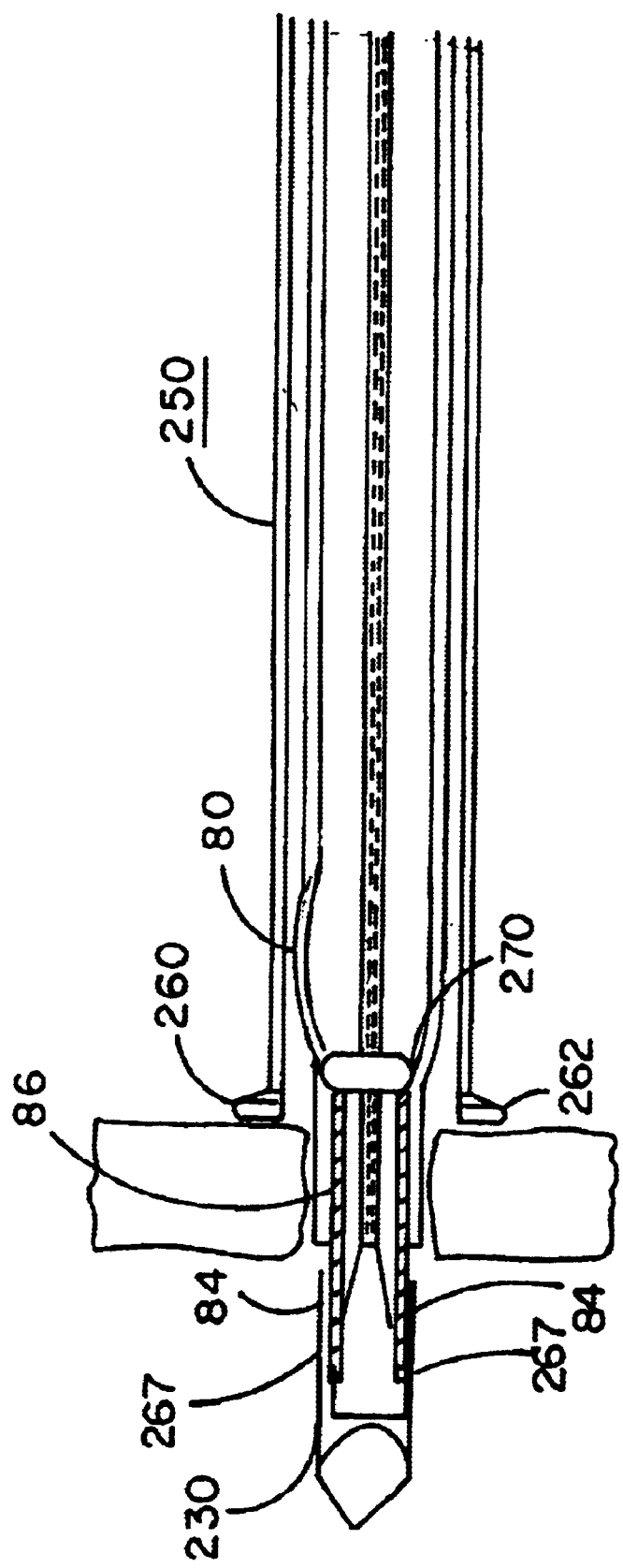
FIG. 30 is a cross-sectional illustration of the complete introducer assembly of FIG. 29 after piercing and penetrating through an aperture in the sidewall of a blood vessel or hollow organ.
Figure 31:
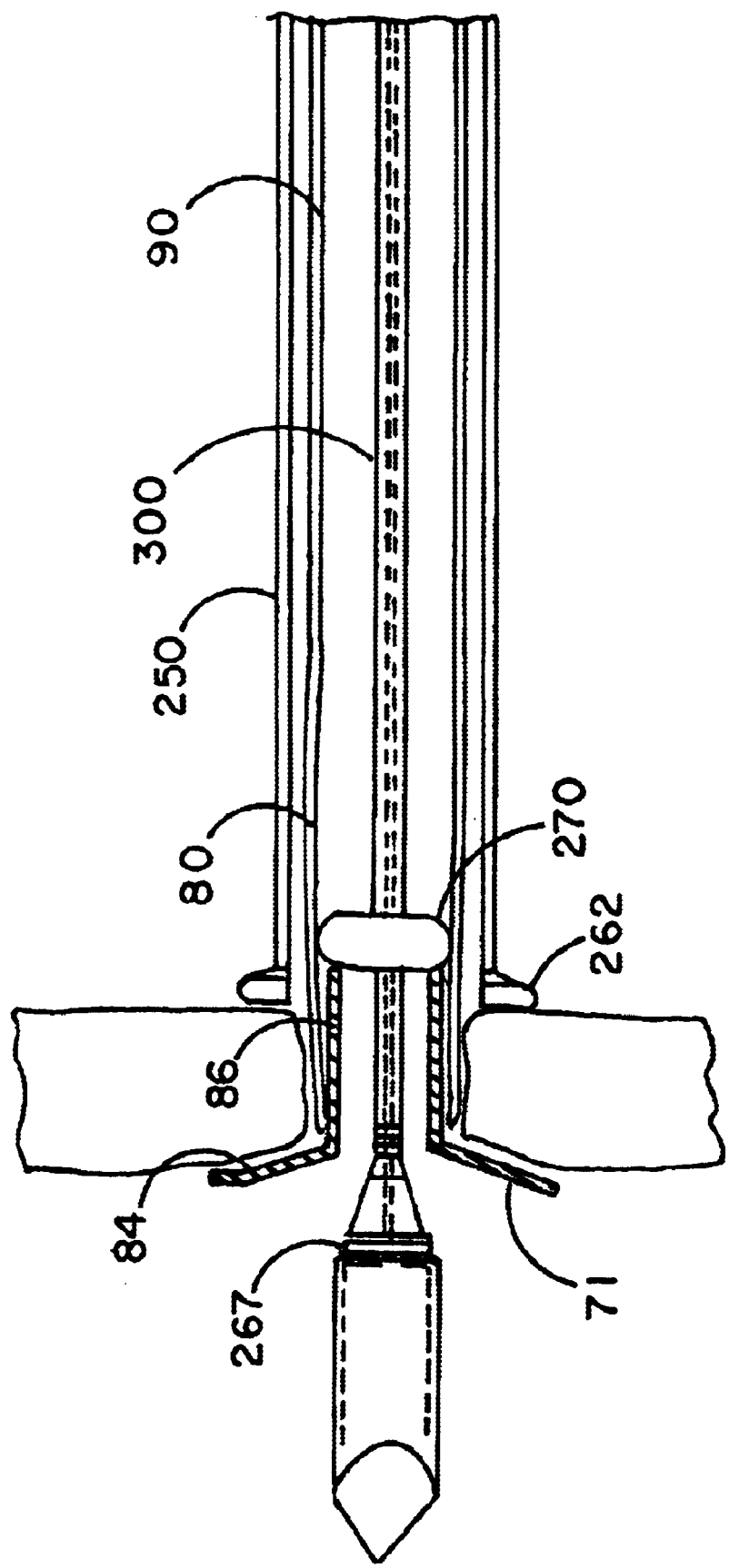
FIG. 31 is an illustration of a deployment at will within the internal spatial volume of a blood vessel or hollow organ and the securing of the communication channel to the blood vessel or hollow organ.

The deployment and method of usage for this second preferred embodiment is shown by FIGS. 30–33 respectively. The complete introducer assembly illustrated within FIG. 29 and generally by FIG. 23 is employed as shown to penetrate the wall of a targeted blood vessel or hollow organ. This is shown by FIG. 30. The perforating headpiece 230 has penetrated into the interior spatial volume of the targeted blood vessel or organ while the end flange 260 of the volumetric sheath 250 remains against the exterior surface of the target. The end flange 260 serves to stop the forward motion of the introducer assembly as a whole by providing a larger diameter sheath than the aperture formed by the perforating headpiece 230. After the perforation aperture has been made, the perforating headpiece 230 alone is advanced forward thereby releasing the first cuff portion 84 from the recessed furrow 267. The linking connector is now free to deform in full and to be deployed completely in-situ within the internal spatial volume of the penetrated target vessel or organ. This is illustrated by FIG. 31.

Figure 32:
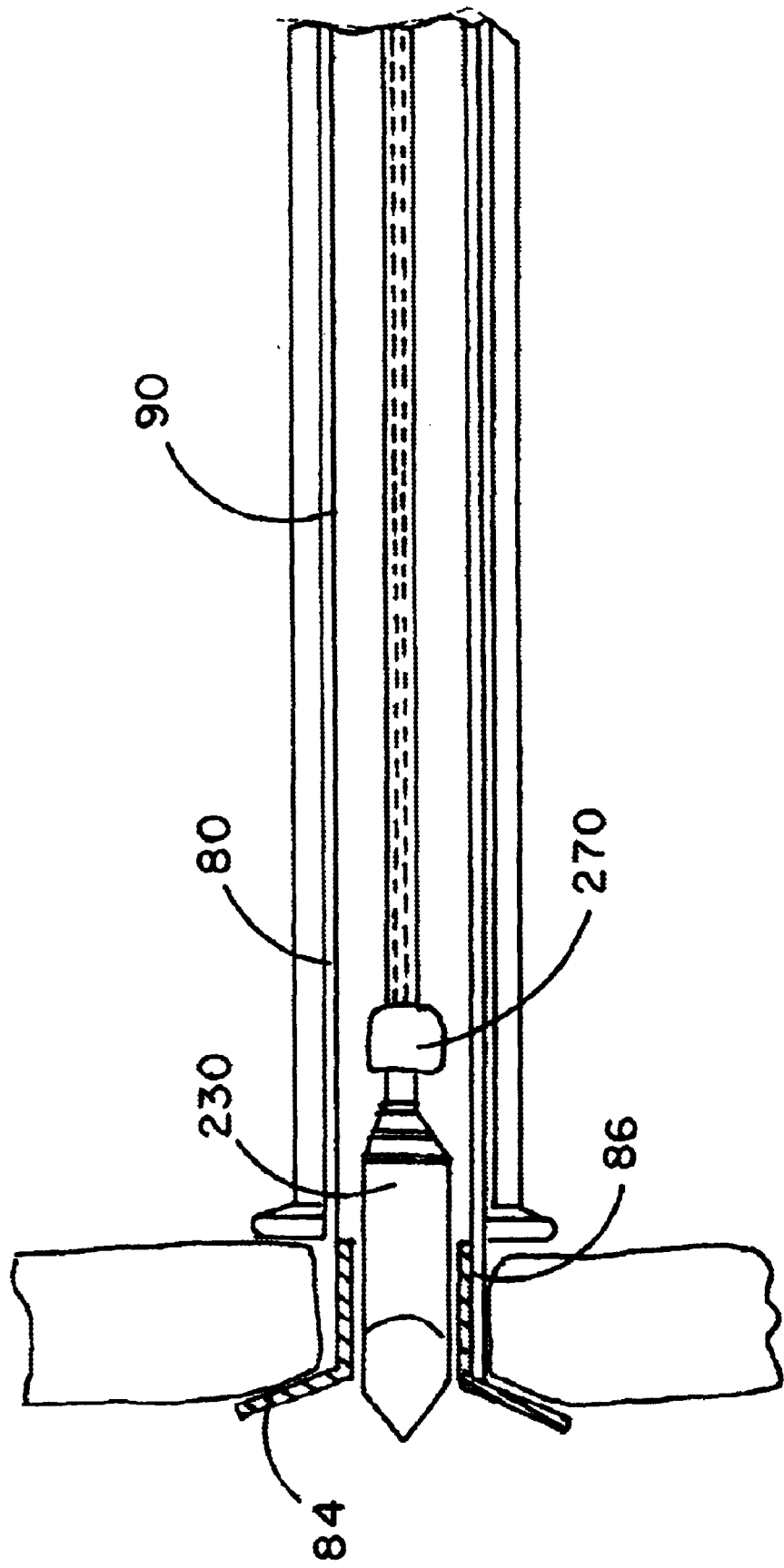
FIG. 32 is an illustration of the partial rearward withdrawal of the introducer assembly of FIG. 23 after the communication channel has been deployed and secured to a blood vessel or hollow organ.

Subsequently, the perforating headpiece 230 may be withdrawn through the internal lumen of the joined and secured communicating channel. This is illustrated by FIG. 32 and is achieved by manipulating the controlling knobs 215 and 225 rearward. The knob 285 is then advanced to collapse the stopper subassembly. The entire introducer assembly is then pulled back using the finger grip 208 of the pistol-grip mounting 204, the deformed linking connector and tubular conduit joined and secured to the internal spatial volume of the targeted blood vessel or hollow organ. This result is illustrated by FIG. 33.

IV. The Prepared Communication Channel

A. The Linking Connector

An essential component part of the prepared communicating channel is the presence and use of a superelastic and thermoelastic linking connector preferably comprised of a shape-memory alloy composition.

The shape-memory metal alloy compositions preferably used with the present invention constitute conventionally known blends and formulated metallic mixtures of nickel and titanium which undergo a phase transition—that is, a molecular rearrangement of atoms, molecules or ions within a lattice structure—due to a temperature change. The unique capability of shape-memory alloys is that these alloys are extremely elastic, flexible, and durable; these alloys change shape or configuration as a direct consequence of a change in temperature; and the alloy composition "remembers" its earlier and specifically prepared shape because the phase change affects its structure on the atomic level only, without disturbing the arrangement of the molecules which would otherwise be irreversible.

Superelasticity and Thermoelasticity

When these shape-memory alloys are intentionally superheated far above their transition temperature (either electrically or by external heat), a stretched temperature transformed alloy format results which contracts and exerts considerable force; and the temperature transformed alloy composition will become memory-shaped (deformable in-situ) in a fixed specific configuration. Afterwards, when cooled to below its transition temperature, the prepared alloy composition presents superelasticity properties which allow the alloy to be bent and shaped into other configurations while retaining the fixed "memory" of the particular shape in the earlier superheated condition, the thermoelastic properties. Thus, these shape-memory alloy compositions are recognized as being both superelastic and thermoelastic compositions of matter.

Alloy Formulations

At least twenty different formulations of these superelastic and thermoelastic alloys are conventionally known, all of these comprising different mixtures of nickel and titanium in varying percentage ratios [*Design News*, Jun. 21, 1993 issue, pages 73–76]. These metal alloys are conventionally utilized today in the manufacture of diverse products. For example, a range of different shape-memory alloy wires are commercially available in diameters from 0.001–0.010 inches [Dynalloy, Inc., Irvine, Calif.]. In addition, surgical anchors having such superelastic properties and formed by two or more arcs of wire strands (which can withstand strains exceeding 10%) have been developed [Mitek Surgical Products, Inc., Norwood, Mass.]. Also, blood clot filters formed of superelastic shape-memory alloy wires are commercially sold for implantation in large blood vessels such as the vena cava [Nitinol Medical Technologies, Inc., Boston, Mass.]. While these commercially available products illustrate the use of one or more superelastic and thermoelastic properties as particular articles, a more general listing of conventionally known properties and characteristics for shape-memory alloy compositions is provided by Table 1 below.

TABLE 1

Conventionally Known Properties of Shape-Memory Alloys[1]

| Transformation Properties | |
|---|---|
| Transformation Temperature | −200 to −110° C. |
| Latent Heat Of Transformation | 5.78 cal/g |
| Transformation Strain (for polycrystalline material) | |
| for a single cycle | 8% maximum |
| for $10^2$ cycles | 6% |
| for $10^5$ cycles | 4% |
| Hysteresis* | 30 to 50° C. |
| Physical Properties | |
| Melting point | 1300° C. (2370° F.) |
| Density | 6.45 g/cm$^3$ (0.0233 lb/in$^3$) |
| Thermal Conductivity | |
| austenite | 0.18 W/cm · ° C. (10.4 BTU/ft · hr ·° F.) |
| martensite | 0.086 W/cm · ° C. (5.0 BTU/ft · ° F.) |
| Coefficient of Thermal Expansion | |
| austenite | 11.9 × 10$^6$/° C. (6.11 × 10$^{-6}$/° F.) |
| martensite | 6.6 × 10$^6$/° C. (3.67 × 10$^{-6}$/° F.) |
| Specific Heat | 0.20 cal/g · ° C. (0.20 BTU/lb · ° F.) |
| Corrosion Performance** | excellent |
| Electrical Properties | |
| Resistivity (ρ) [resistance = p · length/cross-sectional area] | |
| austenite | ~100 μΩ · cm (~39.3 μΩ · in) |
| martensite | ~80 μΩ · cm (~31.5 μΩ · in) |
| Magnetic Permeability | <1.002 |
| Magnetic Susceptibility | 3.0 × 10$^6$ emu/g |
| Mechanical Properties | |
| Young's Modulus*** | |
| austenite | ~83 GPa (~12 × 10$^6$ psi) |
| martensite | ~28 to 41 GPa (−4 × 10$^6$ to 6 × 10$^6$ psi) |
| Yield Strength | |
| austenite | 195 to 690 MPa (28 to 100 ksi) |
| martensite | 70 to 140 MPa (10 to 20 ksi) |
| Ultimate Tensile Strength | |
| fully annealed | 895 MPa (130 ksi) |
| work hardened | 1900 MPa (275 ksi) |
| Poisson's Ratio | 0.33 |
| Elongation at Failure | |
| fully annealed | 25 to 50% |
| work hardened | 5 to 10% |
| Hot Workability | quite good |
| Cold Workability | difficult due to rapid work hardening |
| Machineability | difficult, abrasive techniques are preferred |

*Values listed are for a full martensite to austenite transition. Hysteresis can be significantly reduced by partial transformation or ternary alloys.
**Similar to 300 series stainless steel or titanium.
***Highly nonlinear with temperature All the different specific formulations and metallic blends comprising nickel and titanium which yield a deformable, thermoelastic, shape-memory alloy composition are suitable for use when practicing the present methodology. All of these shape-memory alloys rely on a crystal phase change from a higher temperature Austenite form to a lower temperature Martensite form to accomplish the memory effect. The cubic Austenite phase behaves much like ordinary metals as it deforms. In contrast, the complex crystal Martensite form can be found by reversible movement of twin boundaries to change the average "tilt" or strain in each segment of the alloy. The overall strain can be eliminated by releasing the stress, by maintaining it if it is not thermally stable (the superelastic effect), or by heating the alloy to change it back to Austenite form (shape-memory effect).

The crystal transformation of shape-memory alloy compositions is, by definition, thermoelastic—i.e., it progresses in one direction on cooling below the transition temperature and in the other direction upon heating above the transition temperature. The amount of transformation change versus temperature, measured either as the percent of Martensite form or the strain in a constantly stressed element, is a function of and can be plotted against temperature (CC) directly; and the change from one phase (and identifiable shape) to another typically occurs in a narrow temperature range (often 5–10° C.). Hysteresis takes place before the reverse transformation occurs.

The amount of strain accommodated due to the movement of twin boundaries, differs in each metallic alloy blending system. In the nickel-titanium system for example, up to 8% reversible tensile strain is available; however, to guarantee a long life use, the strain is often limited to 4–5%.

The stress-strain behavior of shape-memory alloy compositions is employed to help explain the shape-memory effect. For instance, Martensite is much easier to deform than Austenite. Therefore, one can deform the alloy while cold with much less force than when heated to change it back into Austenite form. As a result, the alloy converts thermal energy to mechanical work at high forces.

Fixing the Memory-shaped Configuration in the Metal Alloy

To prepare and fix the particular (or desired) shape to be "remembered" when the alloy undergoes a temperature phase transition, the alloy composition must be superheated initially to about 500° C. (or roughly 930° F.) for an hour while held in the fixed shape and position to be memorized. During the superheating process, the native alloy blend enters what is called the Austenite phase—a rigid lattice of nickel atoms surrounded by titanium alloys. Then, as the alloy metal cools below its transition temperature (which will vary with the percentage proportions of nickel and titanium), the alloy composition adopts the Martensite phase, in which the nickel and titanium atoms assume a very different arrangement—one that is very easy to bend and deform. Subsequently, when the deformed metallic alloy is reheated to the chosen transition temperature range between 25–35° C., thermal motion causes the atoms to snap back into the Austenite phase, thereby restoring the fixed memory-shaped configuration of the object [*Invention & Technology*, Fall 1993, pages 18–23].

For purposes of practicing the present invention, it is most desirable that the shape-memory alloy composition be prepared in a metallic blend and formulation such that the temperature transition phase occurs at a temperature less than about 35° C.; but greater than about 25° C.; and preferably be in the range from about 30–35° C. This preferred 30–35° C. transition phase temperature range is dictated by the demands of the human body which maintains a normal temperature at about 37° C. (98.6° F.); and typically shows a normal temperature range and variance of one or two degrees Celsius above and/or below this normative temperature standard. It is for this reason that the broad temperature range be about 25–35° C. and the preferred temperature transition occur in the range of 30–35° C.; but that such transformation into the intended and fixed memory-shaped configuration occur at least by a temperature of 35° C. to insure a safety margin of medical usefulness.

B. Thermoelastic Properties Of The Linking Connector

The shaped connector configurations of the thermoelastic alloy composition at temperatures less than about 25–35° C. (a temperature below its transition temperature at which the alloy exists in the Martensite phase) may take a broad variety of different lengths, diverse dimensions, and disparate overall configuration. Merely exemplifying the range and diversity of three-dimensional forms into which the alloy compositions can be shaped into a linking connector structure at temperatures below 25° C. are those illustrated by FIGS. 34–37 respectively. For purposes of practicing the present invention, FIGS. 34–35 are considered more preferred embodiments and constructions of the shaped alloy structures, while FIGS. 36–37 respectively represent formats and fabrications of the deformed in-situ alloy compositions in less frequently utilized shaped configurations.

Effect of Temperatures Less Than and Greater Than 25–35° C.

As illustrated and embodied by FIGS. 34A and 34B, the deformable in-situ, thermoelastic linking connector is a substantially cylindrical-shaped collar which is open at each of its ends 302, 304. The linking connector 300 is hollow; is substantially round or oval (in cross-sectional view); and has a determinable first configuration and dimensions initially which are deformed at will into a second memory-shaped configuration when placed at a temperature greater than about 25–35° C.

It is most desirable that the thermoelastic material constituting the sidewall 306 of the connector 300 be prepared and shaped as a first-configuration along the axis AA' as shown within FIG. 34A; and that the thermoelastic material constituting the sidewall 306 be an open-weave pattern of a memory-shaped alloy rather than take form as a solid mass of thermoelastic alloyed material. For this reason, the sidewall 306 illustrated within FIG. 34A appears in the first configuration as an open meshwork of wires 308 which are intertwined to form a substantially hexagonal pattern. This open meshwork of wires 308 provides the desired resiliency, flexibility, and memory-shaped deformation capability (particularly along the axis AA') such that the first or upper cuff portion of the sidewall 306 will become deformed and flared outwardly on-demand to yield the memory-shaped second configuration constituting the flared-lip deformity 310 shown by FIG. 34B.

It will be recognized and appreciated that the deformed cuff portion shown by FIG. 34B is merely the result of removing the cuff structure from a temperature less than 25–35° C. and placing it into a temperature environment greater than about 35–35° C. Thus, solely as a consequence of the change in temperature, the uppermost cuff portion 309 of the open meshwork of wires 308 above the axis AA' has become deformed in-situ such that the upper sidewall 309 adjacent to the open end 302 has expanded outwardly, flared, and become bent into a curved lip configuration in the memory-shaped deformed state. Note that FIG. 34B shows the upper deformation in the fully deployed state; while the open meshwork of wires constituting the lower retaining portion 307 of the sidewall 306 at the other open end 304 remains relatively stable and substantially unaltered in its original shape and state. Alternatively, however, the lower retaining sidewall portion 307 can be made to expand or diminish slightly so that it will annularly fit more tightly outside of or within the conduit wall. The deformation in-situ thus is controlled thermally and the forces at the upper curve sidewall portion from the AA' axis cause the outwardly extending, flared lip result as the fully deployed state. Moreover, the resulting flared lip zone 310 retains structural strength and resiliency as an open meshwork of superelastic wires despite having been deformed in-situ and deployed in full. The ability of the first cuff portion to be deformed and deployed in the manner illustrated by FIGS. 34A and 34B respectively is an attribute and characteristic of each embodiment and construction for the thermoelastic linking connector.

The construction and design for the linking connector is an example of the engineering principle that structural form at will follow intended function. As a component part of the system apparatus and methodology for attaching a tubular conduit in-vivo, the functions of the linking connector are twofold in nature: (1) the temperature-deformable linking connector is intended to engage and become joined to either a synthetic duct prosthesis or a previously excised vascular segment which will serve as the tubular conduit in-vivo; and (2) the temperature-deformable linking connector is intended to be positioned within the internal lumen of an unobstructed major blood vessel (such as the aorta) or within a hollow organ cavity such that a first portion of the connector wall becomes positioned and secured within the internal lumen (the blood flow channel) of the unobstructed blood vessel or the interior of the hollow organ permanently in a fluid-tight manner. Thus, as illustrated by the embodiments of FIGS. 34A and 34B, the uppermost cuff region 309 of the alloy comprising the linking connector will be deformed on-demand merely by warming the article to a temperature greater than 25–35° C.; and such deformation when deployed into a flared outwardly bent form will become secured within the lumen of the unobstructed artery or vein or the cavity of the hollow organ. Concomitantly, the retained portion 307 will remain permanently joined in substantially unaltered form to the tubular conduit.

Several attributes and characteristics are commonly to be shared among all embodiments and constructions of the thermally deformable and deployable on-demand linking connector. These include the following:

(a) Only a portion of the alloy material constituting the memory-shaped linking connector need be thermally deformable and deployable on-demand. For convenience and greater facility in achieving such temperature initiated deformation in the degree and at the time desired, it is preferred that the alloy composition forming the linking connector be an open weave or wire meshwork rather than a solid sheet alloy mass, which is considered to be more difficult to deform in a thermally-controlled manner. There is, however, no substantive restriction or limitation as such at any time or under any intended use circumstances which necessitates an avoidance of a solid sheet of material, either as a single alloy sheet or as a laminated plank of alloy material. Accordingly, the choice of whether to use an open wire meshwork or a solid sheet of alloy material is left to the discretion of the user.

(b) The thermoelastic linking connector need only be comprised of superelastic, resilient and flexible metallic alloy matter. A number of different alloys of varying formulations may be usefully employed when making a deformable memory-shaped linking connector suitable for use with the present invention. Among the desirable alloy formulations are those characterized by Table 1 above.

(c) After the deformable in-situ and deployable at will linking connector has been manufactured using shape-memory alloy materials, the first configured cuff portion structure (prior to thermal deformation) may be covered to advantage with one or more biocompatible coatings. These biocompatible coatings are intended to water tighten the article and to facilitate the sewing of the tubular conduit to the linking connector as well as to reduce the interactions of the immune system and tissue reaction with the prepared communicating channel after it has been secured in their appropriate locations in-vivo. Such biocompatible coatings are conventionally known; will reduce the severity and duration of immune or tissue reactions which frequently disrupt or interfere with grafts; and are considered desirable in a majority of use instances in order to minimize the body reaction to surgery. A representative listing of biocompatible coatings deemed suitable for use with the deformable thermoelastic connector is provided by Table 2 below.

TABLE 2

Biocompatible Coatings

High temperature pyrongen-free carbon;
Polytetrafluoroethylene (PTFE) and other polyhalogenated carbons;
Fibronection;
Collagen;
Hydroxyethyl methacrylates (HEMA);
Serum albumins;
Suprafilm (Genzyme Corp.);
Silicone polymer;
Polyurethanes;
Tetrathane (Dupont);
Polytetramethylene polymers;
Dacron;
Polyester woven fabric; and
Polycarbonated urethanes.

(d) Although the configuration of the memory-shaped linking connector prior to thermal deformation (as exemplified by FIG. 34A) may appear as a geometrically regular and coherent structure, there is no requirement or demand that either the detailed structure or overall appearance of any configured connector conform to these parameters. Accordingly, it will be recognized and understood that the deformable and deployable shape-memory alloy structure need not take form as a completely encircling band or collar of thermoelastic material. To the contrary, L-shaped, T-shaped or H-shaped constructions of alloy material where the annular sidewalls do not overlap or join completely and/or where a gapped distance separates the arms of the linking connector are both permitted and envisioned. Moreover, although the isotropic cylindrical-shaped format of the connector illustrated by FIG. 34 is highly desirable in many instances, there is no requirement that the diameter of the connector structure prior to or after thermal deformation be constant or consistent over its entire axial length. Thus, anisotropic structures as well as isotropic constructions are intended and desirable. In this manner, the linking connector in its initial state prior to thermal deformation may have a variable internal diameter over the axial length of the article in which one open end may be either greater or lesser in size than the other open end; and there may be multiple increases and decreases in diameter size successively over the entire axial length of the connector itself. All of these variations in construction and structure are within the scope of the present invention.

Figure 35B:
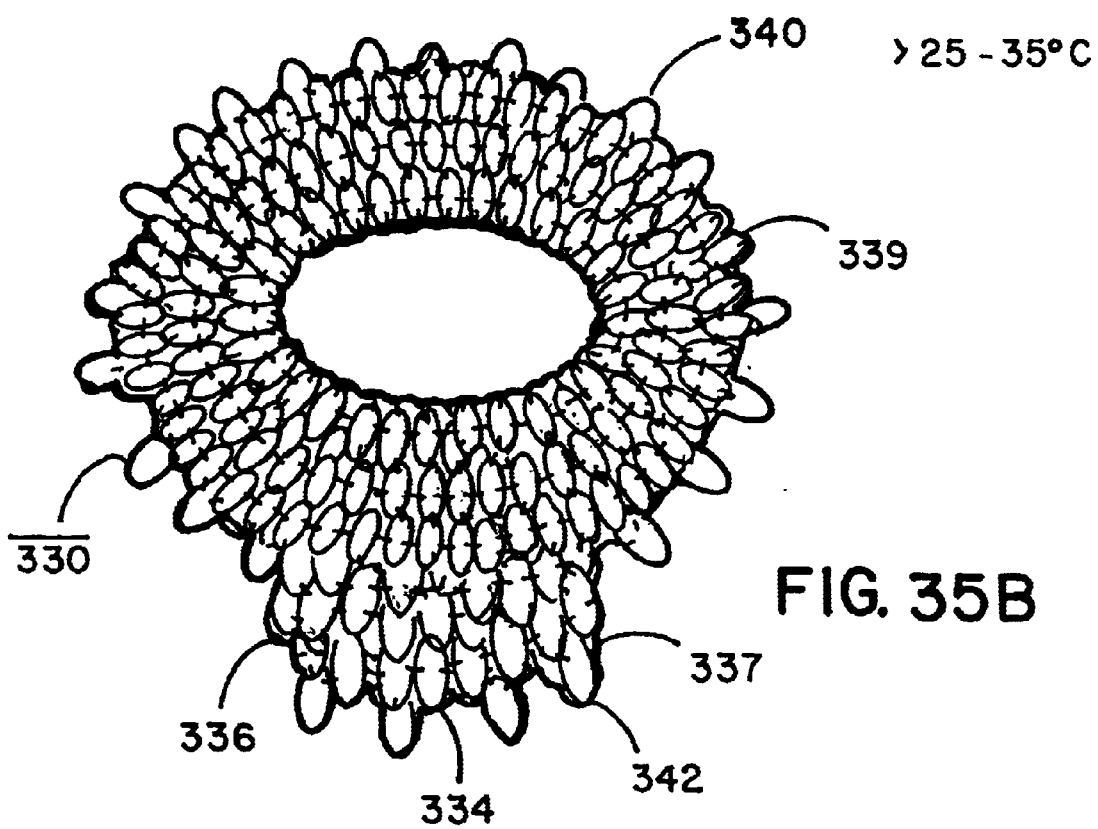
FIGS. 35A and 35B are illustrations of a second linking connector.
Figure 35A:
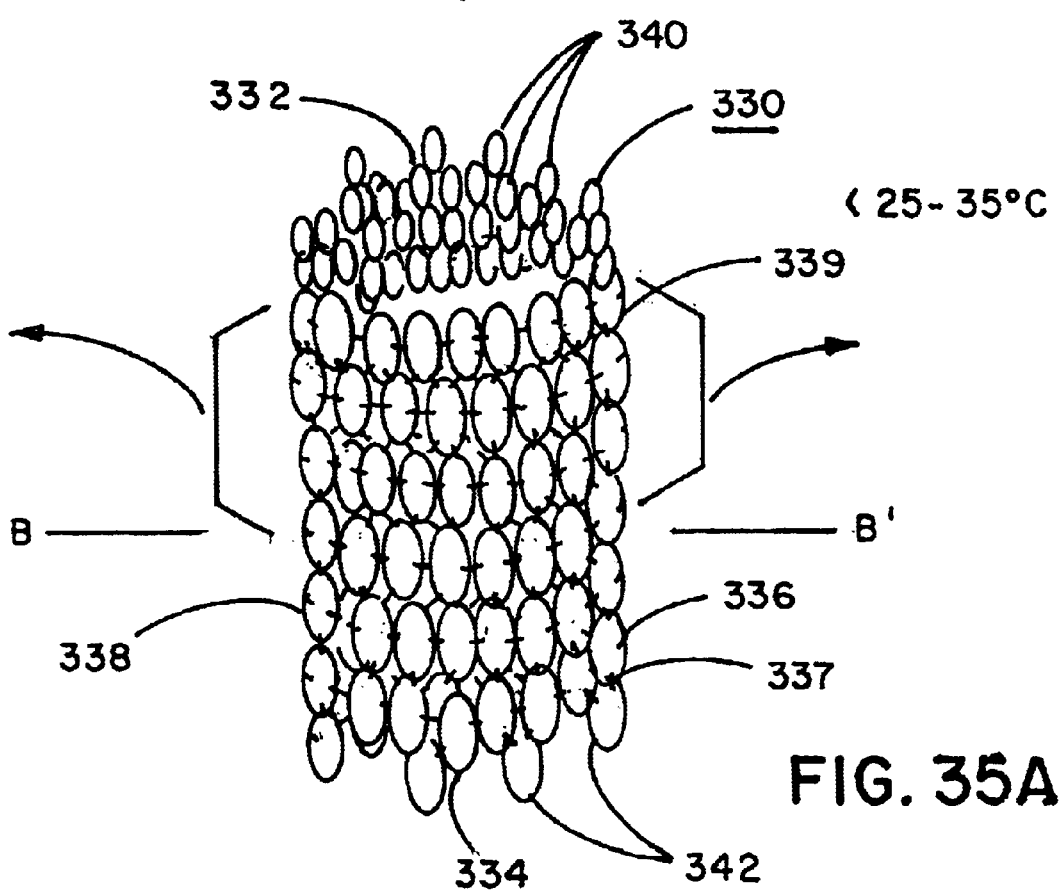

To illustrate some of the more common variations and differences available and envisioned for a deformable in-situ and deployable at will linking connector intended for use with the present invention, the alternative embodiments illustrated by FIGS. 35–37 are provided. As shown within FIGS. 35A and 35B, the initial shaped configuration for the thermoelastic structure 330 appears as a cylindrical-shaped article or cuff having two open ends 332, 334 and a rounded sidewall 336. The body of the sidewall 336 is an open meshwork of closed wire loops 338, each closed wire loop being joined at multiple points along its perimeter to at least one other closed wire loop—thereby forming an open grid meshwork. A notable feature of the connector construction within FIG. 35A is the outer edges of the open ends 332, 334, each of which is formed by a closed wire loop which is more easily bent and thermally deformed in-situ than the closed-loop meshwork in the middle of the sidewall 336. In many instances, the availability of closed-loop edges 340, 342 provide an enormous benefit and advantage when thermal deformation of the linking connector occurs in-situ. In addition, the first portion of the article shown by FIG. 35A has been memory-shaped to deform substantially at the midline along the axis BB' such that the upper sidewall upper portion 339 near the open end 332 and the edge 340 will deform in-situ and flair outwardly as a consequence of placing the sidewall in a temperature environment greater than about 25–35° C.

The result of thermal deformation in-situ at a temperature greater than about 25–35°C. and deployment of the deformation in full is shown by FIG. 35B. The sidewall upper portion 339 has become deformed and bent from the open end 332 to about the midline axis BB'. However, the lower sidewall retainer portion 337 has remained substantially unaltered overall its surface area from the midline axis BB' to the other open end 334. The full deployment of this memory-shaped second configuration is illustrated by FIG. 35B and represents the thermally deformed structure which attaches and secures a tubular conduit to the internal lumen of an artery or vein in-vivo or into the internal cavity of a hollow organ.

Figure 36A:
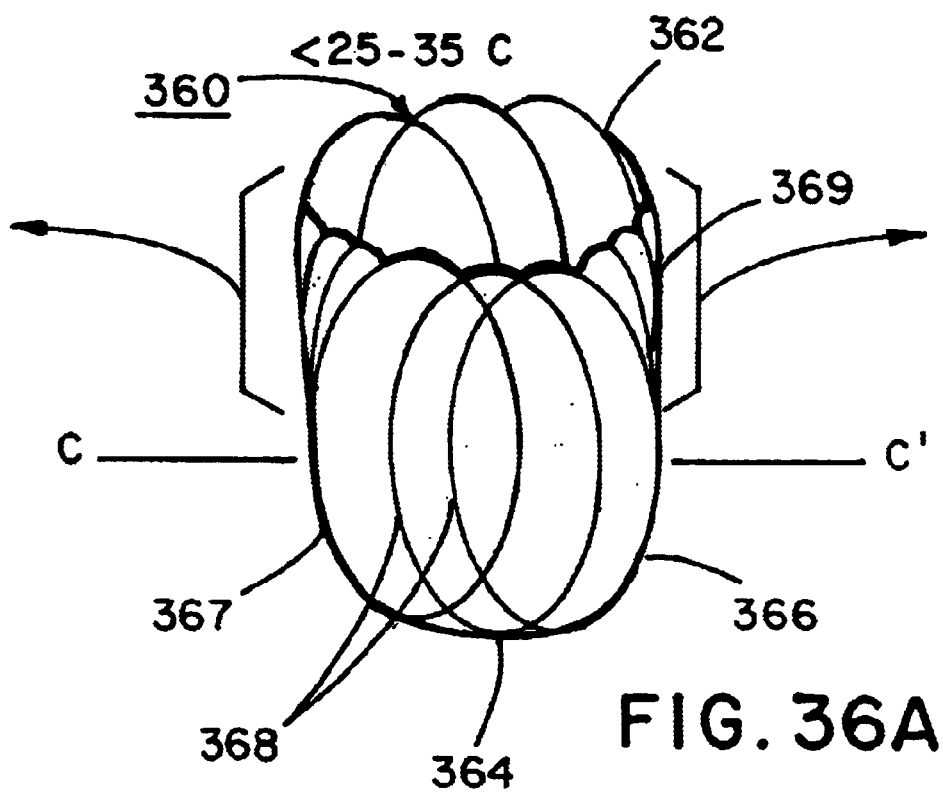
FIGS. 36A and 36B are illustrations of a third linking connector.
Figure 36B:
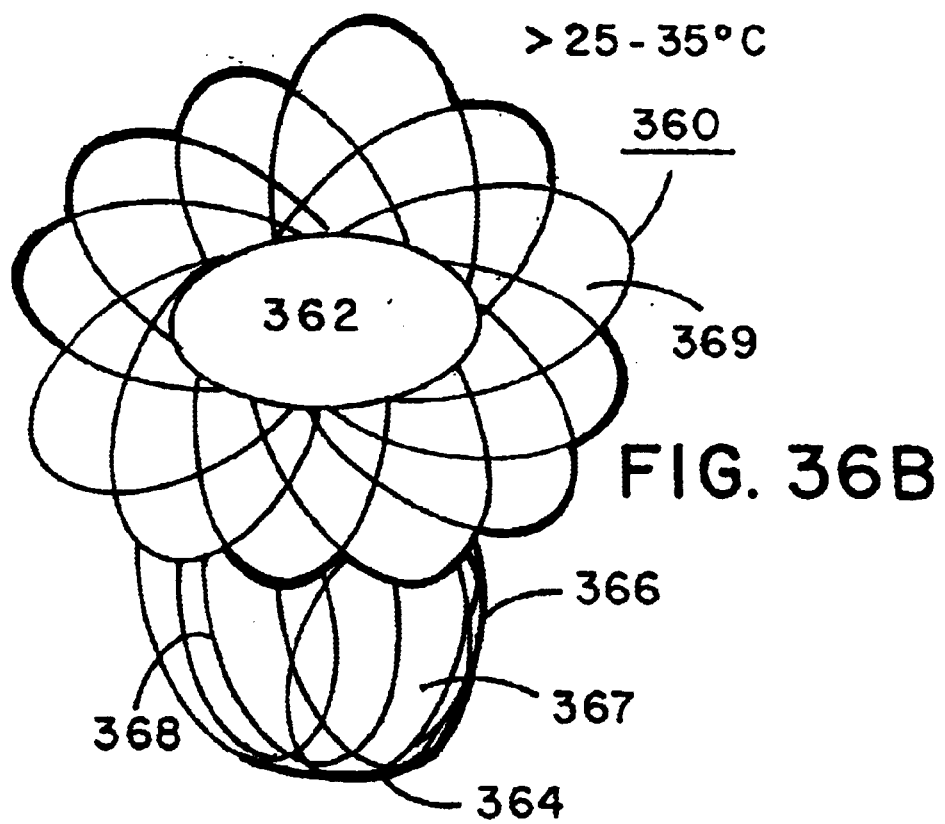

A third embodiment of a thermally deformable linking connector is illustrated by FIGS. 36A and 36B. As shown therein, the initial configuration for the deformable linking connector 360 is illustrated by FIG. 36A and appears primarily as a series of coiled wires 368 whose overlapping and intersecting junctures have been fused together to make a coiled unitary article. The deformable article has two open ends 362, 364 and an open coiled sidewall 336 formed from the commonly fused coils of wire. The open lattice work of coiled wires 368 provides the flexible and resilient meshwork suitable for achieving the primary functions of the memory-shaped linking connector. The sidewall 366 also has been pre-stressed along the middle axis CC' such that the uppermost sidewall portion 369 will become bent and deformed outwardly when exposed to an environment temperature greater than about 25–35° C.

The consequence of placing the coiled linking connector in an ambient temperature greater than about 25–35° C. is shown by FIG. 36B. It will be appreciated that the memory-shaped configuration of FIG. 36B is intended to be an in-situ generated event and result, which can be deployed fully and completely at will. Thus, when fully deformed and deployed, the flared out upper sidewall portion 369 has become bent at nearly a 90 degree angle with respect to the lower retained sidewall portion 367; and the midline CC' will generally serve as the axis of thermal deformation and deployed curvature for the coiled linking connector.

Figure 37A:
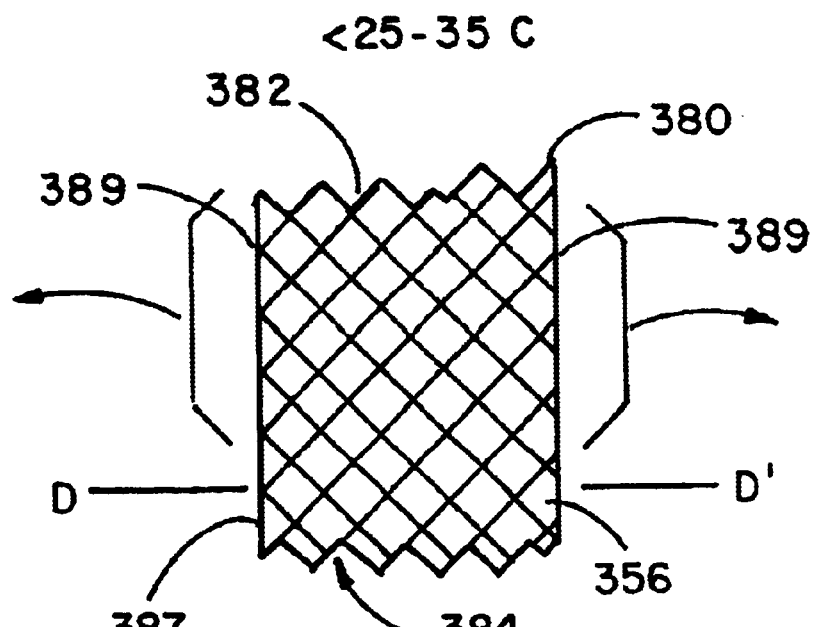
FIGS. 37A and 37B are illustrations of a fourth linking connector.
Figure 37B:
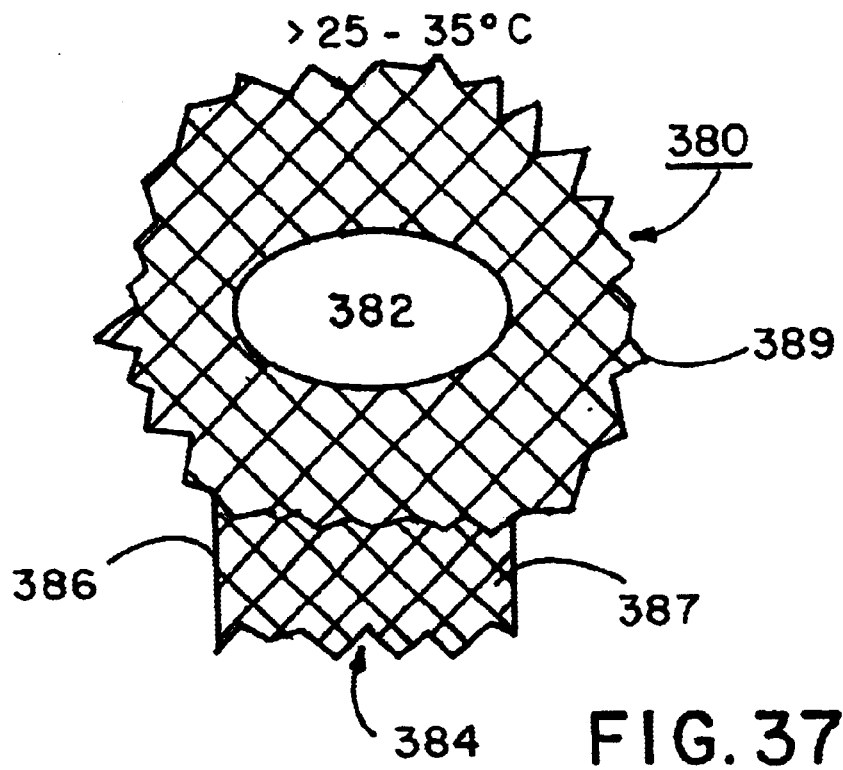

A fourth alternative embodiment is provided by FIGS. 37A and 37B in which a thermally deformable cuff or band-shaped linking connector 380 is shown having two open ends 382 and 384. In this instance, however, the sidewall 386 of the linking connector is comprised of a solid sheet of alloy material. Two other features are also included in this embodiment of the thermally deformable structure due to its construction using a solid sheet of resilient material as the sidewall 386 for the linking connector. The sidewall 386 has been preferably pre-scored to form crosshatched squares over the axial length of the sidewall; and the pre-scored sidewall thus will deform far more easily and bend outwardly along the scored lines of demarcation as shown when the linking connector is placed in an ambient temperature greater than 25–35° C. Similarly, the sidewall material has been pre-stressed along the midline axis DD' such that the upper most region 389 nearest the opening 382 will become bent far more easily and deform in a controlled fashion when and as required by the user. The effect and consequences of placing the linking connector 380 in an ambient environment whose temperature is greater than about 25–35° C. is shown by FIG. 37B. The 16 1 uppermost sidewall portion 389 has thermally deformed into the memory-shaped second configuration; and in the fully deployed state has become bent into a curved lip extending outwardly from the midline axis DD'. However, the lower sidewall portion 387 has remained substantially unchanged from its initial shape and size. The memory-shaped deformation characteristics have thus generated an in-situ deformation and deployed configuration most suitable for the attachment and securing of a tubular conduit in-vivo.

C. Superelastic Properties of the Linking Connector

It will be noted and appreciated also that the superelastic properties and use characteristics of the linking connector as a structural entity exist in addition to and concurrently with its thermoelastic properties and the ability to thermoelastically deform in-situ on-demand. The superelastic properties of each linking connector in any of its many structural formats typically include: (a) extreme elasticity in being able to return to its original size and shape after having been stretched, compressed or altered in configuration; (b) resilience in which the strain or energy created by a bending movement, force, torque or shear force and applied to an elastic material is converted and does not cause fragmentation, or cracking, or a mechanical breakdown of the material; and (c) malleability in being able to be mechanically altered in shape or configuration (whether by rolling, forging, extrusion, etc.) without rupture and without pronounced increase in resistance to deformation. For purposes of practicing the present invention, all of the conventional nickel-titanium metallic formulations which are shape-memory alloys as described herein and characterized: by Table 1 previously also are alloys which have and present superelastic properties.

The value of employing linking connectors which exhibit superelastic properties in addition to their demonstrable thermoelastic capabilities lies in the user's ability to control separately and individually the physical deployment of the linking connector in its intended memory-shaped configuration—in terms of choosing the precise timing, physical location, and exact placement—after thermoelastic deformation and shape-memory reconfiguration of the linking connector structure itself has been initiated. Thus, the act of and means for controlled deployment—the spreading or arranging in appropriate position—for the linking connector is separate and distinct from the thermal initiation and event of thermoelastic deformation on-demand for the linking of connector in-situ. The differences are easily illustrated by easy reference to the introducer assemblies shown by FIGS. 8B and 29 and to the method of introducing a prepared communication channel to a blood vessel or hollow organ as illustrated by FIGS. 9–14 and 30–33 respectively.

It is the user's choice and option, whether by personal intent or necessity, when to allow the linking connector (then joined to the tubular conduit) to reach the critical temperature required for thermal deformation to occur. However, once this critical temperature is reached, thermal deformation and thermally caused alteration of the linking connector transient structure into its permanent memory-shaped configuration will occur—if and only if there is then sufficient physical space and ambient environment room for the act of structural deformation to be performed fully and completely. Yet, if the linking connector (and the joined tubular conduit) lie within a constrained and limited space and/or a close boundary environment at the moment of thermoelastic initiation, then the thermally initiated act of deformation and reconfiguration becomes restrained, incomplete, repressed, and unfulfilled. No physical deployment and actual structural alteration into the shape-memory configuration can or will occur unless and until the physical constraint(s) are removed and the linking connector is released and has sufficient spatial freedom of movement and rotation to complete the act of shape deformation in fill and to present the intended shape-memory configuration in an unconfined form.

Accordingly, if for example the critical temperature were reached for the linking connector 82 as shown in FIG. 29, the initiation and event of thermoelastic deformation will have occurred and begun in-situ while the linking connector was spatially confined within the internal volume of the sheath 250; and the first sidewall portion 84 of the linking connector would be physically constrained and be prevented from deforming in full by the limited space and physical obstruction created by the interim diameter size of the volumetric sheath 250. Similarly, as seen in FIG. 30, the first sidewall portion 84 remains restrained and confined by being positioned within the recessed furrow 267 of the perforating headpiece 230 such constraint and physical confinement is removed and the linking connector released from the constrained setting for an at-will controlled deployment and proper positioning by the acts shown in FIG. 31.

It is essential therefore to recognize and appreciate that while thermoelastic deformation in-situ for the linking connector occurred on-demand—that is, within the volumetric sheath of the introducer assembly, the act of physically deploying the thermoelastically activated linking connector was purposefully delayed and the act of thermal deformation itself was restrained and controlled spatially until the moment the user chose for most effective anatomic placement and appropriate local positioning for the memory-shaped configuration. Clearly, it is the superelastic properties of the alloy formulations which provide the user with the capability not only to separate the individual act of thermoelastic deformation in-situ on-demand from the act of spatial deployment and constrained control at will of the spatial deployment of the thermoelastically deforming linking connector; but also to allow the user to choose for himself the precise timing, physical location, and proper placement for the deployment of a thermoelastically deforming linking connector as a direct consequence and result of being able to control such spatial deployment.

D. The Tubular Conduit

The tubular conduit comprises any biocompatible tube, sleeve, channel, flow line, hose, piping, duct, or configured outlet which allows and provides an unobstructed conveyance and transport of fluid matter through its interior space. By definition, the term "fluid matter" includes and encompasses any and all flowing solids, liquids, and/or gases as well as any mixture of these materials without regard to their chemical composition, degree of purity, amassed volume or quantity, and/or medical significance or value.

The tubular conduit has at least one tubular wall of fixed axial length; has at least one proximal end for entry; has at least one distal end for egress; and has at least one internal lumen of a volume sufficient to allow for on-demand passage therethrough of any fluid matter.

Many different types and constructions of tubular conduits are conventionally known and used; and a wide range and variety of tubular conduits are available which are extremely diverse in shape, design, and specific features. All of the essential requirements of a tubular conduit exist as conventional knowledge and information; and all of the information regarding conduit design and described in summary form hereinafter is publicly known, widely disseminated, and has been published in a variety of texts. The reader is therefore presumed to be both familiar with and have an in-depth knowledge and a general understanding of conventional tubular conduits.

A number of specific types of tubular conduits are known today; but for purposes of practicing the present invention, a number of newly designed or specifically designed conduits of varying lengths and sizes suitable for use are expected and intended to be developed and manufactured subsequently. Equally important, minor modifications of the presently existing general categories of tubular conduits are equally appropriate and are expected to be found suitable for use when practicing the present invention.

Merely representative of tubular conduits in general without regard to their specific past usages or intended applications, are those illustrated by FIGS. 38–47 respectively. As exemplified by FIGS. 38A and 38B, a tubular conduit 550 is seen having a tubular wall 552 of fixed axial length; having two proximal open ends 554 and 556 which together generate the egress and exit to the interior of the conduit, a single internal lumen 558.

Figure 39:
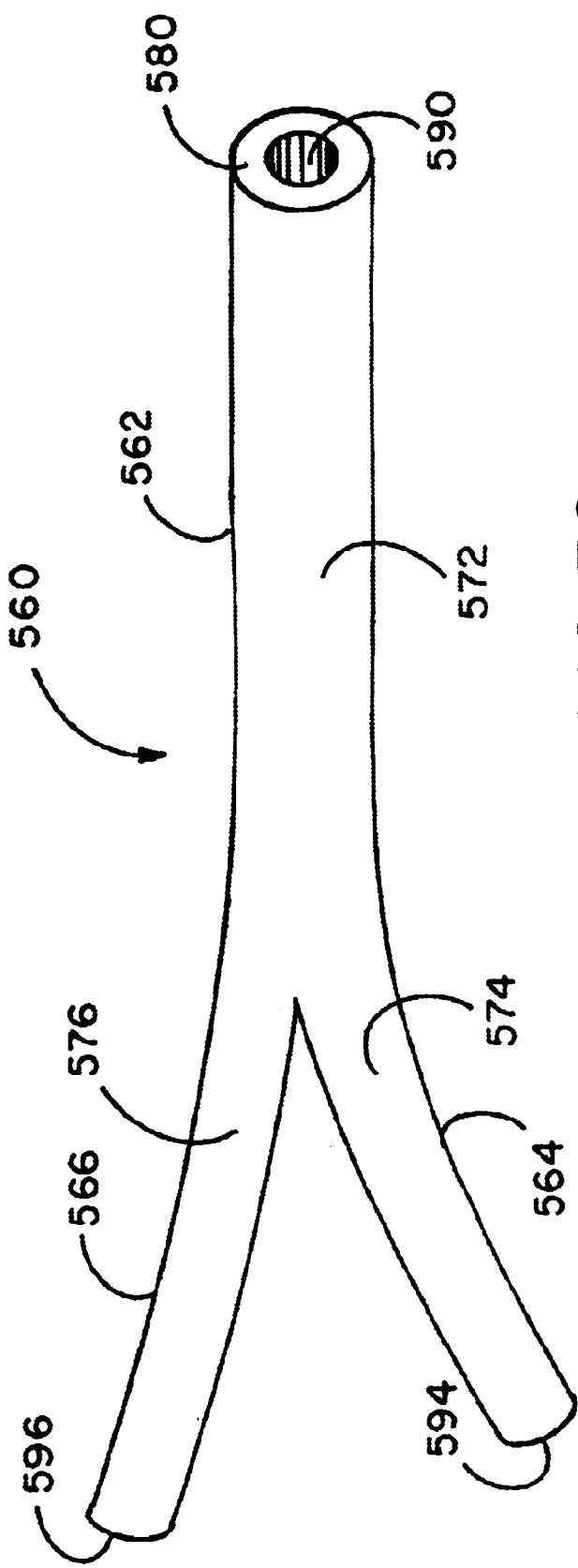
FIG. 39 is an illustration of a multi-branched tubular conduit.

Another variation commonly known is illustrated by FIG. 39 which shows a conduit 560 having a central tubular wall portion 572 of fixed axial length; having two or more branches 574, 576 respectively which collectively form the proximal ends 596, 594 for entry into the internal volume of the conduit; and a single unbranched end 580. It will be appreciated and understood that FIGS. 3847 are presented merely to show the overall general construction and relationship of parts present in each flexible tubular conduit suitable for use with the present methodology.

Also, in accordance with established principles of conventional construction, the axial length of the conduit may be composed of one or several layers in combination. In most multilayered constructions, one hollow tube is stretched over another to form a bond; and the components of the individual layers determine the overall characteristics for the conduit as a unitary construction. Some multilayered conduit structures comprise an inner tube of teflon, over which is another layer of nylon, woven DACRON (polyeththylene terephthalates), stainless steel or NITONOL (nickel-titanium alloys) braiding. A tube of polyethylene or polyurethane is then heated and extruded over the two inner layers to form a bond as the third external layer. Other constructions may consist of a polyurethane inner core, covered by a layer of stainless steel or nitinol braiding, and a third external jacket layer formed of polyurethane.

Several examples of basic conduit construction and design are illustrated by FIGS. 40–47 respectively. FIGS. 40A and 40B are perspective and cross-sectional views of a single tubular wall considered the standard minimum construction for a conduit. FIGS. 41A and 41B are perspective and cross-sectional views of a thin-walled design for a single layer extruded conduit. In comparison, FIGS. 42A and 42B are perspective and cross-sectional views of a standard multilayered construction having a braided stainless steel midlayer in its structure. Finally, FIGS. 43A and 43B are perspective and cross-sectional views of a thin-walled design for a multilayered conduit with a braided stainless steel middle layer.

In addition, a number of different dual-lumen conduits are known today. These differ in size and spatial relationship between their individual lumens. The construction difference are illustrated by FIGS. 44–47 respectively which show different dual-lumen constructions for four tubular conduits having similar or identical overall diameter size.

Figure 44:
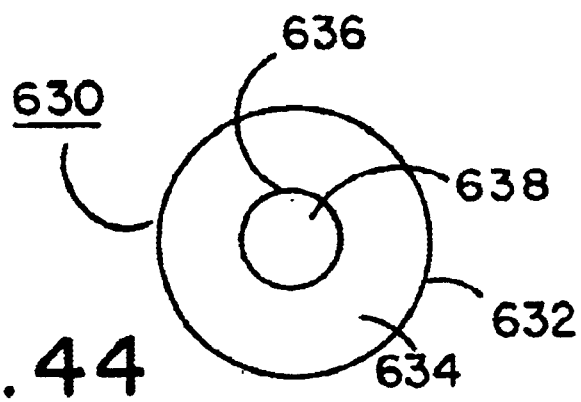
FIG. 44 is a cross-sectional illustration of a first style of internal lumen for a tubular conduit.

As shown therein, FIG. 44 shows a dual-lumen conduit 630 wherein a first external tubular wall 632 provides an outer lumen volume 634 into which a second internal tubular wall 636 has been co-axially positioned to provide an inner lumen volume 638. Clearly, the construction of conduit 630 is a co-axial design of multiple tubular walls spaced apart and co-axially spaced but separate internal lumens of differing individual volumes.

Figure 45:
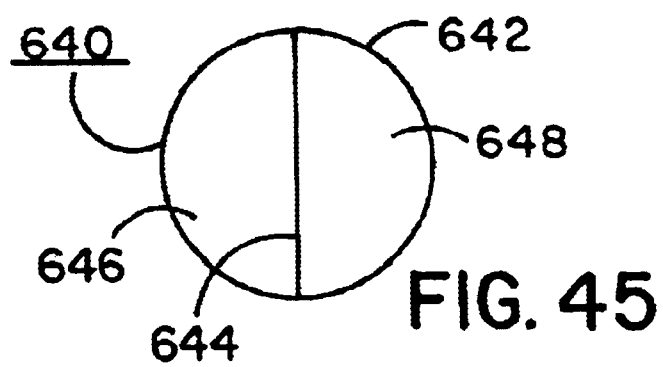
FIG. 45 is a cross-sectional illustration of a second style of internal lumen for a tubular conduit.

In comparison, FIG. 45 shows a second kind of construction and design by dual-lumen conduit 640 having a single external tubular wall 642; and an centrally disposed inner septum 644 which divides the interior tubular space into two approximately equally lumen volumes 646 and 648 respectively. Thus, in this construction, the diameter, length, and volume of internal lumen 646 is effectively identical to the diameter, length and volume of internal lumen 640; and both of these exist and are contained within a single, commnonly-shared, tubular wall.

Figure 46:
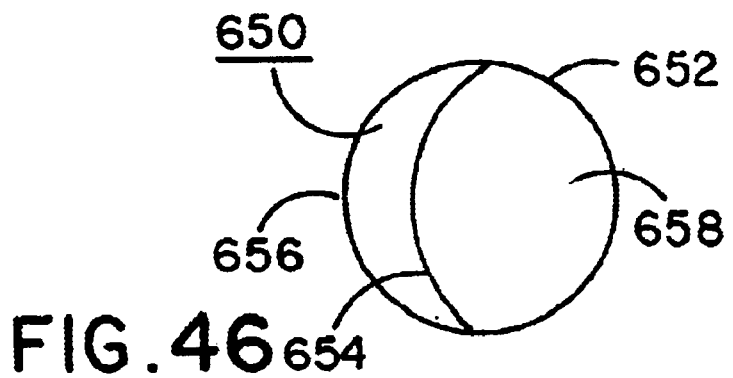
FIG. 46 is a cross-sectional illustration of a third style of internal lumen for a tubular conduit.

A third kind of construction is illustrated by FIG. 46 and shows an alternative kind of construction and design. As seen in FIG. 46, the dual-lumen conduit 656 has a single external tubular wall 652; and contains an asymmetrically positioned internal divider 650 which divides the interior tubular space into two unequal and different lumen volumes 650 and 658 respectively. Thus, in this alternative construction, the discrete volume of internal lumen 650 is markedly smaller than the volume of the adjacently positioned internal lumen 658; and yet both of these internal lumens 650 and 658 exist in, are adjacently positioned, and are both contained within a commonly-shared single tubular wall.

Figure 47:
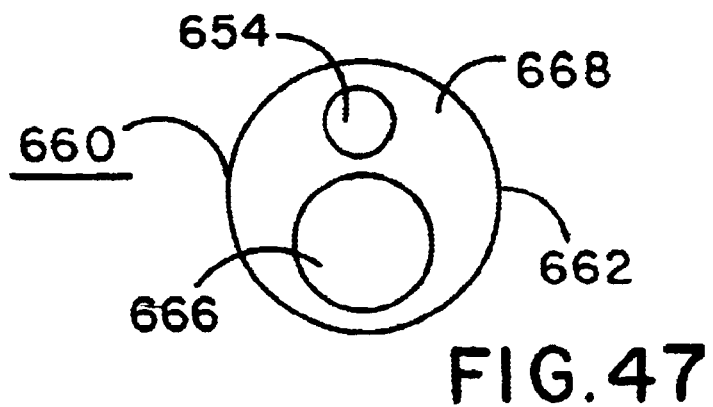
FIG. 47 is a cross-sectional illustration of a fourth style of internal lumen for a tubular conduit.

A fourth construction and design for a dual-lumen conduit is presented by FIG. 47 which shows a conduit 660 having a single external tubular wall 662 of relatively large size and thickness. Within the material substance 668 of the tubular wall 660 are two discrete bore holes 664 and 666 of differing diameters which serve as two internal lumens of unequal volume. Internal lumen 664 is clearly the smaller while internal lumen 666 is far greater in spatial volume. Yet each internal lumen volume 664 and 666 is adjacent to the other, lies in parallel, and follows the other over the axial length of the conduit.

In general, the tubular body conduit is flexible over most of its length and may have one or more bends or curves towards the ends. Conventional practice also permits using a number of differently formed ends or tips which vary in design and appearance. Accordingly, for purposes of practicing the present invention, any construction of the tubular conduit whether having one or more curves, or none; and whether or not there is more than one designed portal for exiting or entering the lumen or multiple lumens are all considered conventional variations in construction design. Any and all of these designs and constructions are therefore deemed to be encompassed completely and to lie within the general scope of construction suitable for use with the present invention.

1. Vascular Conduit Bypass Graft Material

Two major sources of conduits suitable for use as a vascular bypass graft are presently known and available. These are: synthetic prosthetic channel sections and previously excised blood vessel segments.

The choice of graft conduit is crucial to the success of coronary artery bypass grafting surgery (CABG) because the patency of a coronary conduit is closely associated with an uneventful postoperative course and a better long-term patient survival. The standard vascular conduits used for CABG are excised blood vessel segments taken from the greater saphenous vein (GSA) or another leg or arm vein. An excellent substitute conduit for coronary bypass operations that can be available on demand is certainly the desire of every practicing cardiac surgeon. However, virtually every synthetic alternative to arterial conduits or autologous fresh saphenous vein conduits has proved disappointing. Fortunately, patients with absolutely no autologous conduit are uncommon. Circumstances exist, however, that often necessitate the use of alternative synthetic conduits such as young hyperlipemic patients; as absent or unsuitable autologous internal mammary artery and greater saphenous vein as a result of previous myocardial revascularization, peripheral arterial reconstruction; and varicose vein ligation procedures. In the present era of increasing numbers of repeat coronary revascularizations, approximately 15% of patients requiring CABG are now in need of alternative synthetic conduits.

a. Synthetic Conduits

The desired characteristics of synthetic conduits used as bypass grafts are nonimmunogenicity, easy availability and storage, less risk of kinking (due to its stiffness), a less turbulent flow (due to uniform diameter), and an absence of branches.

The medical value of synthetic conduits as bypass grafts in-vivo has been substantially investigated. See for example: Foster a, *Circulation* 79 (Sup 1): 134–139 (1989); and Canver, C. C., *Chest* 108: 1150–1155 (1995); and the other references cited below. A summary review of the recent reports evaluating these conduits thus is in order.

Historically, Sauvage and associates in 1976 [*J. Thorac. Cardiovasc. Surg.* 72; 418–421 (1976)] described the placement of a 4.0-cm long, 3.5-mm diameter knitted Dacron flameouts vascular prosthesis as an interposition graft between the aorta and right coronary artery during repair of a vascular aneurysm of the ascending aorta in an adult. The graft was demonstrated to be patent by angiography 16 months after operation. A literature search at the time found only two other prior reports of successful aortocoronary grafting with synthetic conduits, both involving children with congenital coronary defects. Two factors present in all three cases that were suggested as promoting long-term patency were that only short segments of prosthetic graft were placed, and that they were implanted as interposition grafts from the end of the coronary artery to the aorta.

The initial results of CABG with expanded polytetrafluoroethylene (PTFE) (Gore-Tex. W. L. Gore and Associates, Elkton, Md.) grafts were encouraging; however, this impression was based on single-case reports or series with small numbers of patients. Molins and co-authors in 1978 [*J. Thorac. Cardiovasc. Surg.* 75: 769–771 (1978)] presented a patient in whom they had constructed a bypass to the distal right coronary artery with a 4.0 mm diameter PTFE graft, found patent on catheterization 3 months after surgery. Also, Yokoyama and associates in 1978 [*J. Thorac. Cardiovasc. Surg.* 76: 552–555 (1978)] described five aortocoronary bypass patients in whom 3.0–5.0-mm PTFE grafts had been used. Four of five of these grafts were open on restudy 3–6 months postoperatively. Subsequently, Islam and colleagues in 1981 [*J. Thorac. Surg.* 31: 569–573 (1981)] reported that a 6-mm diameter PTFE graft used for aorta-to-right coronary artery bypass remained widely patent on repeat angiography 18 months after surgery.

An indication of the early and midterm results of CABG with PTFE grafts was provided in the 1981 report of Sapsford and associates [*J. Thorac. Cardiovasc. Surg.* 81: 860–864 (1981)]. Twenty-seven coronary bypasses were constructed in 16 patients with 4.0-mm PTFE grafts. Eleven patients were restudied at 3 months after surgery, and a 61% (11 of 18) graft patency rate was found, in six patients who had repeat angiography 12–29 months after CABG, six of nine PTFE grafts were open. Then, Murta and co-authors in 1985 [*Ann Thorac. Surg.* 39: 86–87 (1985)] detailed a single case experience where two 4.0-mm diameter PTFE aortocoronary grafts remained present 53 months postoperatively. More recently, Chard and associates reported in 1987 [*J. Thorac. Cardiovasc. Surg.* 94: 132–134 (1987)] long-term patency results with PTFE aortocoronary grafts. Using both end-to-side and multiple, sequential, side-to-side anastomoses, they constructed a total of 28 distal coronary grafts in eight patients. Patency rates on repeat angiography were 64% (18 of 28) at 1 year, 32% (9 of 28) at 2 years, 21% (6 of 28) at 3 years, and 14% (4 of 28) at 45 months.

The choices of materials recognized as being suitable for the making of a biocompatible synthetic conduit are quite limited. These are provided by Table 3 below.

b. The Excised Blood Vessel Segment

A variety of blood vessel segments excised from the vascular system in-vivo are suitable for use as bypass graft conduits. A representative, but incomplete, listing is provided by Table 4 below.

TABLE 3

Synthetic Conduit Materials

Synthetic Substances

DACRON (polyethylene terephthalates) (knitted or woven) polymer;
Polytetrafluoroethylene or "PTFE" (knitted or woven);
IMPRA (polytetrafluorethylene);
TEFLON (polytetrafluoroethylene) polymer;
KEVLAR (poly-para phenylene terephthalaminde) polymer;
Polycarbonated urethan;
Silicone;
Thermoplastic polymers and elastomers; and
Collagen, human or bovine.

TABLE 4

Vascular Conduits For Bypass Grafting

Venous Conduits (a). Autologous vein conduits.
    Greater saphenous vein segments;
    Lesser saphenous vein segments;
    Upper extremity (cephalic and basilic) vein segments.
(b). Nonautologous vein conducts.
    Umbilical vein segments;
    Greater saphenous vein homografts.

Arterial Conduits (a). Autologous arterial conduits.
    Internal mammary artery segments;
    Right gastroepiploic artery segments;
    Inferior epigastric artery segments;
    Radial artery segments;
    Splenic artery segments;
    Gastroduodenal artery segments;
    Left gastric artery segments;
    Intercostal artery segments.
(b). Nonautologous arterial conduits.
    Bovine internal thoracic artery segments.

The preferred sources of blood vessels suitable for use as a vascular bypass graft are the saphenous veins. These veins constitute the superficial veins of the lower extremities and comprise both the greater (or long) saphenous and the lesser (or short) saphenous veins. Anatomically, the long saphenous vein begins on the medial side of the foot and ends in the fermoral vein below the inguinal ligaments; and the short saphenous vein begins behind the lateral malleous and runs up the back of the leg to end in the popliteal vein. However, if the saphenous veins of the particular patient are unsuitable or unavailable for any reason, either the cephalic or the basilic veins are very acceptable substitutes for use as a vascular bypass conduit. However, if these leg or arm veins are not available, synthetic or other biologic materials may also be used as substitutes.

The medical procedure to isolate and excise the saphenous vein of choice is conventionally known and considered a routine surgical technique. The saphenous vein is harvested under general anesthesia. An incision is first made in the medial malleolus, where the saphenous vein is often dilated. The saphenous vein is identified and then dissected with a single incision made along its course with scissors. Branches are doubly clamped with hemostatic clips and divided. The saphenous vein is then freed up and removed from the leg. The leg wound is closed with subcutaneous sutures and Steristrip adhesive over the incision. The vascular segment is prepared on a separate sterile table with adequate light and loupes, and branches are selectively ligated with 4-0 silk. An oval-tip needle on a syringe is inserted into the graft to gently dilate it by administering a balanced electrolyte solution (pH 7.4, chilled to 7° to 10° C.) and 10,000 units/liter of heparin. A valvulotome is inserted into the vein graft segment and the valves clipped with a 3-mm right-angle stainless steel instrument with a highly polished ball tip on the right angle. The knife edge is protected and sharply splits the cusp, causing valvular incompetence. Measurements for the approximate lengths of the grafts may be made with umbilical tapes, and the appropriate lengths may be chosen before it is sewn to the cuff and coronary arteries.

2. Tubular Conduits Suitable for use as Access Ducts

In the main, many of the same tubular conduits formulated and composed of synthetic materials may be used as access ducts when joined to a hollow organ. Accordingly, these same materials previously listed within Table 4 herein as synthetic conduit materials are most suitable and desirable for use as access duct conduits.

In addition, in order to improve the performance of the access duct conduit when joined and secured into the internal spatial volume a hollow organ in-situ, it is most desirable to provide the exterior surface of the access duct with a hydrophilic coating or to mold the entirety of the exterior surface at least using a hydrophilic plastic composition. By providing the access duct with appropriate hydrophilic properties, the tubular conduit will have a lower coefficient of friction and will more easily slide through the aperture to be made in the body cavity wall.

These highly desirable hydrophilic coatings or plastics are substantially non-reactive with respect to living tissue and are non-thrombogenic when placed in contact with blood or other body fluids. Appropriate hydrophilic coatings therefore would include polyvinylpyrrolidone—polyurethane or polyvinylbutyrol interpolymers as described in U.S. Pat. Nos. 4,100,309 and 4,119,094. In addition, appropriate molding compounds which could alternatively be applied as coatings, include hydrophilic polymer blends with thermoplastic polyurethane or polyvinylbutyrol and hydrophilic polyvinylpyrrolindone or other poly(N-vinyl lactans) as described in U.S. Pat. Nos. 4,642,267 and 4,847,324. Such hydrophilic coatings will typically reduce the coefficient of friction by over sixty percent for metals and can reduce the coefficient of friction for plastics by over ninety percent.

The present invention is not to be restricted in form nor limited in scope except by the claims appended hereto.

What we claim is:

1. A catheterless, piercing introducer assembly suitable for the introduction and sutureless juncture of a prepared communication channel to the interior space of an anatomic body part within a living subject, said introducer comprising:
   a perforator instrument comprised of
      (i) at least one elongated supporting shaft of predetermined overall dimensions and axial configuration
      (ii) a handle attached at one end to said supporting shaft; and
      (iii) a perforating headpiece integrally joined to the other end of said supporting shaft, said perforating headpiece comprising a perforating tip, a penetrating body, and a base aspect; and
   communication channel controlling means disposed adjacent to said perforating headpiece on said supporting shaft of said perforator instrument.

2. A catheterless, piercing introducer assembly suitable for the introduction and sutureless juncture of a prepared communication channel to the interior space of an anatomic body part within a living subject, said introducer assembly comprising:
   a perforator instrument comprised of
      (i) at least one elongated supporting shaft of predetermined overall dimensions and axial configuration
      (ii) a handle attached at one end to said supporting shaft; and
      (iii) a perforating headpiece integrally joined to the other end of said supporting shaft, said perforating headpiece comprising a perforating tip, a penetrating body, and a base aspect;
   channel controlling means disposed adjacent to said perforating headpiece on said supporting shaft of said perforator instrument;
   a volumetric shaft having two open ends and at least one sidewall of determinable dimensions, said sheath being
      (1) sized at one open end for on-demand placement adjacent to and aligned closure with said perforating headpiece of said perforator instrument,
      (2) substantially annular in configuration over its axial length, and
      (3) adapted for protective positioning around and volumetric spatial envelopment of at least a portion of said supporting shaft extending from said perforating headpiece of said perforator instrument, said sheath providing a protective covering for said enveloped spatial volume then surrounding said supporting shaft; and
   holding means attachable to and detachable from said volumetric sheath and said supporting shaft of said perforator instrument for holding said volumetric sheath and the enveloped spatial volume at a set position around said supporting shaft of said perforator instrument.

3. A catheterless, piercing introducer assembly suitable for the introduction and sutureless juncture of a prepared communication channel to the interior space of an anatomic body part within a living subject, said introducer assembly comprising:
   a perforator instrument comprised of
      (i) at least one elongated supporting shaft of predetermined overall dimensions and axial configuration,
      (ii) a handle attached at one end to said supporting shaft, and
      (iii) a perforating headpiece integrally joined to the other end of said supporting shaft, said perforating headpiece comprising a perforating tip, a penetrating body, and a base aspects communication channel controlling means disposed adjacent to said perforating headpiece on said supporting shaft of said perforator instrument;

a volumetric sheath having two open ends and at least one sidewall of determinable dimensions, said sheath being
  (1) sized at one open end for on-demand placement adjacent to and aligned closure with said perforating headpiece of said perforator instrument,
  (2) substantially annular in configuration over its axial length, and
  (3) adapted for protective positioning around and volumetric spatial envelopment of at least a portion of said supporting shaft extending from said perforating headpiece of said perforator instrument, said sheath providing a protective covering for said enveloped spatial volume then surrounding said supporting shaft;

position holding means attachable to and detachable from said volumetric sheath and said supporting shaft of said perforator instrument for holding said volumetric sheath and the enveloped spatial volume at a set position around said supporting shaft of said perforator instrument; and a prepared communication channel comprising
  a linking connector including at least
    a first portion of determined dimensions and configuration which is deformable on-demand, said first portion of said linking connector being suitable for passage through an aperture and deformation within the interior space of an anatomic body part whereby said deformation serves to secure said communication channel to the interior of the anatomic body part and places said secured communication channel in fluid flow communication with the interior space of the anatomic body part, and
    a second portion of determined dimensions and configuration which is permanently joined to a tubular conduit such that said joining retains and secures the tubular conduit for fluid flow communication; and
  a tubular conduit of fixed dimensions and configuration having two open ends and at least one internal lumen, said tubular conduit being permanently joined at one open end to said linking connector.

4. The introducer assembly as recited in claim 1, 2 or 3 wherein said supporting shaft is hollow over at least a portion of its length.

5. The introducer assembly as recited in claim 1, 2 or 3 wherein said supporting shaft of said perforating assembly is comprised of multiple, co-axially arranged, sliding shaft segments.

6. The introducer assembly as recited in claim 1, 2, or 3 wherein said communication channel comprises an expandable and collapsible stopper member mounted upon said supporting shaft.

7. The introducer assembly as recited in claim 1, 2, or 3 wherein said communication channel controlling means comprises an inflatable and deflatable on-demand balloon appliance disposed adjacent to said perforating headpiece.

8. The introducer assembly as recited in claim 7 further comprising a luer fitting in communication with said balloon appliance on said perforator instrument.

9. The introducer assembly as recited in claim 2 or 3 Wherein said volumetric sheath is divided into a plurality of tangs at one open end.

10. The introducer assembly as recited in claim 1, 2 or 3 further comprising an internal lumen within said perforator instrument which extends through said perforating headpiece and at least a portion of said supporting shaft.

11. The introducer assembly as recited in claim 1, 2 or 3 wherein said perforating headpiece further comprises at least one grooved recess for aligned closure with said sized open end of said volumetric sheath.

12. The introducer assembly as recited in claim 1, 2 or 3 wherein said perforating headpiece further comprises a substantially cone-shaped element disposed upon said base aspect.

13. The introducer assembly as recited in claim 2 or 3 wherein said volumetric sheath is formed as a substantially inflexible shell-like protective covering.

14. The introducer assembly as recited in claim 2 or 3 wherein said volumetric sheath is formed as a flexible fabric-like protective covering.

15. The introducer assembly as recited in claim 2 or 3 wherein said volumetric sheath further comprises a flange exteriorly mounted on the sheath sidewall at one open end.

16. The introducer assembly as recited in claim 3 wherein said linking connector of said communication channel is formed of a shape-memory alloy.

17. The introducer assembly as recited in claim 3 wherein said linking connector is a wire meshwork.

18. The introducer assembly as recited in claim 3 wherein said linking connector of said communication channel is in substantially cylindrical form.

19. The introducer assembly as recited in claim 3 wherein said linking connector of said communication channel is configured in T-shaped form.

20. The introducer assembly as recited in claim 3 wherein said linking connector of said communication channel is configured in L-shaped form.

21. The introducer assembly as recited in claim 3 wherein said linking connector of said communication channel is configured in H-shaped form.

22. The introducer assembly as recited in claim 3 wherein said communication channel further comprises a vascular bypass graft segment for a blood vessel.

23. The introducer assembly as recited in claim 3 wherein said communication channel further comprises an access duct for a hollow organ.

24. The introducer assembly as recited in claim 3 wherein said communication channel further comprises a tubular conduit formed of naturally occurring matter.

25. The introducer assembly as recited in claim 3 wherein said communication channel further comprises a tubular conduit formed of a synthetic material.

26. A perforator instrument suitable for the introduction and sutureless juncture of a prepared communication channel to the interior space of an anatomic body part within a living subject, said introducer perforator instrument comprising:
  (i) at least one elongated supporting shaft of predetermined overall dimension and axial configuration
  (ii) a handle attached at one end to said supporting shaft; and
  (iii) a perforating headpiece integrally joined to the other end of said supporting shaft, said perforating headpiece comprising a perforating tip, a penetrating body, and a base aspect.

27. A volumetric sheath suitable for use within a catheterless, piercing introducer assembly for the introduction and sutureless juncture of a prepared connecting conduit apparatus to the interior space of an anatomic body part within a living subject, said volumetric sheath comprising:

a shell covering having two open ends and at least one sidewall of determinable dimensions, said shell covering being
(1) sized at one open end for on-demand placement adjacent to and aligned closure with an introducer instrument;
(2) substantially annular in configuration over its axial length; and
(3) adapted for protective positioning around and volumetric spatial envelopment of at least a portion of a perforator instrument, wherein said volumetric sheath provides a protective covering for said enveloped spatial volume of the perforator instrument.

28. A method for introduction and sutureless juncture of a prepared communicating channel to the interior space of an anatomic body part within a living subject, said method comprising the steps of:

obtaining an introducer assembly comprised of
a perforator instrument including
(i) at least one elongated supporting shaft of predetermined overall dimensions and axial configuration;
(ii) a controlling handle attached at one end to said supporting shaft; and
(iii) a perforating headpiece integrally joined to the other end of said supporting shaft, said perforating headpiece comprising a perforating tip, a penetrating body, and a base aspect; and
communication channel controlling means disposed adjacent to said perforating headpiece on said supporting shaft;

preparing a communicating channel comprising a linking connector including at least
a first portion of determined dimensions and configuration which is permanently deformable on-demand, said first portion of said linking connector being suitable for passage through an aperture and deformation within the interior space of an anatomic body part whereby said deformation serves to secure said communicating channel to the interior of the anatomic body part and places said secured communicating channel in fluid flow communication with the interior space of the anatomic body part, and
a second portion of determined dimensions and configuration which is permanently joined to a tubular conduit such that said joining retains and secures the tubular conduit for fluid flow communication; and
a tubular conduit of fixed dimensions and configuration having two open ends and at least one internal lumen, said tubular conduit being permanently joined at one open end to said linking connector;

positioning said prepared communicating channel around said supporting shaft of said perforator;

introducing said positioned communicating channel using said introducer assembly to the interior space of an anatomic body part within a living subject such that said first portion of said linking connector of said positioned communicating channel becomes deformed and secures said joined tubular conduit to the interior space of the anatomic body part for fluid flow communication.

29. A method for introduction and sutureless juncture of a prepared communicating channel to the interior space of an anatomic body part within a living subject, said method comprising the steps of:

obtaining an introducer assembly comprised of
a perforator instrument including
(i) at least one elongated supporting shaft of predetrined overall dimensions and axial configuration;
(ii) a controlling handle attached at one end to said supporting shaft; and
(iii) a perforating headpiece integrally joined to the other end of said supporting shaft, said perforating headpiece comprising a perforating tip, a penetrating body, and a base aspect;
a volumetric sheath having two open ends and at least one sidewall of determinable dimensions, said sheath being
(1) sized at one open end for on-demand placement adjacent to and aligned closure with said perforating headpiece of said perforator instrument,
(2) substantially annular in configuration over its axial length, and
(3) adapted for protective positioning around and volumetric spatial envelopment of at least a portion of said supporting shaft extending from said perforating headpiece of said perforator instrument, said sheath providing a protective covering for said enveloped spatial volume then surrounding said supporting shaft;

position holding, means attachable to and detachable from said volumetric sheath and said supporting shaft of said perforator instrument for holding said volumetric sheath and the enveloped spatial volume at a set position around said supporting shaft of said perforator instrument; and a prepared communicating channel comprising
a linking connector including at least
a first portion of determined dimensions and configuration which is deformable on-demand, said first portion of said linking connector being suitable for passage through an aperture and deformation within the interior space of an anatomic body part whereby said deformation serves to secure said communication channel to the interior of the anatomic body part and places said secured communication channel in fluid flow communication with the interior space of the anatomic body part, and
a second portion of determined dimensions and configuration which is permanently joined to the sidewall of a tubular conduit such that said joining retains and secures the tubular conduit for fluid flow communication; and
a tubular conduit of fixed dimensions and configuration having two open ends and at least one internal lumen, said tubular conduit being permanently joined at one open end to said linking connector;

positioning said prepared communicating channel around said supporting shaft of said perforator instrument such that said volumetric sheath envelops and protects said positioned communicating channel; and introducing said positioned communicating channel using said introducer assembly to the interior space of an anatomic body part within a living subject such that said portion of said linking connector of said positioned communicating channel becomes deformed and secures said joined tubular conduit to the interior space of the anatomic body part for fluid flow communication.

* * * * *